United States Patent
Ponce et al.

(10) Patent No.: US 11,603,551 B2
(45) Date of Patent: Mar. 14, 2023

(54) BIOLOGICAL INDICATORS, AND SYSTEMS AND METHODS FOR DETERMINING EFFICACY OF STERILIZATION

(71) Applicant: STERITEC PRODUCTS MFG. CO., INC., Englewood, CO (US)

(72) Inventors: Adrian Ponce, Los Angeles, CA (US); Kok-Hwee Ng, Irvine, CA (US); Darshan Yeliyur Siddegowda, Mission Viejo, CA (US); Jenna Zimmerman, Newport Beach, CA (US); Dat Nguyen, Rancho Santa Margarita, CA (US); Mitchell London, Mission Viejo, CA (US); Jake Douglas Knickerbocker, Westminster, CA (US); Edward MacLeod Perkins, Studio City, CA (US); Robert G. Waarts, Los Altos, CA (US)

(73) Assignee: STERITEC PRODUCTS MFG. CO., INC., Englewood, CO (US)

( * ) Notice: Subject to any disclaimer, the term of this patent is extended or adjusted under 35 U.S.C. 154(b) by 0 days.

(21) Appl. No.: 17/110,229

(22) Filed: Dec. 2, 2020

(65) Prior Publication Data
US 2022/0170067 A1    Jun. 2, 2022

(51) Int. Cl.
*C12Q 1/00* (2006.01)
*C12M 3/00* (2006.01)
(Continued)

(52) U.S. Cl.
CPC .............. *C12Q 1/22* (2013.01); *C12M 37/06* (2013.01)

(58) Field of Classification Search
CPC ................... C12M 37/06; C12Q 1/22
See application file for complete search history.

(56) References Cited

U.S. PATENT DOCUMENTS

| 4,261,950 A | 4/1981 | Bainbridge et al. |
| 4,671,936 A | 6/1987 | Barron |

(Continued)

FOREIGN PATENT DOCUMENTS

| EP | 0 093 920 A1 | 11/1983 |
| EP | 1 331 953 B1 | 6/2005 |

(Continued)

OTHER PUBLICATIONS

Partial International Search Report for International Application No. PCT/US2021/061479, dated Feb. 18, 2022, 11 pages.
(Continued)

*Primary Examiner* — Nathan A Bowers
(74) *Attorney, Agent, or Firm* — Lewis Roca Rothgerber Christie LLP

(57) ABSTRACT

A biological indicator includes: a BI housing; a germinant container inside the BI housing and housing a germinant composition; a germinant releaser configured to release the germinant composition from the germinant container; a germinant releaser support supporting the germinant releaser and configured to bring the germinant releaser into contact with the germinant container upon application of a force to the germinant releaser support or the germinant container; a first spore carrier inside the BI housing, the first spore carrier having a plurality of spores deposited at a first surface thereof; and an imaging window at a first surface of the BI housing. A BI reader is configured to detect and quantify the presence of live spores in the BI, and includes an excitation source, a camera for capturing images of the spores over time, and a processor for analyzing the images to determine the presence of live spores.

21 Claims, 59 Drawing Sheets

(51) Int. Cl.
*C12Q 1/22* (2006.01)
*C12M 1/12* (2006.01)

(56) References Cited

U.S. PATENT DOCUMENTS

| | | | |
|---|---|---|---|
| 4,850,716 A | 7/1989 | Baker et al. |
| 5,223,401 A | 6/1993 | Foltz et al. |
| 5,418,167 A | 5/1995 | Matner et al. |
| 5,565,634 A | 10/1996 | Graessle et al. |
| 5,745,039 A | 4/1998 | Hof et al. |
| 5,770,393 A | 6/1998 | Dalmasso et al. |
| 5,801,010 A | 9/1998 | Falkowski et al. |
| 5,856,118 A | 1/1999 | Dalmasso |
| 5,863,790 A | 1/1999 | Bolea |
| 5,866,356 A | 2/1999 | Albert et al. |
| 5,872,359 A | 2/1999 | Stewart et al. |
| 5,882,590 A | 3/1999 | Stewart et al. |
| 5,928,948 A | 7/1999 | Malchesky |
| 5,942,408 A | 8/1999 | Christensen et al. |
| 6,025,189 A | 2/2000 | Bolea et al. |
| 6,063,591 A | 5/2000 | Bolea |
| 6,121,012 A | 9/2000 | Falkowski et al. |
| 6,187,555 B1 | 2/2001 | Tautvydas |
| 6,203,767 B1 | 3/2001 | Leasko |
| 6,352,837 B1 | 3/2002 | Witcher et al. |
| 6,355,448 B1 | 3/2002 | Foltz et al. |
| 6,395,551 B1 | 5/2002 | Kipke et al. |
| 6,436,659 B1 | 8/2002 | Hui et al. |
| 6,458,554 B1 | 10/2002 | Hui et al. |
| 6,485,978 B1 | 11/2002 | Kirckof et al. |
| 6,485,979 B1 | 11/2002 | Kippenhan et al. |
| 6,488,890 B1 | 12/2002 | Kirckof |
| 6,534,006 B2 | 3/2003 | Hehenberger |
| 6,566,090 B2 | 5/2003 | Witcher et al. |
| 6,623,955 B2 | 9/2003 | Matner et al. |
| 6,630,352 B1 | 10/2003 | Reiner et al. |
| 6,653,096 B1 | 11/2003 | Christensen et al. |
| 6,884,394 B1 | 4/2005 | Hehenberger et al. |
| 6,897,059 B2 | 5/2005 | Foltz et al. |
| 6,924,139 B2 | 8/2005 | Eveland et al. |
| 7,045,343 B2 | 5/2006 | Witcher et al. |
| 7,122,150 B2 | 10/2006 | Gonzalez et al. |
| 7,157,046 B2 | 1/2007 | McVey et al. |
| 7,183,048 B2 | 2/2007 | Felkner et al. |
| 7,186,374 B2 | 3/2007 | Zelina et al. |
| 7,326,562 B2 | 2/2008 | Felkner et al. |
| 7,416,883 B2 | 8/2008 | Cregger et al. |
| 7,481,975 B2 | 1/2009 | Read |
| 7,527,766 B2 | 5/2009 | Centanni |
| 7,541,002 B2 | 6/2009 | Centanni |
| 7,602,284 B2 | 10/2009 | Wong et al. |
| 7,641,851 B2 | 1/2010 | Williams et al. |
| 7,642,067 B2 | 1/2010 | Song et al. |
| 7,700,056 B2 | 4/2010 | Hill et al. |
| 7,741,107 B2 | 6/2010 | Cregger et al. |
| 7,899,681 B2 | 3/2011 | Katzenmaier et al. |
| 7,927,866 B2 | 4/2011 | Justi et al. |
| 7,960,169 B2 | 6/2011 | Cregger et al. |
| 8,022,375 B2 | 9/2011 | Williams et al. |
| 8,039,251 B2 | 10/2011 | Cregger et al. |
| 8,043,845 B2 | 10/2011 | Franciskovich et al. |
| 8,071,362 B2 | 12/2011 | Franciskovich et al. |
| 8,084,247 B2 | 12/2011 | Cregger et al. |
| 8,110,144 B2 | 2/2012 | Morales |
| 8,173,388 B2 | 5/2012 | Pasmore et al. |
| 8,173,389 B2 | 5/2012 | Franciskovich et al. |
| D665,509 S | 8/2012 | Smith et al. |
| 8,283,133 B2 | 10/2012 | Franciskovich et al. |
| 8,343,768 B2 | 1/2013 | Kyung-Hee Song et al. |
| 8,357,083 B2 | 1/2013 | Nagai et al. |
| 8,372,624 B2 | 2/2013 | Franciskovich et al. |
| 8,389,208 B2 | 3/2013 | Sutton et al. |
| 8,486,691 B2 | 7/2013 | Larson et al. |
| 8,492,162 B2 | 7/2013 | Kippenhan et al. |
| 8,507,248 B2 | 8/2013 | Franciskovich et al. |
| 8,530,184 B2 | 9/2013 | Franciskovich et al. |
| 8,691,562 B2 | 4/2014 | Franciskovich et al. |
| 8,765,398 B2 | 7/2014 | Dalmasso |
| 8,802,392 B2 | 8/2014 | Chandrapati et al. |
| 8,822,174 B1 | 9/2014 | Franciskovich et al. |
| 8,840,837 B2 | 9/2014 | Smith et al. |
| 8,858,884 B2 | 10/2014 | Franciskovich et al. |
| 8,858,887 B2 | 10/2014 | Lacy et al. |
| 8,895,239 B2 | 11/2014 | Franciskovich et al. |
| 8,945,837 B2 | 2/2015 | Franciskovich et al. |
| 8,950,576 B2 | 2/2015 | Andreu |
| 8,969,029 B2 | 3/2015 | Chandrapati et al. |
| 8,975,067 B2 | 3/2015 | Foltz et al. |
| 8,980,622 B2 | 3/2015 | Smith et al. |
| 9,012,173 B2 | 4/2015 | Franciskovich et al. |
| 9,017,994 B2 | 4/2015 | Franciskovich et al. |
| 9,102,976 B2 | 8/2015 | Sutton et al. |
| 9,114,186 B2 | 8/2015 | Foltz et al. |
| 9,121,050 B2 | 9/2015 | Franciskovich et al. |
| 9,145,573 B2 | 9/2015 | Pederson et al. |
| 9,170,205 B2 | 10/2015 | Burns et al. |
| 9,244,013 B2 | 1/2016 | Pugh et al. |
| 9,279,141 B2 | 3/2016 | Chandrapati et al. |
| 9,303,283 B2 | 4/2016 | Franciskovich et al. |
| 9,322,046 B2 | 4/2016 | Chandrapati et al. |
| 9,334,521 B2 | 5/2016 | Robole et al. |
| 9,410,180 B2 | 8/2016 | Pederson et al. |
| 9,416,393 B2 | 8/2016 | Franciskovich et al. |
| 9,428,786 B2 | 8/2016 | Pederson et al. |
| 9,435,739 B2 | 9/2016 | Roscoe et al. |
| 9,540,677 B2 | 1/2017 | Smith et al. |
| 9,650,661 B2 | 5/2017 | Witcher et al. |
| 9,675,722 B2 | 6/2017 | Ahimou et al. |
| 9,687,578 B2 | 6/2017 | Schumacher et al. |
| 9,695,428 B2 | 7/2017 | Franciskovich et al. |
| 9,701,968 B2 | 7/2017 | Franciskovich et al. |
| 9,701,996 B2 | 7/2017 | Smith et al. |
| 9,717,812 B2 | 8/2017 | Chandrapati et al. |
| 9,726,652 B2 | 8/2017 | Lacy et al. |
| 9,738,917 B2 | 8/2017 | Dalmasso |
| 9,931,427 B2 | 4/2018 | Chin |
| 9,951,370 B2 | 4/2018 | Yu et al. |
| 10,010,636 B2 | 7/2018 | Henniges et al. |
| 10,011,843 B2 | 7/2018 | Franciskovich et al. |
| 10,011,844 B2 | 7/2018 | Franciskovich et al. |
| 10,017,772 B2 | 7/2018 | Franciskovich et al. |
| 10,047,334 B2 | 8/2018 | Chandrapati et al. |
| 10,059,977 B2 | 8/2018 | Witcher et al. |
| 10,119,946 B2 | 11/2018 | Bala et al. |
| 10,258,706 B2 | 4/2019 | Henniges et al. |
| 10,301,632 B2 | 5/2019 | Franciskovich et al. |
| 10,441,672 B2 | 10/2019 | Truong et al. |
| 10,443,083 B2 | 10/2019 | Eghbal et al. |
| 10,513,678 B2 | 12/2019 | Sullivan et al. |
| 10,561,753 B2 | 2/2020 | Thompson et al. |
| 10,596,287 B2 | 3/2020 | Dang et al. |
| 10,632,220 B2 | 4/2020 | Fang et al. |
| 10,668,180 B2 | 6/2020 | Thompson et al. |
| 10,675,118 B2 | 6/2020 | Yang et al. |
| 11,000,614 B2 | 5/2021 | Dang et al. |
| 2003/0077688 A1 | 4/2003 | Matner et al. |
| 2004/0197848 A1 | 10/2004 | Behun et al. |
| 2005/0136508 A1 | 6/2005 | Ponce |
| 2005/0239158 A1 | 10/2005 | Guiavarch et al. |
| 2006/0183183 A1 | 8/2006 | Felkner et al. |
| 2006/0263258 A1 | 11/2006 | Harris et al. |
| 2006/0292664 A1 | 12/2006 | Ponce |
| 2007/0117175 A1 | 5/2007 | Ponce |
| 2008/0070293 A1 | 3/2008 | Guiavarch et al. |
| 2012/0149094 A1 | 6/2012 | Smith et al. |
| 2013/0210048 A1 | 8/2013 | Chandrapati et al. |
| 2013/0210067 A1 | 8/2013 | Chandrapati et al. |
| 2013/0230876 A1 | 9/2013 | Roscoe et al. |
| 2013/0302849 A1 | 11/2013 | Smith et al. |
| 2015/0159192 A1 | 6/2015 | Foltz et al. |
| 2015/0167047 A1 | 6/2015 | Smith et al. |
| 2015/0337354 A1 | 11/2015 | Ahimou et al. |
| 2016/0083771 A1 | 3/2016 | Witcher et al. |
| 2016/0160261 A1 | 6/2016 | Dufresne |

(56) References Cited

U.S. PATENT DOCUMENTS

| | | |
|---|---|---|
| 2016/0228593 A1 | 8/2016 | Robole et al. |
| 2017/0037447 A1 | 2/2017 | Chandrapati et al. |
| 2017/0211035 A1 | 7/2017 | Yirava et al. |
| 2017/0211122 A1 | 7/2017 | Centanni et al. |
| 2017/0247742 A1 | 8/2017 | Doyle et al. |
| 2017/0252475 A1 | 9/2017 | Ahimou et al. |
| 2017/0253845 A1 | 9/2017 | Amin |
| 2018/0015193 A1 | 1/2018 | Swaminathan et al. |
| 2018/0071418 A1 | 3/2018 | Bommarito |
| 2018/0187142 A1 | 7/2018 | Truong |
| 2018/0187143 A1 | 7/2018 | Yirava et al. |
| 2018/0237821 A1 | 8/2018 | Fryer |
| 2018/0305733 A1 | 10/2018 | Centanni et al. |
| 2018/0355400 A1 | 12/2018 | Centanni et al. |
| 2018/0369435 A1 | 12/2018 | Dhiman et al. |
| 2019/0002951 A1 | 1/2019 | Fryer et al. |
| 2019/0017091 A1 | 1/2019 | Centanni et al. |
| 2019/0017092 A1 | 1/2019 | Franciskovich et al. |
| 2019/0017093 A1 | 1/2019 | Franciskovich et al. |
| 2019/0024137 A1 | 1/2019 | Bala |
| 2019/0025268 A1 | 1/2019 | Cregger et al. |
| 2019/0046678 A1 | 2/2019 | Tatnell |
| 2019/0071297 A1 | 3/2019 | Hayakawa et al. |
| 2019/0076009 A1 | 3/2019 | Yang |
| 2019/0076567 A1 | 3/2019 | Yang |
| 2019/0105416 A1 | 4/2019 | Jing et al. |
| 2019/0106725 A1 | 4/2019 | Cregger et al. |
| 2019/0106726 A1 | 4/2019 | Cregger et al. |
| 2019/0117810 A1 | 4/2019 | Ludowise et al. |
| 2019/0125912 A1 | 5/2019 | Bommarito et al. |
| 2019/0147727 A1 | 5/2019 | Koursaris et al. |
| 2019/0154646 A1 | 5/2019 | Xia et al. |
| 2019/0169672 A1 | 6/2019 | Fryer et al. |
| 2019/0175775 A1 | 6/2019 | Fryer et al. |
| 2019/0192714 A1 | 6/2019 | Ahimou et al. |
| 2019/0255208 A1 | 8/2019 | Bommarito et al. |
| 2019/0290796 A1 | 9/2019 | Ma et al. |
| 2019/0307910 A1 | 10/2019 | Bala |
| 2019/0307911 A1 | 10/2019 | Bala |
| 2019/0343975 A1 | 11/2019 | Biron |
| 2019/0381204 A1 | 12/2019 | Nies et al. |
| 2019/0382820 A1 | 12/2019 | Soto et al. |
| 2020/0000952 A1 | 1/2020 | Dang et al. |
| 2020/0023090 A1 | 1/2020 | Axelrod et al. |
| 2020/0030476 A1 | 1/2020 | Corsini |
| 2020/0038534 A1 | 2/2020 | Troung et al. |
| 2020/0063178 A1 | 2/2020 | Yirava et al. |
| 2020/0063179 A1 | 2/2020 | Eghbal et al. |
| 2020/0080043 A1 | 3/2020 | Sullivan et al. |
| 2020/0107905 A1 | 4/2020 | Yang et al. |
| 2020/0165658 A1 | 5/2020 | Bala et al. |
| 2020/0179549 A1 | 6/2020 | Thompson et al. |
| 2020/0179550 A1 | 6/2020 | Fang et al. |
| 2020/0199516 A1 | 6/2020 | Rhodes et al. |
| 2020/0199517 A1 | 6/2020 | Fryer et al. |
| 2021/0402033 A1 | 12/2021 | Ludowise et al. |

FOREIGN PATENT DOCUMENTS

| | | |
|---|---|---|
| EP | 2 766 054 B1 | 11/2015 |
| EP | 3 213 773 A1 | 9/2017 |
| EP | 3 213 774 A1 | 9/2017 |
| EP | 2 456 882 B1 | 10/2017 |
| EP | 3 366 315 A1 | 8/2018 |
| EP | 3 421 056 A1 | 1/2019 |
| EP | 3 222 295 B1 | 6/2021 |
| WO | WO 99/24817 A1 | 5/1999 |
| WO | WO 01/13964 A1 | 3/2001 |
| WO | WO 02/056923 A2 | 7/2002 |
| WO | WO 03/065009 A2 | 8/2003 |
| WO | WO 2005/009484 A2 | 2/2005 |
| WO | WO 2009/137442 A1 | 11/2009 |
| WO | WO 2010/039388 A2 | 4/2010 |
| WO | WO 2010/045138 A2 | 4/2010 |
| WO | WO 2010/054033 A1 | 5/2010 |
| WO | WO 2010/054095 A1 | 5/2010 |
| WO | WO 2012/061213 A1 | 5/2012 |
| WO | WO 2012/061228 A1 | 5/2012 |
| WO | WO 2012/061229 A1 | 5/2012 |
| WO | WO 2014/189716 A1 | 11/2014 |
| WO | WO 2017/106758 A1 | 6/2017 |
| WO | WO 2017/184664 A1 | 10/2017 |
| WO | WO 2018/025207 A1 | 2/2018 |
| WO | WO 2019/074639 A1 | 4/2019 |
| WO | WO 2019/220262 A1 | 11/2019 |
| WO | WO 2020/023833 A1 | 1/2020 |
| WO | WO 2020/112651 A1 | 6/2020 |
| WO | WO 2020/128975 A1 | 6/2020 |
| WO | WO 2020/129005 A2 | 6/2020 |
| WO | WO 2021/059058 A1 | 4/2021 |

OTHER PUBLICATIONS

International Search Report and Written Opinion for International Application No. PCT/US2021/061479, dated Oct. 26, 2022, 30 pages.

P.T. Yung et al., "Fast Sterility Assessment by Germinable-Endospore Biodosimetry," Applied and Environmental Microbiology, vol. 74, No. 24, Dec. 15, 2008, pp. 7669-7674.

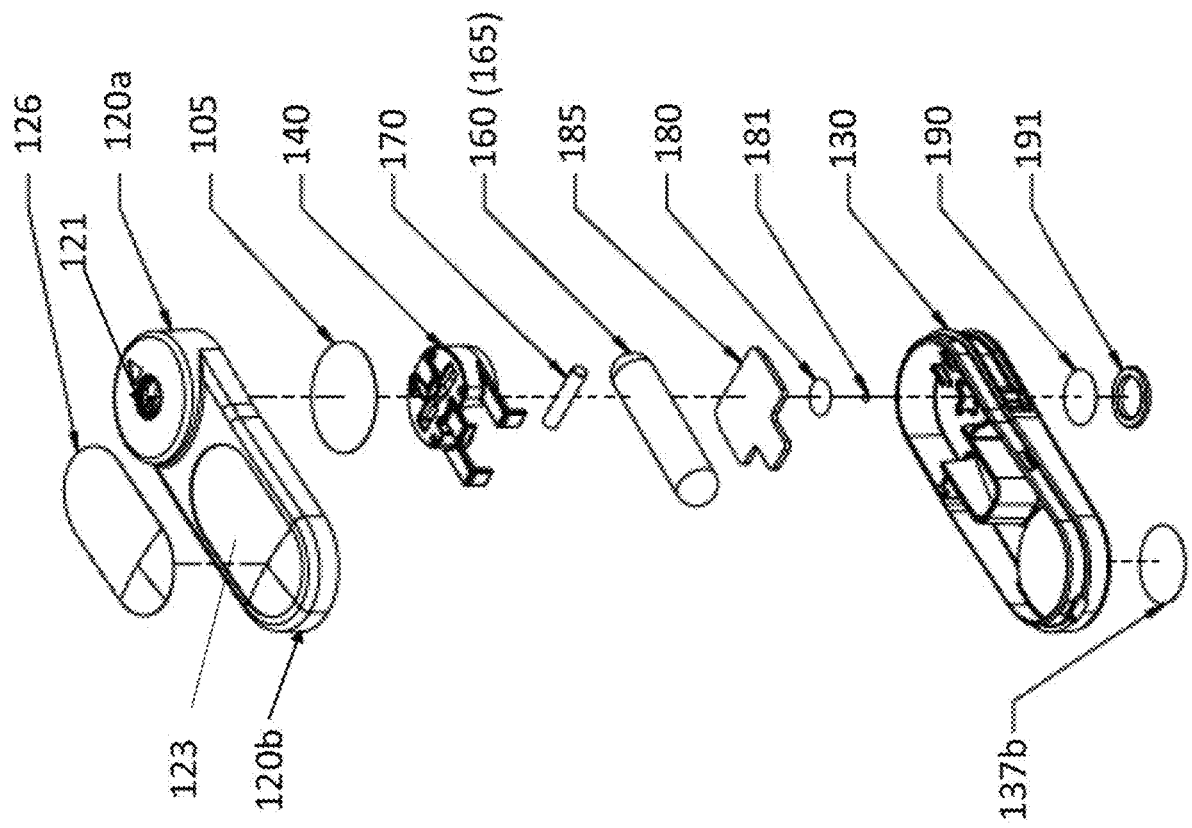
FIG. 12
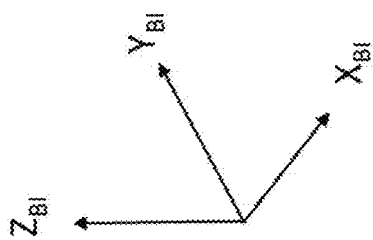

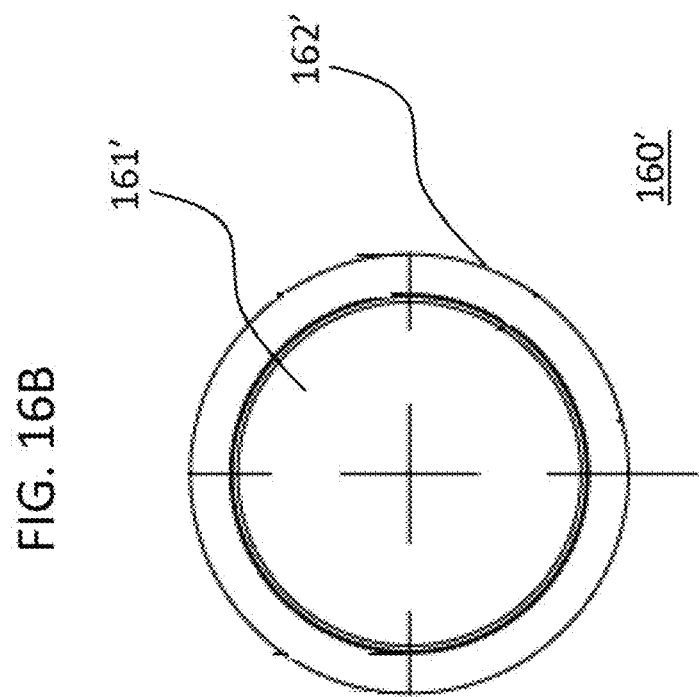
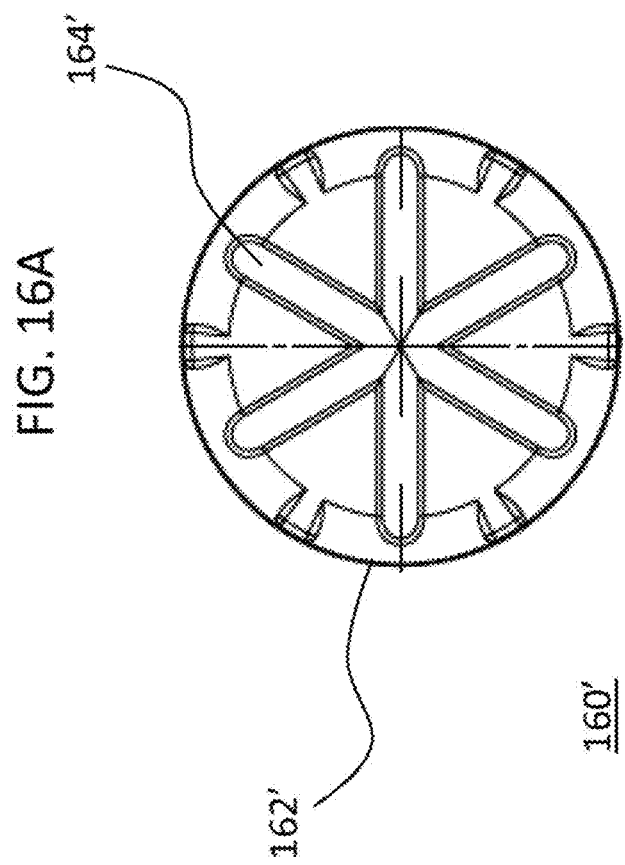

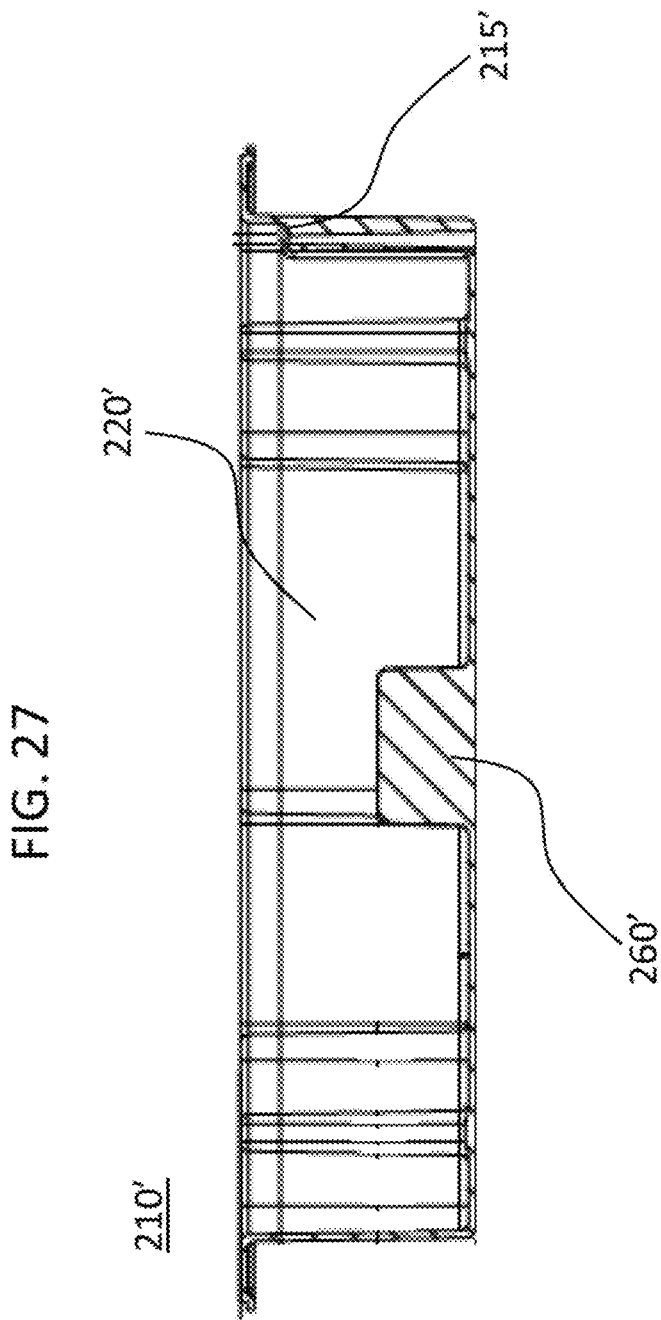

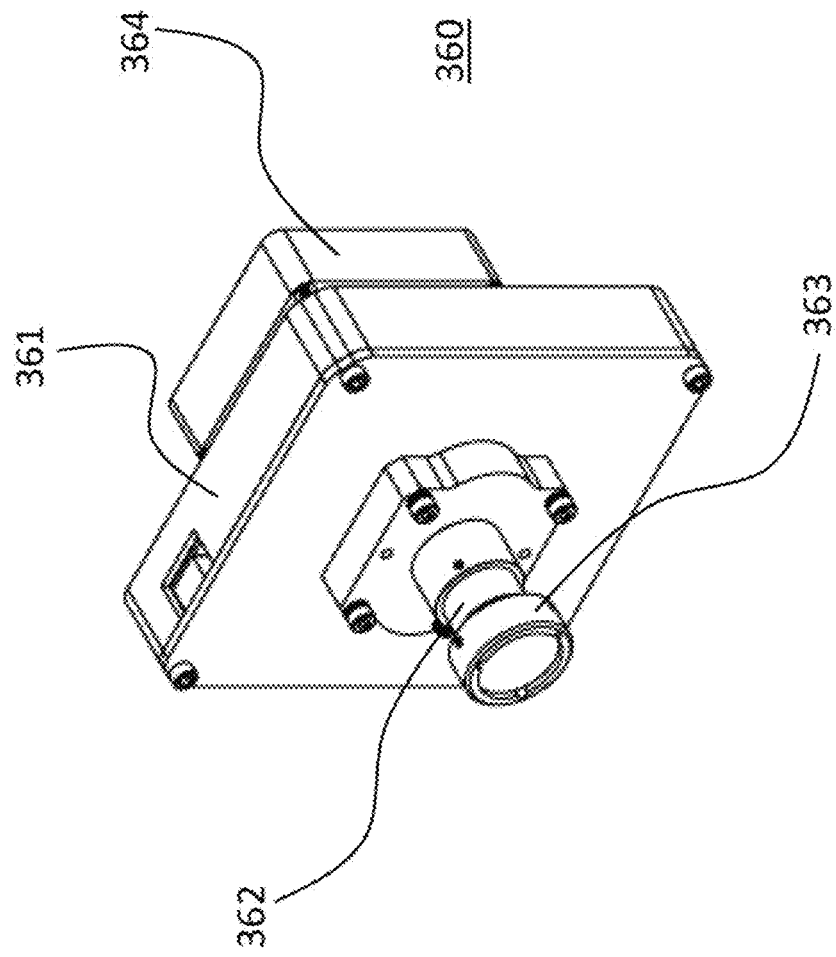
FIG. 51A
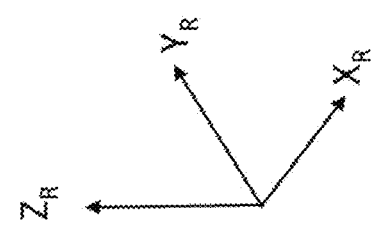

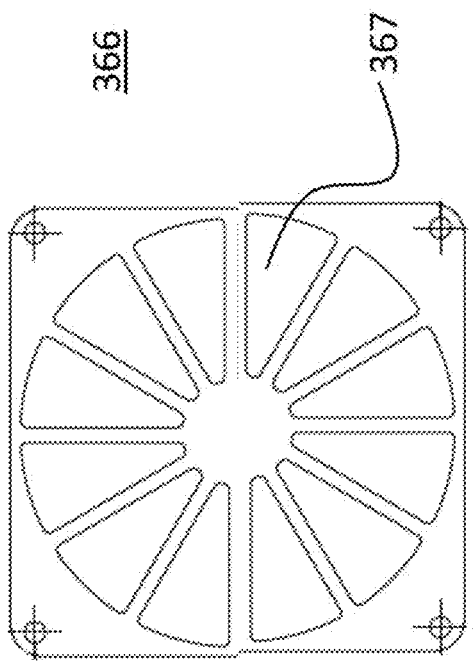
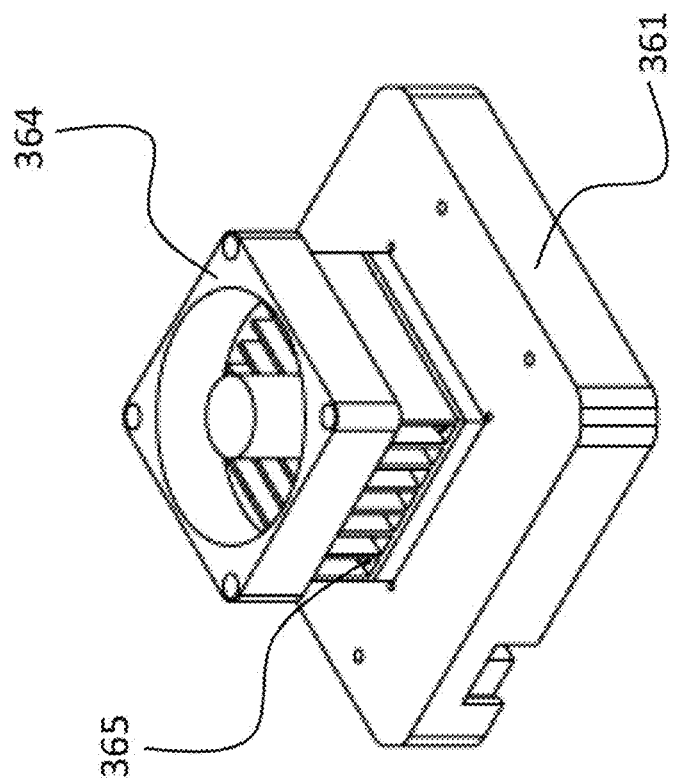

BIOLOGICAL INDICATORS, AND SYSTEMS AND METHODS FOR DETERMINING EFFICACY OF STERILIZATION

BACKGROUND

Several industries require sterilization of certain equipment before that equipment can be reused. One of the largest, and most recognizable, industries with such a requirement is the medical industry, which requires sterilization of various equipment—ranging from surgical instruments to routine medical devices to certain implants—to ensure safety for use. In general, sterilization procedures are designed to kill all viable living organisms within a sterilization chamber. However, sterilization can be challenging, as objects can be contaminated with numerous different types of bacteria, which carry varying levels of danger and difficulty to kill. As such, it is common (and in some industries required) to test the efficacy of each sterilization run to determine if the run successfully sterilized the equipment subjected to the run.

To assess whether a sterilization run was successful (e.g., achieved adequately lethal conditions), sterilization indicators are typically subjected to the sterilization process together with the equipment being sterilized. These sterilization indicators are then analyzed to determine whether the sterilization run associated with the co-processed equipment was successful. One type of sterilization indicator is known as a chemical indicator, which responds to one or more of the critical parameters of a sterilization process and typically either changes color or has a moving front with an endpoint to provide information concerning the sterilization process. Chemical indicators, however, only provide a rough proxy for sterilization success, and therefore may be unreliable.

Another type of sterilization indicator is known as a biological indicator (or "bioindicator"). Biological indicators typically include a population of bacterial spores enclosed in the indicator, which is subjected to the same sterilization run as the equipment being sterilized. Current sterility assurance technologies that make use of biological indicators utilize assays that require at least one day for direct (and at least 20 minutes for indirect) measurements of microorganism survival within the biological indicator. Most of these assays rely on indirect measurement of microorganism survival, and do not quantify the microorganism survival. For example, indirect measurements test for a global change in a specified metric, such as fluorescence, which is then used to determine whether sterility was likely effective. However, the accuracy of such indirect measurements is susceptible to exogenous factors unrelated to the biological changes of interest, which renders these indirect methods less reliable. Additionally, current sterility assurance technologies often rely on these nonquantitative measurements of microorganism survival, and simply return a positive result (indicating microorganism survival and therefore sterilization failure) or a negative result (indicating no detected microorganism survival and therefore sterilization success). And due to the nature of these conventional assays, the positive or negative result can only be returned after the 24 hour (for direct measurement) or 20 minute (for indirect measurement) period.

SUMMARY OF THE INVENTION

According to embodiments of the present disclosure, devices, systems and methods for determining the efficacy of a sterilization process (or "run") enable sterility assurance results to be returned within a fraction of the time currently needed using conventional tools and methods. Aspects of embodiments of the present disclosure are directed to a biological indicator, a process challenge device, and a biological indicator reader having improved accuracy for determining the efficacy of a sterilization process (or "run"). Aspects of embodiments of the present disclosure provide for sterility testing of multiple biological indicators in the biological indicator reader concurrently, allowing for relatively quick sterility assurance with the same equipment. Aspects of embodiments of the present disclosure also provide for a biological indicator and biological indicator reader that provides a direct reading of the presence of live spore(s) in the biological indicator following sterilization.

BRIEF DESCRIPTION OF THE DRAWINGS

The accompanying drawings are included to provide a further understanding of example embodiments of the present disclosure, and are incorporated in, and form a part of this specification. The drawings illustrate exemplary embodiments of the present disclosure and, together with the description, serve to explain principles of the inventive concept(s) of the present disclosure. In the drawings, like reference numerals refer to like elements throughout, unless otherwise specified. In the drawings:

FIG. 12 is an exploded perspective view of a biological indicator (BI) according to embodiments of the present disclosure;

FIG. 16A is a top plan view of the germinant container of FIG. 15;

FIG. 16B is a bottom plan view of the germinant container of FIG. 15;

FIG. 27 is a cross-sectional view of the tray of FIG. 26 taken along the line XXVII-XXVII of FIG. 26;

FIG. 40 is a top perspective view of a second plate of the heater block assembly of FIG. 35;

FIG. 51A is a perspective view of the camera assembly of FIG. 47;

FIG. 52A is a back perspective view of the camera assembly of FIG. 47;

FIG. 52B is a front elevational view of a fan guard of the camera assembly of FIG. 47;

DETAILED DESCRIPTION

Figure 1:
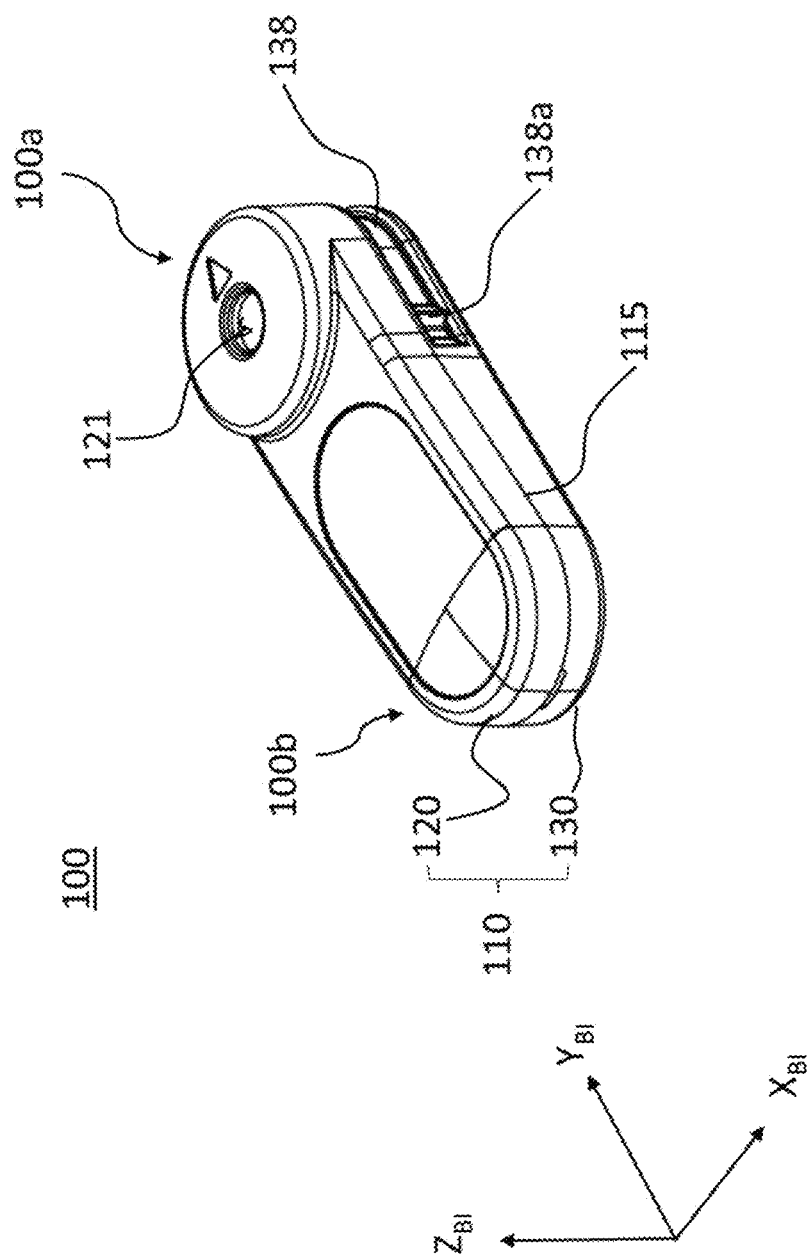
FIG. 1 is a perspective view of a biological indicator (BI) according to embodiments of the present disclosure.

According to embodiments of the present disclosure, biological indicator readers, methods and systems provide accurate determinations of sterilization efficacy within a fraction of the time currently needed using conventional tools and methods. For example, while many conventional sterilization efficacy technologies require 24 hours or longer to provide an indication as to whether a sterilization run was successful, the BI readers, systems and methods according to embodiments of the present disclosure can return an efficacy determination within only several minutes. This represents a dramatic improvement over conventional sterilization efficacy technologies, and allows the equipment subjected to the tested sterilization procedure to be used much sooner than would otherwise be possible using current sterilization efficacy testing technology.

Embodiments of the present disclosure are directed to a system for determining the efficacy of a sterilization process (also referred to herein, interchangeably, as a "sterilization run"). Throughout this disclosure and the accompanying claims, "determining the efficacy of a sterilization process" is used interchangeably with the phrase "sterility assurance," and both terms refer to the same thing, i.e., assessing whether a sterilization process (or run) was successful (e.g., in killing the bacterial spores inside a biological indicator). Aspects of embodiments of the present disclosure are directed to a biological indicator (or "bioindicator" or "BI") 100, a process challenge device (also referred to herein, interchangeably, as a "PCD") 200, and a bioindicator reader (also referred to herein, interchangeably, as a "biological indicator reader" or "BI reader") 300. Aspects of embodiments of the present disclosure are further directed to a method of determining sterilization efficacy utilizing the biological indicator 100 and/or the PCD 200, and the BI reader 300. For example, in some aspects of embodiments of the present disclosure, the method may include subjecting the BI 100 and/or the PCD 200 to a sterilization procedure (or sterilization run), and after completing the sterilization run, inserting the biological indicator 100 into the BI reader 300, which BI reader 300 then tests the biological indicator 100 to determine whether the sterilization run to which the BI was exposed was effective.

Referring to FIGS. 1-12, according to example embodiments, the biological indicator 100 includes a BI housing 110, a germinant container 160, a germinant releaser 170, a spore carrier 180, and an imaging window 190. The BI housing 110 houses the germinant container 160, the germinant releaser 170, and the spore carrier 180. The imaging window 190 allows for imaging of spore activity on the spore carrier 180 by an optical assembly of the BI reader 300, as discussed in greater detail below.

The BI housing 110 is not particularly limited, and may have any suitable shape such that the BI housing 110 may house the germinant container 160, the germinant releaser 170, and the spore carrier 180, and such that the BI housing 110 may be received by the BI reader 300 and, in some embodiments, such that the BI housing 110 may be received by the the PCD 200, as discussed further below. According to embodiments, for example, the BI housing 110 has a substantially obround shape (or stadium shape) in a plan view, and has a BI length $L_{BI}$ along a length direction $Y_{BI}$ thereof that is greater than a BI width $W_{BI}$ along a width direction $X_{BI}$ thereof. The BI length $L_{BI}$ and BI width $W_{BI}$ are not particularly limited, but may be selected to fit within the BI reader 300. For example, in some embodiments, the BI length $L_{BI}$ may be selected such that a user may relatively easily grip the biological indicator 100 at a second end 100b thereof to facilitate insertion of an opposite first end 100a of the biological indicator 100 into the BI reader 300. In some embodiments, for example, the BI length $L_{BI}$ may be approximately 2 to 4 times greater than the BI width $W_{BI}$, for example about 2 to 3 times greater, about 2.5 to 3 times greater, about 2.6 to about 2.9 times greater, or about 2.75 to about 2.8 times greater than the BI width $W_{BI}$.

Referring to FIG. 1, the BI housing 110 may include a first shell (e.g., an upper portion or an upper shell) 120 and a second shell (e.g., a lower shell or a lower portion) 130 that mate together to form the BI housing 110. However, the present disclosure is not limited thereto, and the BI housing 110 may be formed integrally, for example, so long as the contents housed inside of the BI housing 110 can be safely and securely inserted inside the BI housing 110, or the BI housing 110 may be formed of additional components.

In embodiments including mated first and second shells 120 and 130, the configuration and mating profile of the first and second shells 120 and 130 are also not particularly limited, and may be any such configuration or mating profile suitable to securely enclose the contents housed within the BI housing 110. For example, in some embodiments, the first and second shells 120 and 130 may be mated generally along a periphery 115 of the BI housing 110. The periphery 115 may generally equally bisect the thickness of the BI housing. However, in some embodiments, as shown generally in FIGS. 1 and 2, the periphery 115 may be skewed or diagonal relative to the thickness dimension of the BI housing, creating a thinner end 130a and a thicker end 130b of the second (or lower) shell (as shown, e.g., in FIG. 6).

The material of the BI housing 110 is not particularly limited, and may be any material capable of withstanding the sterilization conditions it will be exposed to during the tested sterilization run (e.g., autoclave conditions) and that can safely and securely house the contents of the BI housing 110. Some non-limiting examples for such a material for the BI housing 110 include polypropylene homopolymers, and the like.

Figure 3:
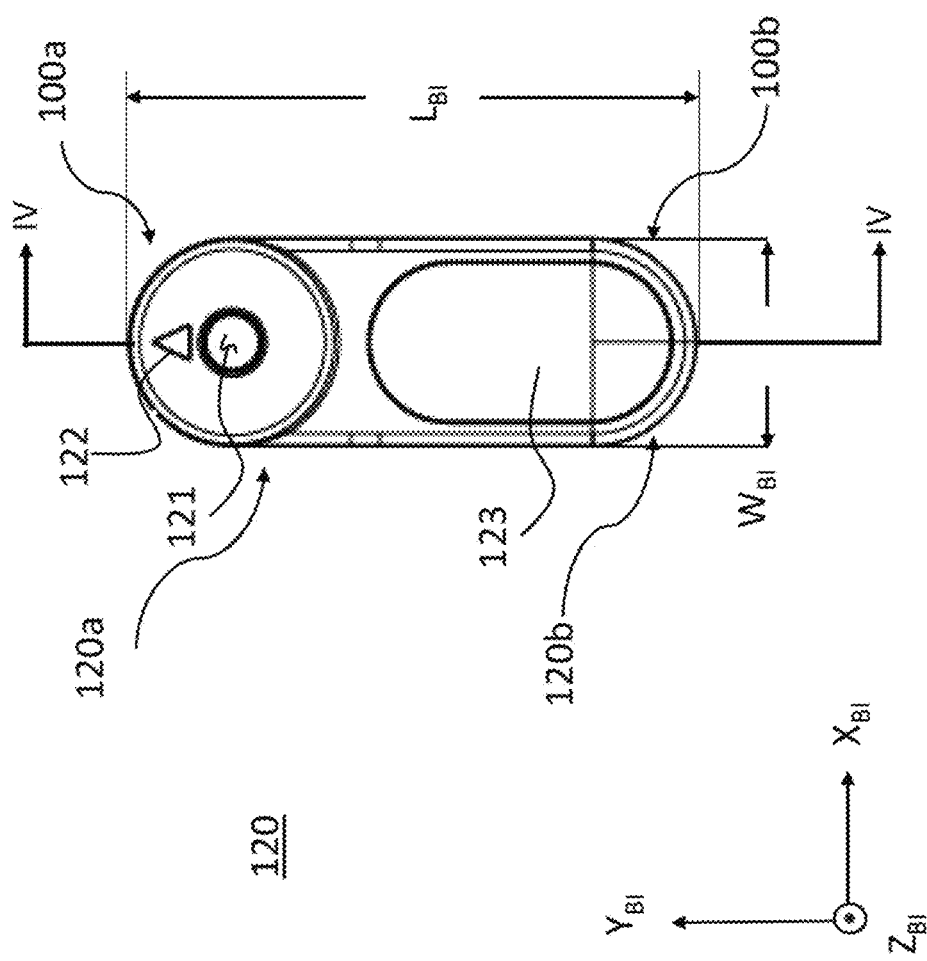
FIG. 3 is a top plan view of a first shell of the biological indicator (BI) of FIG. 1.

Referring to FIG. 3, according to embodiments, the first shell 120 has a grip portion 120b at the second end 100b and extending toward the first end 100a, and a protrusion portion 120a at the first end 100a that protrudes from the grip portion 120b in a thickness direction $Z_{BI}$ of the biological indicator 100 (e.g., the protrusion portion 120a protrudes away from the second shell 130 when the BI housing 110 is assembled). In some embodiments, when viewed in a plan view, the protrusion portion 120a may have a substantially circular shape, but this disclosure is not limited thereto, and the protrusion portion may have any suitable shape such that the BI 100 fits within the BI reader 300. Also, the diameter (or other dimensions) of the protrusion portion 120a may generally correspond to (or be equal to) the BI width $W_{BI}$, but again the present disclosure is not limited thereto, and the protrusion portion 120a may have any suitable dimensions (including those that may extend beyond the BI width $W_{BI}$) so long as the BI fits within the reader. As discussed further below, the protrusion portion 120a (together with the corresponding portion of the second shell 130) defines a cavity inside the BI housing 110 where the germinant releaser 170, at least a portion of the germinant container 160, and the spore carrier 180 are housed.

Figure 4:
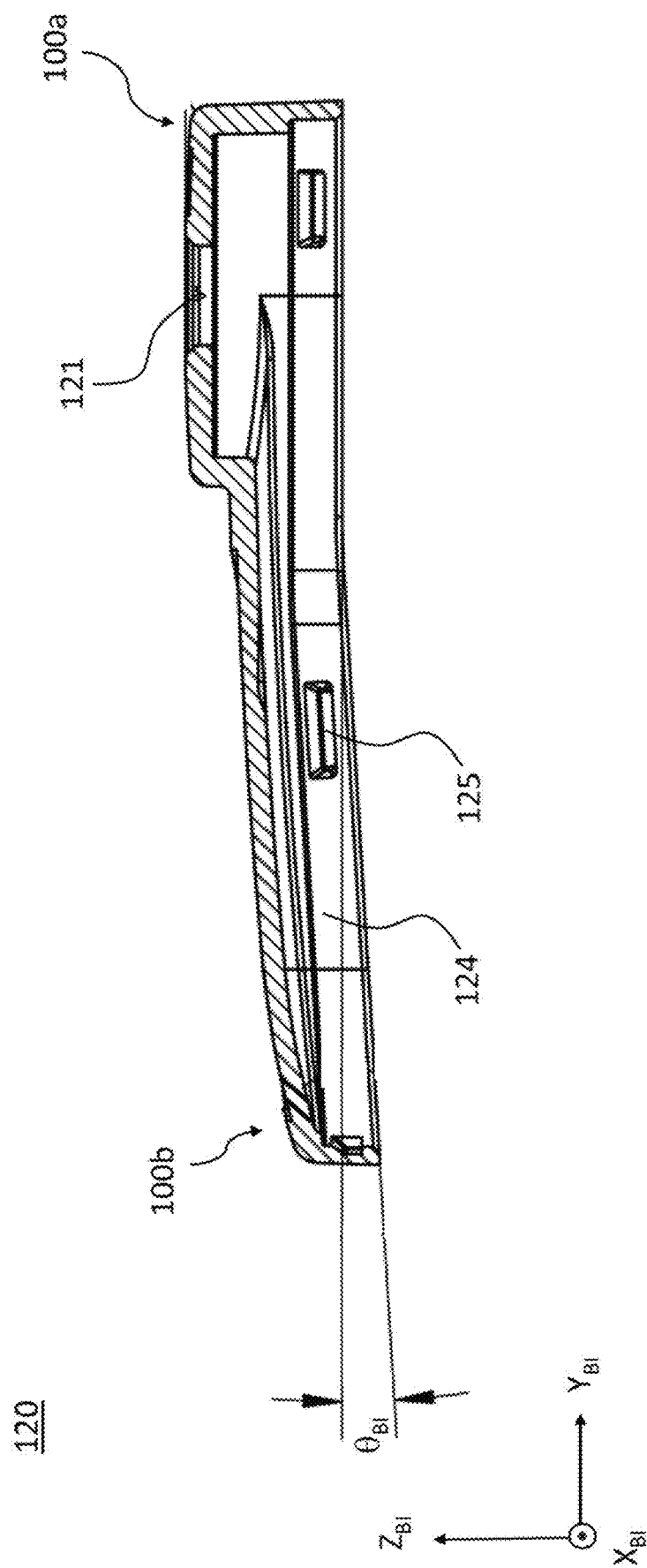
FIG. 4 is a cross-sectional view of the first shell of FIG. 3 taken along the line IV-IV of FIG. 3.

According to embodiments, the protrusion portion 120a may define an opening (e.g., a through hole) 121 that is configured to receive a germinant release lever 401 in the BI reader 300. The opening 121 allows for rupture of the germinant container 160 when the germinant release lever 401 is actuated, as discussed further below. According to embodiments, the opening 121 may be sealed to prevent sterilant entry prior to BI activation. Any suitable sealant material may be used for this purpose, and one non-limiting example of such a sealant includes a foil sealant. Upon activation of the BI, the germinant release lever 401 will break the seal during entry into the opening 121. However, the opening 121 may also remain open (i.e., the seal may be omitted) to allow sterilant to enter the BI housing 110 when the biological indicator 300 is placed in an autoclave chamber, or other sterilization chamber. As shown in FIGS. 1, 3 and 4, the opening 121 is positioned generally at the center of the protrusion portion 120a, but this disclosure is not limited thereto. Indeed, the opening 121 may be positioned anywhere on the protrusion portion so long as the germinant release lever 401 of the BI reader 300 can enter the opening upon actuation, and so long as the position of the opening 121 allows actuation of the germinant release lever 401 to rupture the germinant container 160, as discussed further below.

Figure 6:
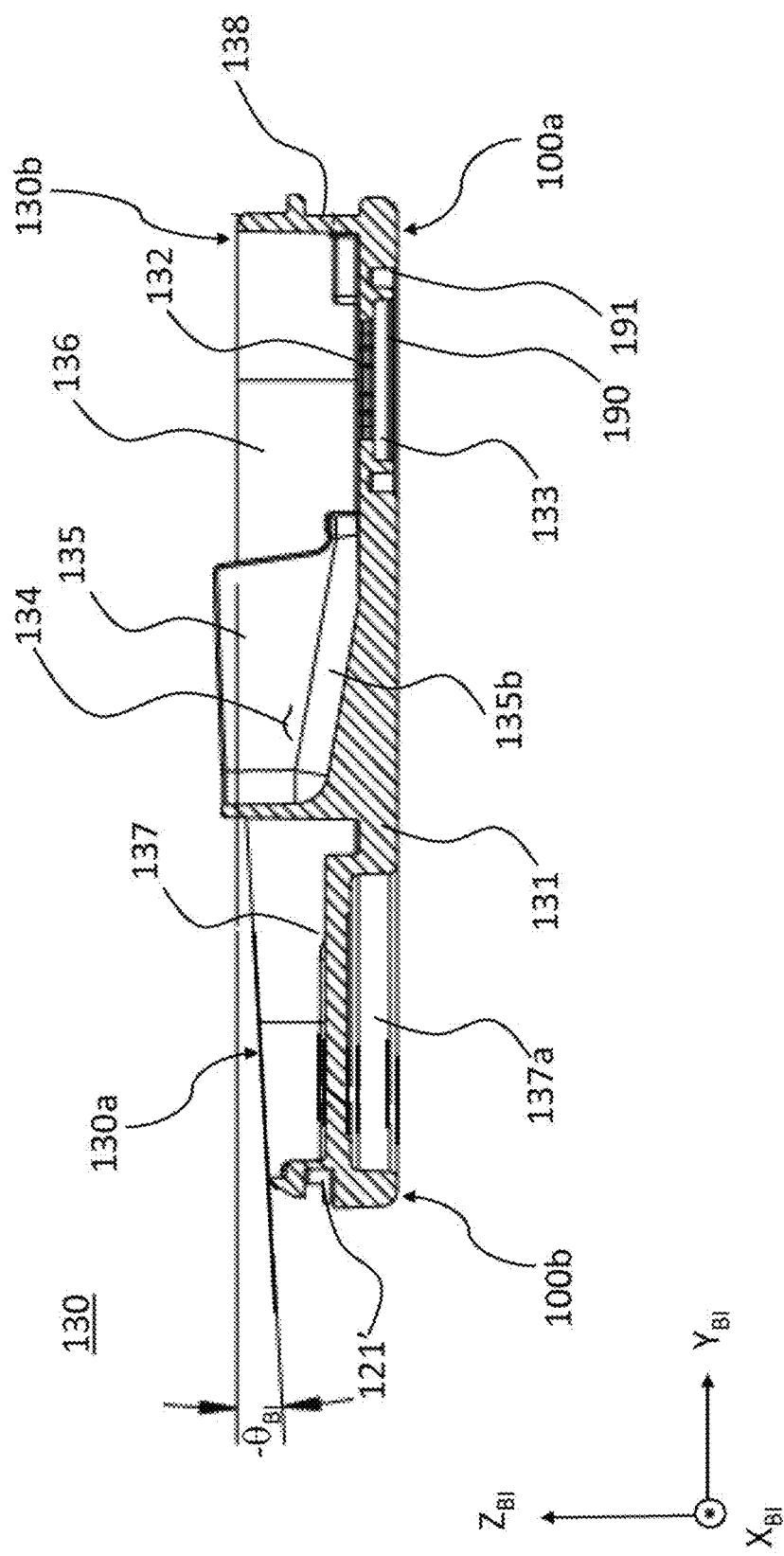
FIG. 6 is a cross-sectional view of the second shell of FIG. 5 taken along the line VI-VI of FIG. 5.

According to embodiments, the opening 121 may be sealed, for example heat sealed with foil (as discussed above), to prevent sterilant from entering through the opening 121. In such embodiments, the BI housing 110 may include a sterilant opening 121' (see FIG. 6) that is separate from the opening 121 and that provides an alternate (or additional) route for the sterilant (e.g., steam) to enter the BI housing 110 during sterilization. The sterilant opening 121' may be positioned in any suitable location on the BI housing 110, including on either the first or second shell 120 or 130. In some embodiments, for example, the sterilant opening 121' may be a through-hole defined in the second end 100b of the BI housing 110, e.g., in the second shell 130 (as shown in FIG. 6). In some embodiments, the sterilant opening 121' may be a through-hole defined in an indentation 137a in the second shell 130, as discussed further below (see FIG. 14). Additionally, while the sterilant opening 121' is discussed here in connection with embodiments in which the opening 121 is sealed against sterilant entry, in some embodiments, the BI may have both an unsealed opening 121 (which allows for sterilant entry) as well as the sterilant opening 121' (which provides as additional avenue for sterilant entry).

According to embodiments, the first shell 120 may further include a visual indicator 122, for example, an arrow or a triangle, which points toward the first end 100a that corresponds to an insertion direction of the biological indicator 100 into the BI reader 300. The grip portion 120b may include a label portion 123 that is configured to receive a label 126 (e.g., a sticker) (see, e.g., FIG. 12) for easily marking and/or labeling the biological indicator 100. The label portion 123 may also have a substantially obround shape with a smaller diameter, but the present disclosure is not limited thereto, and the label portion 123 may have any suitable shape such that a user can add identification information to a surface of the grip portion 120b. According to embodiments, the label portion 123 is untextured (e.g., smooth) such that a sticker may be easily applied and/or removed, and/or such that a user can easily write directly onto the label portion 123. And in some embodiments, the label portion 123 is defined by a recessed portion (or indentation) in the surface of the first shell (as shown generally in FIG. 1). However, it is understood that the label portion 123 may simply be a portion of the surface of the grip portion 120a of the first shell 120, and may not be defined by a visually discernible artifact or disruption in the first shell 120 surface (i.e., the surface of the grip portion 120a of the first shell 120 may be substantially continuous and smooth).

Referring to FIG. 4, according to some embodiments, when the BI housing 120 is assembled, a lower edge of the first shell 120 may be angled relative to the length direction $Y_{BI}$. For example, the top surface of the first shell 120 may form an angle $\theta_{BI}$ relative to the length direction $Y_{BI}$, such that at least a portion of the top surface of the first shell 120 is not parallel to the length direction $Y_{BI}$. In some embodiments, the angle $\theta_{BI}$ relative to the length direction $Y_{BI}$ may be created by the thicker and thinner ends 130a and 130b of the second shell 130, as discussed generally above and in more detail below. In such embodiments, the first shell 120 considered on its own (unmated with the second shell) may have a substantially parallel profile with respect to the length direction $Y_{BI}$, but obtains a non-parallel (or slanted or diagonal) profile when assembled with (or mated to) the second shell.

According to example embodiments, an inner surface 124 of the first shell 120 may include one or more (or in some embodiments, a plurality of) grooves 125 along its periphery that are configured to mate (e.g., securely mate) with corresponding protrusions 139 on a periphery of the second shell 130. However, the mating configuration of the first and second shells 120 and 130 are not limited to this interaction of grooves 125 and protrusions 139, and may instead be any configuration suitable for securely closing the BI housing 110 in a manner that will withstand the conditions of the sterilization process to which it is intended to be exposed. For example, any suitable snap-fit, friction fit, or interference fit engagement between the first and second shells may be used, or the first and second shells may be more fixedly attached to each other, e.g., by an adhesive, or the like.

Figure 5:
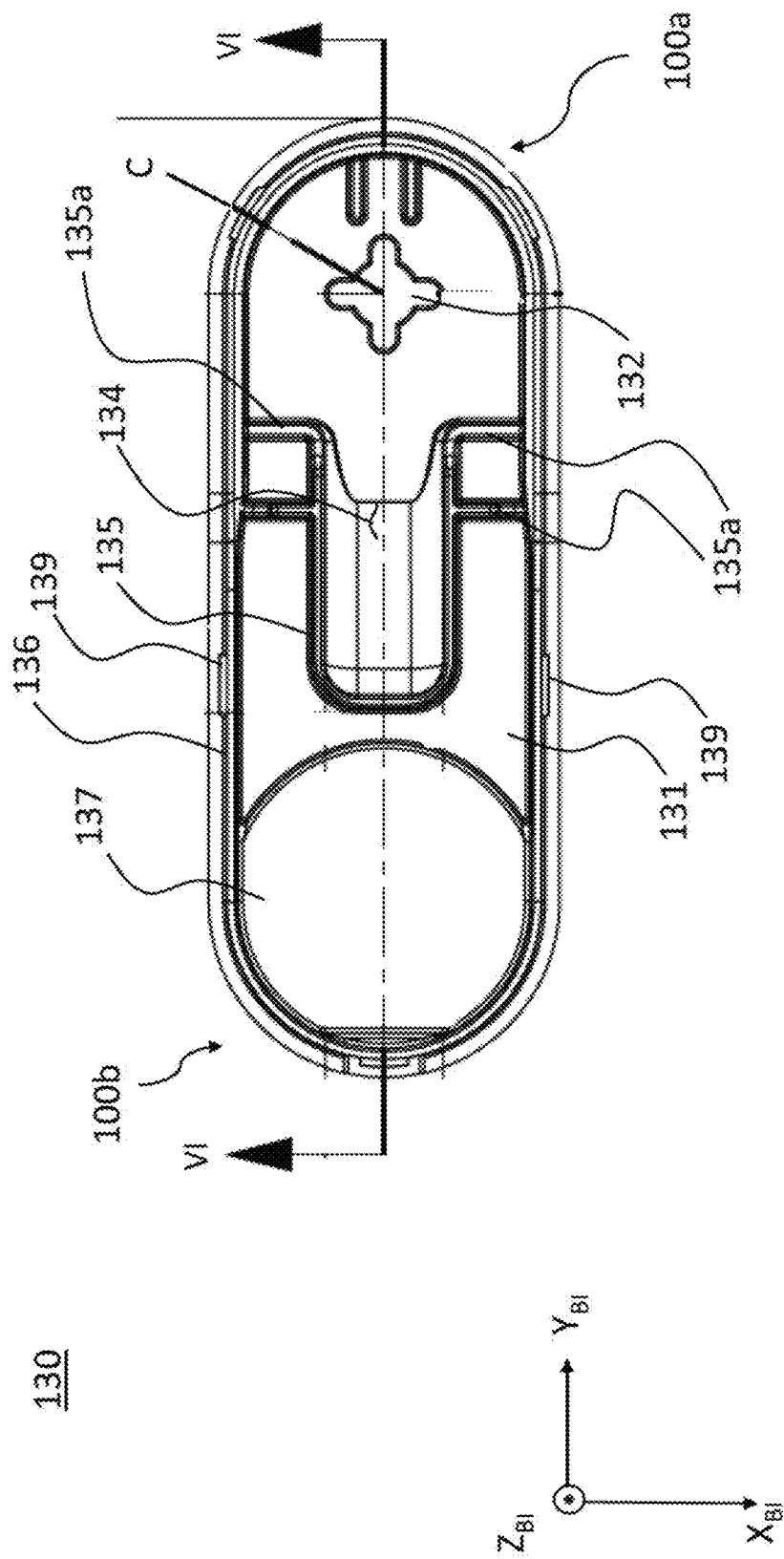
FIG. 5 is a top plan view of a second shell of the biological indicator (BI) of FIG. 1.
Figure 7:
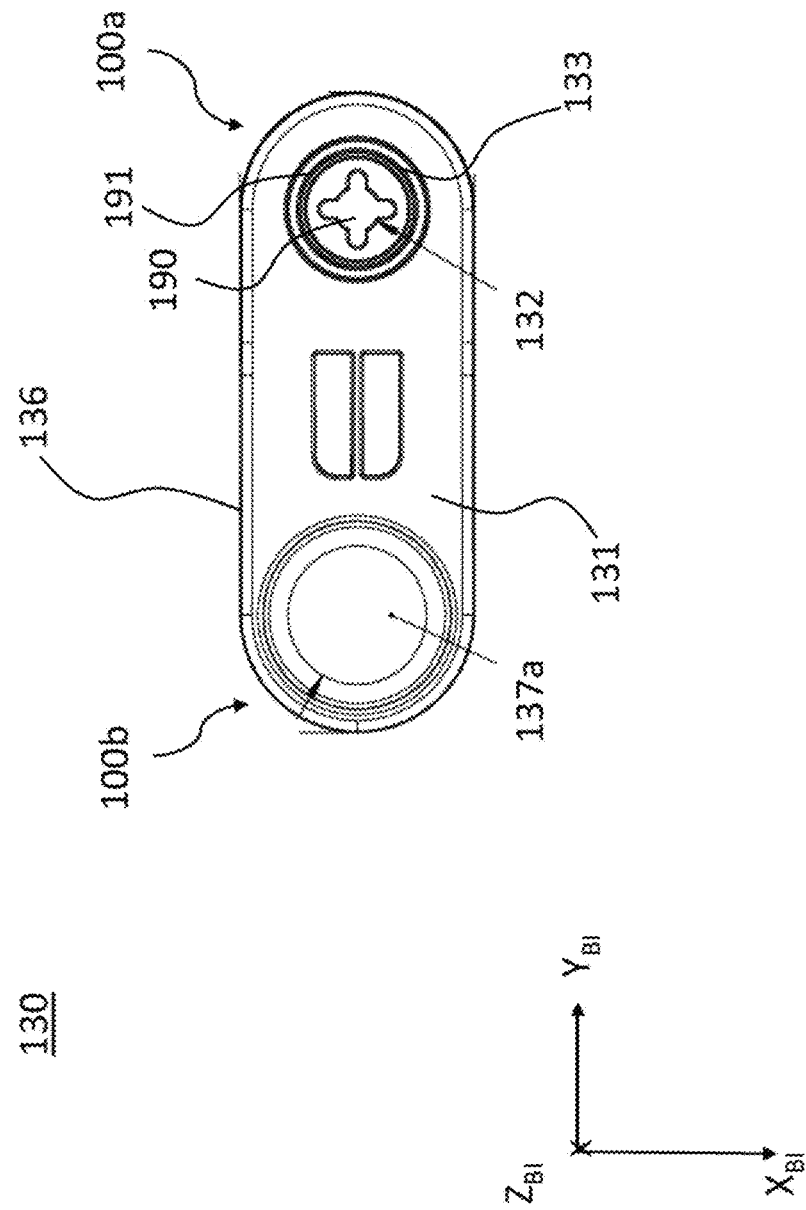
FIG. 7 is a bottom plan view of the second shell of FIG. 5.
Figure 8:
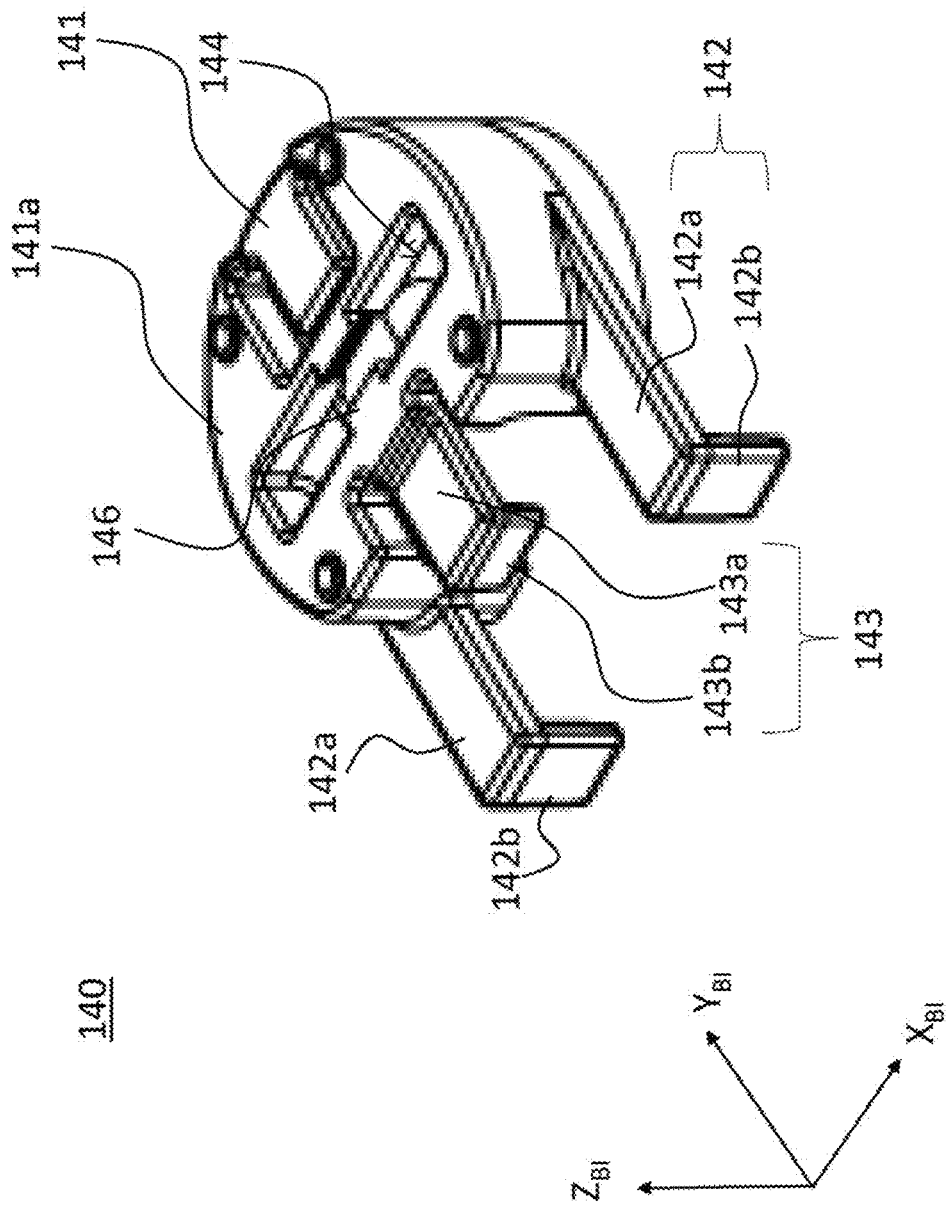
FIG. 8 is a perspective view of a germinant releaser support according to embodiments of the present disclosure.
Figure 9:
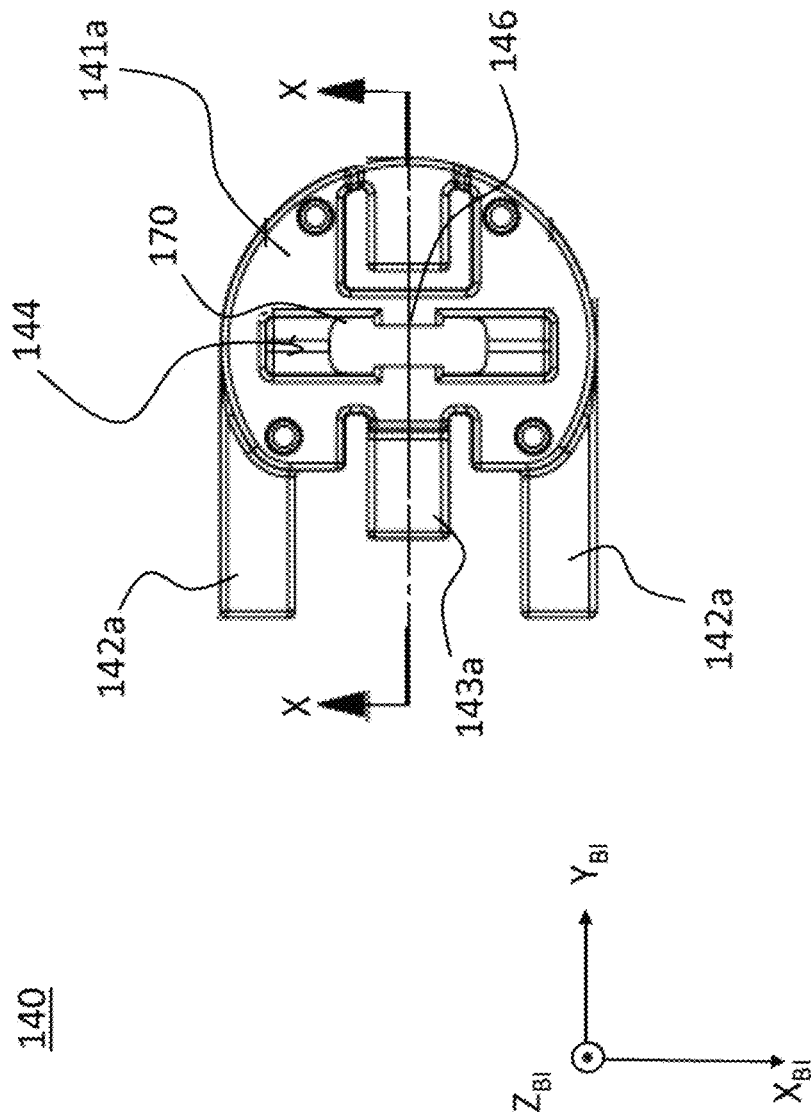
FIG. 9 is a top plan view of the germinant releaser support of FIG. 8.
Figure 10:
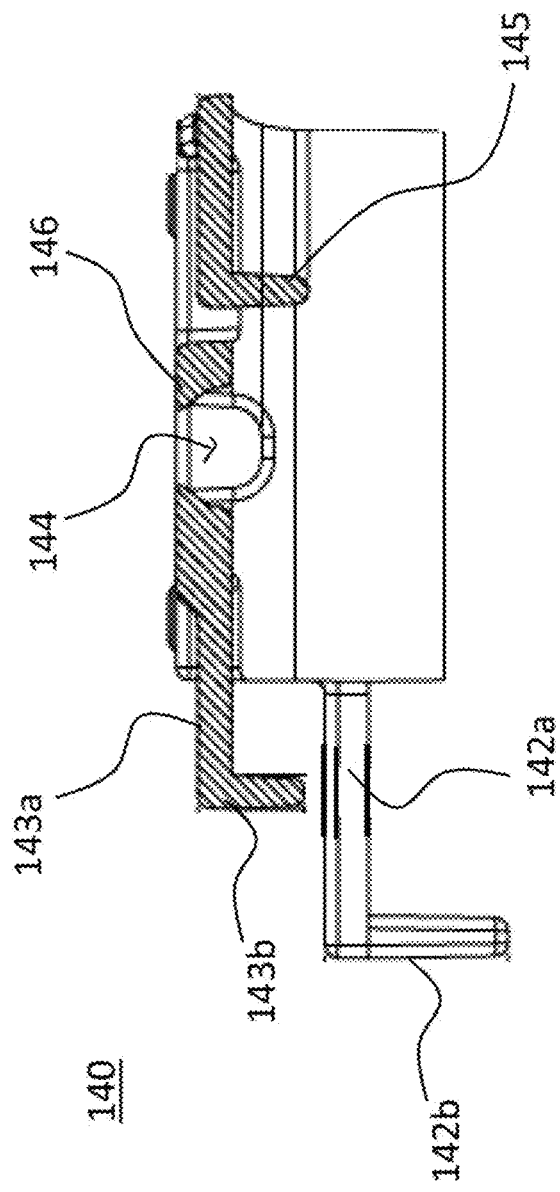
FIG. 10 is a cross-sectional view of the germinant releaser support of FIG. 9 taken along the line X-X of FIG. 9.
Figure 11:
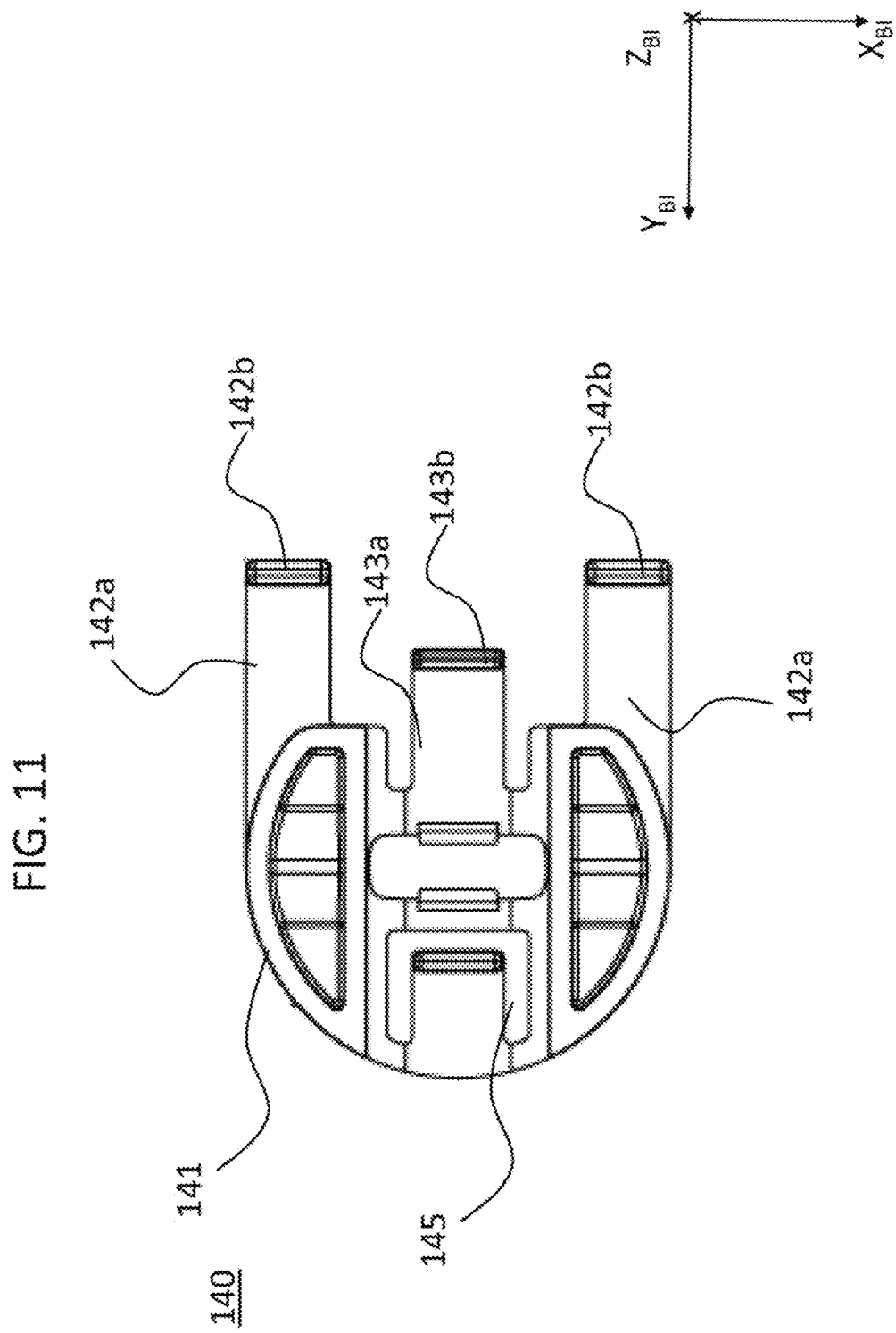
FIG. 11 is a bottom plan view of the germinant releaser support of FIG. 8.
Figure 13:
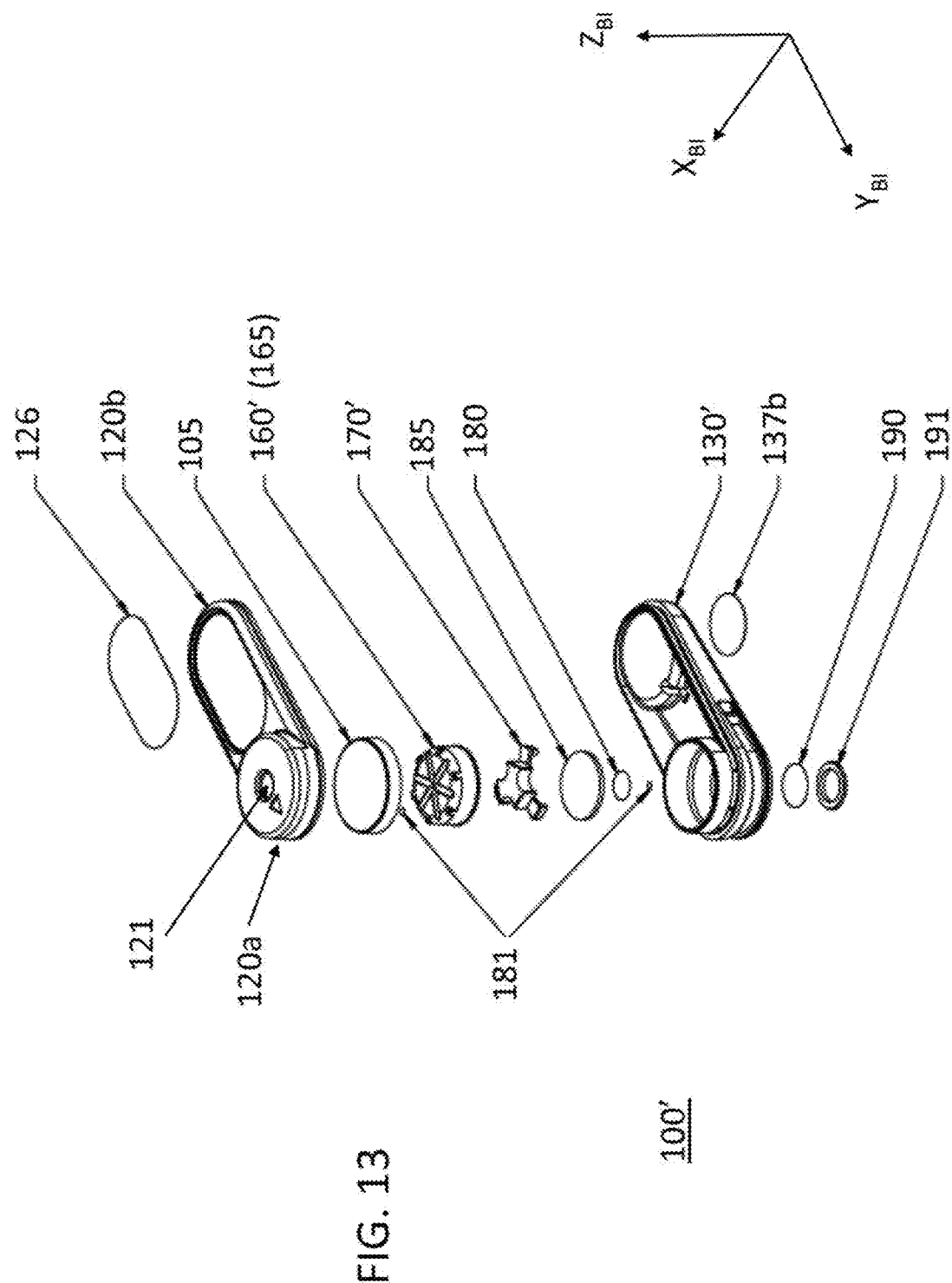
FIG. 13 is an exploded perspective view of a biological indicator (BI) according to embodiments of the present disclosure.

Referring to FIGS. 5-7, according to embodiments, the second shell 130 also has a substantially obround shape when viewed in a plan view. A bottom 131 of the second shell 130 defines a bottom opening (e.g., a through hole) 132, which receives the imaging window 190. The bottom opening 132 is formed in an area of the first end 100a of the biological indicator 100. According to embodiments, when the first shell 120 and the second shell 130 of the BI housing 110 are mated with each other, a center C of the bottom opening 132 is aligned with (e.g., stacked beneath) the opening 121 along the thickness direction $Z_{BI}$. However, it is understood, that the bottom opening 132 is not limited thereto, and may be positioned anywhere on the second shell 130 such that it can receive the imaging window and such that the BI reader 300 can image the spores through the imaging window.

According to embodiments, the bottom opening 132 may have an "Odin's cross" shape, as illustrated in FIGS. 5 and 7. For example, the bottom opening 132 may have a circular portion, with a plurality of protrusions extending from the circular portion, for example four protrusions extending beyond the circular portion in an equilateral cross-shape. However, embodiments of the present disclosure are not limited thereto, and the bottom opening 132 may have any suitable shape. The example Odin's cross shape of the bottom opening 132 may reduce the likelihood of bulging of the spore carrier 180 by allowing air to pass through the protrusion regions, thereby maintaining an equal (or substantially equal) pressure on opposing sides of the spore carrier 180.

Referring to FIG. 7, the bottom 131 of the second shell 130 further includes a window notch 133 that surrounds the bottom opening 132 and is configured to receive the imaging window 190 therein.

According to some embodiments, the imaging window is transparent, such that the bottom opening 132 may remain visible to be used to assist in determining proper alignment of the biological indicator 100 when it is inserted into the BI reader 300. The imaging window 190 may be any suitable material without limitation. Some nonlimiting examples of suitable such materials include thermoplastic polymers, e.g., polymethylpentene, and the like. According to embodiments, the biological indicator 100 may further include a retaining ring 191 which holds the imaging window 190 in the bottom opening 132. The retaining ring 191 may be made of any suitable material without limitation, a non-limiting example of which includes Aluminum 6061. The window notch 133 may have a circular shape, for example, such that the imaging window 190 and the retaining ring 191 may be inserted into the window notch 133 with relative ease. However, the present disclosure is not limited thereto, and the window notch 133 may have any suitable shape. The retaining ring 191 may seal the imaging window 190 to the window notch 133, for example, without creating a hermetic seal but while still preventing airborne organisms from entering the BI housing 110 through the bottom opening 132.

According to embodiments, the second shell 130 may further include a channel 134 which holds the germinant container 160. For example, the channel 134 may be formed near a center of the biological indicator 100 and may have an open end that faces the first end 100a of the biological indicator 100. However, the position of the channel is not limited to this, and may be placed anywhere else in the second shell that is suitable for holding the germinant container 160. In some embodiments, the channel 134 may be defined by a channel wall 135 having a substantially U-shape when viewed in a plan view, which extends away from the bottom 131 of the second shell 130 in the thickness direction $Z_{BI}$. In some embodiments, the channel wall 135 may be formed by creating a pair of grooves extending from the bottom 131, as can be seen in FIG. 7, for example. The channel wall 135 may include one or more connecting portions 135a, which connect the U-shaped channel wall 135 to a side wall 136 of the second shell 130, as illustrated in FIG. 5. In some embodiments, the second shell 130 may include a plurality of connecting portions 135a to enhance stability of the channel wall 135. A channel bottom surface 135b may have a shape that substantially corresponds to a shape of the germinant container 160. For example, the channel bottom surface 135b may have a rounded shape or a chamfered shape which accommodates the germinant container 160, which may have a rounded vial shape. The channel bottom surface 135b may also have a varying thickness, such that the channel bottom surface 135b slopes toward the first end 100a of the biological indicator 100 (see, e.g., FIG. 6).

According to embodiments, the channel wall 135 is angled, which receives the germinant container 160. As such, the germinant 165 may flow downwardly through gravitational forces, further facilitating contact between the germinant 165 and the germinant pad 185.

According to embodiments, the second shell 130 may further include a projection 137 at an area of the second end 100b of the biological indicator 100, located between the side wall 136 and the channel wall 135 along the length direction $Y_{BI}$. The projection 137 may have a circular shape with a diameter that is slightly less than the width $W_{BI}$ of the biological indicator 100, thereby forming the indentation 137a in an outer surface of the bottom 131 of the second shell 130. However, the present disclosure is not limited thereto, and the projection 137 may have any suitable shape and/or may be omitted. According to some embodiments, the indentation 137a may be sized to receive a process indicator 137b that indicates whether the biological indicator 100 has been exposed to a sterilant.

Figure 2:
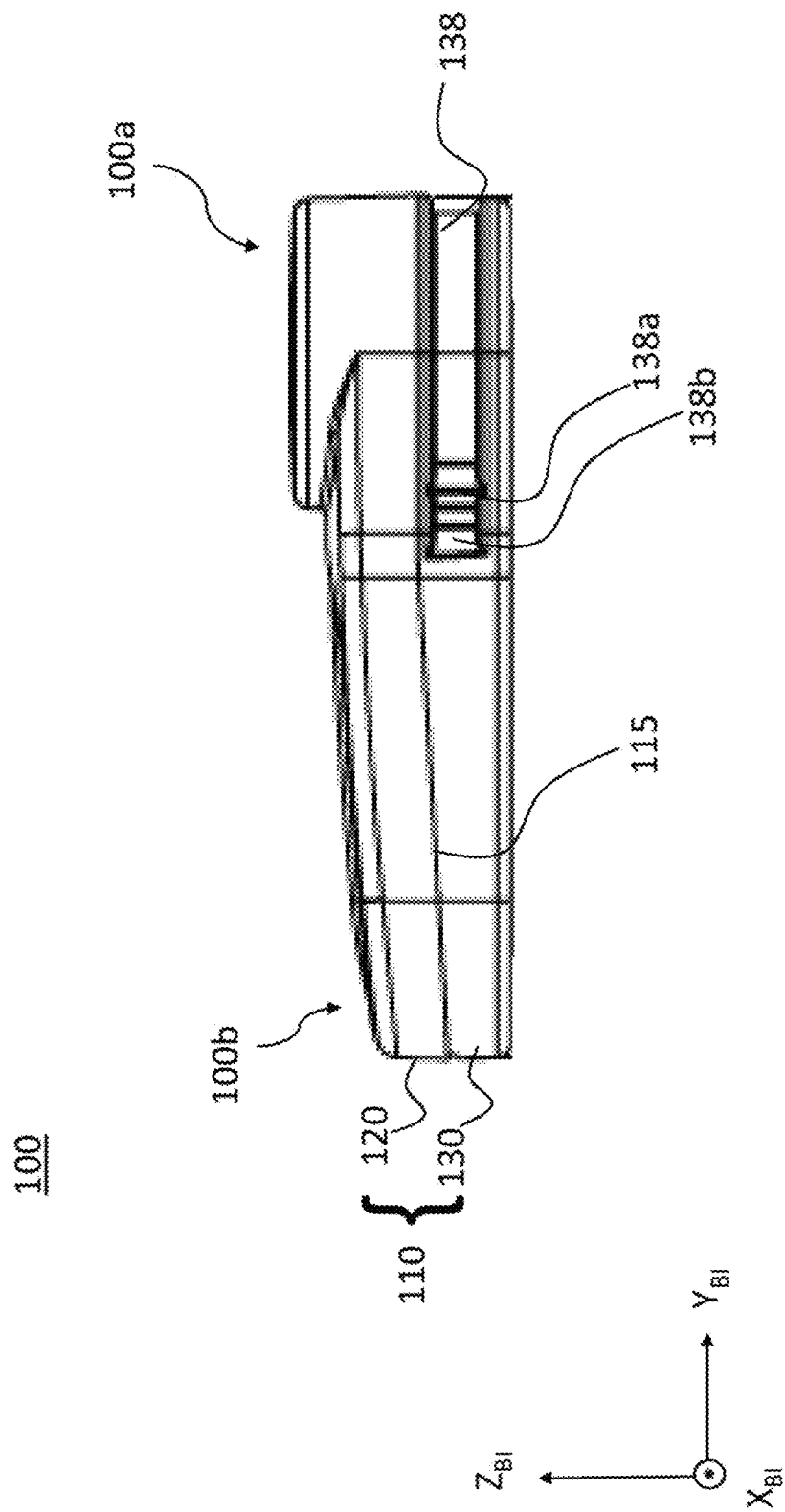
FIG. 2 is a side elevational view of the biological indicator (BI) of FIG. 1.

The second shell 130 further includes a side wall 136 extending from the bottom 131 in the thickness direction $Z_{BI}$. An outward facing surface of the side wall 136 may include an insertion groove 138 at the first end 100a and having a substantially U-shape. The insertion groove 138 is configured to mate with a BI bay 375 and/or a BI latch 384 of the BI reader 300 to facilitate proper insertion of the biological indicator 100 into the BI reader 300. The insertion groove 138 may also include insertion projections 138a at opposite sides of the insertion groove 138 near respective ends of the insertion groove 138, which each define an insertion notch 138b at respective ends of the insertion groove 138, as illustrated in FIG. 2. The insertion projections 138a allow for the BI latch 384 to securely hold the biological indicator 100 in place after insertion into the BI bay 375 of the BI reader 300, for example, by defining the insertion notches 138b which receive a rib 387 of the BI latch 384, and inhibiting removal of the biological indicator 100 while the BI latch 384 is in contact with the biological indicator 100. The insertion groove 138 may wrap around the first end 100a of the biological indicator 100, and may be symmetrical on both sides of the biological indicator 100, though the present disclosure is not limited thereto. According to embodiments, the biological indicator 100 may include the insertion notch 138b and the insertion projection 138a at only one side of the insertion groove 138.

The second shell 130 may further include the protrusions 139 at the outer surface of the side wall 136, which are configured to securely mate with the grooves 125 of the first shell 120. It will be appreciated that, according to embodiments, the grooves 125 may be formed in the second shell 130 and the protrusions 139 may be formed in the first shell 120. Moreover, other means for securely fastening the first shell 120 and the second shell 130 may be used, as are known in the art, and discussed generally above. It will also be appreciated that an upper edge of at least a portion of the side wall 136 may be formed at an angle that is inversely equal to the angle $\theta_{BI}$. In other words, at least a portion of the side wall 136 may be formed at the angle $\theta_{BI}$ below the length direction $Y_{BI}$ such that the first shell 120 and the second shell 130 snugly mate with each other (see, e.g., FIGS. 6 and 2).

According to embodiments, the biological indicator 100 may further include a germinant releaser support 140, which is housed inside the BI housing 110, for example, near the first end 100a of the biological indicator 100, and below the protrusion portion 120a of the first shell 120. The germinant releaser support 140 houses (or accommodates) the germinant releaser 170 and is configured to bring the germinant releaser 170 into contact with the germinant container 160, for example, by application of force in the thickness direction $Z_{BI}$. According to an example embodiment, the germinant releaser support 140 may have a saddle shape.

Referring to FIGS. 8-11, according to some embodiments, the germinant releaser support 140 may include a seat 141, a plurality of support legs 142, a center leg 143, a germinant releaser opening 144, and a tab 155. The seat 141 may have a substantially semicircular shape when viewed in a plan view, with a rounded portion facing the first end 100a of the biological indicator 100. According to embodiments, a width of the seat 141 along the width direction $X_{BI}$ is less than the BI width $W_{BI}$. As such, the germinant releaser support 140 may easily be installed in the BI housing 110 without interference with the BI housing 110.

The support legs 142 may each include an extension portion 142a that extends away from the seat 141 along the length direction $Y_{BI}$ toward the second end 100b, and a projection portion 142b that extends from an end of the extension portion 142a opposite to the seat 141, and extends downwardly in the thickness direction $Z_{BI}$. The support legs 142 may be formed at opposite ends of the seat 141 along the width direction $X_{BI}$, such that the support legs 142 straddle the channel 134 and the germinant container 160 when the biological indicator 100 is assembled. In addition, the support legs 142 may be offset from an upper surface 141a of the seat 141 in the thickness direction $Z_{BI}$. The projection portions 142b are configured to extend past ones of the connecting portions 135a when the germinant releaser support 140 is inserted into the BI housing 110, thereby maintaining the relative placement of the germinant releaser support 140. According to embodiments, the support legs 142 are located at a height on the seat 141 such that the extension portions 142a may rest on an upper surface of the connecting portions 135a. As discussed above, this configuration allows for relatively easy placement and alignment of the germinant releaser support 140, without requiring a clearance fit or a tight fit, which can cause issues and delays during production, and which would limit flexibility of the germinant releaser support 140 when a downward force is applied to the germinant releaser support 140.

The center leg 143 may include a center leg extension portion 143a and a center leg projection portion 143b. The center leg 143 may be located at a generally central portion of the seat 141 along the width direction $X_{BI}$ such that the center leg 143 is located above the channel 134 and the germinant container 160 when the biological indicator 100 is assembled. However, the present disclosure is not limited to this, and the center leg 143 may be positioned anywhere on the germinant releaser support 140 so long as the center leg 143 remains capable of contacting the germinant container 160, as discussed further below. The center leg extension portion 143a may extend away from the seat 141 along the length direction $Y_{BI}$, and may have a length in the length direction $Y_{BI}$ that is less than a length of the support legs 142 along the length direction $Y_{BI}$. The center leg 143 is configured to be positioned above the germinant container 160 when the germinant container 160 and the germinant releaser support 140 are inside the BI housing 110. The center leg projection portion 143b extends downwardly in the thickness direction $Z_{BI}$, and is configured to contact the germinant container 160 when force is applied to the germinant releaser support 140 (e.g., upon actuation of the germinant release lever 401 of the BI reader 300), acting as a spring to concentrate the downward force of the germinant releaser 170 onto the germinant container 160, as discussed further below.

The germinant releaser support 140 may be made of any suitable material such that the support legs 142 allow for flexible movement of the germinant releaser support 140 along the thickness direction $Z_{BI}$. For example, the germinant releaser support 140 may be formed of a polymeric material (nonlimiting examples of which include polypropylenes, and the like), which has sufficient give to allow for movement of the seat 141 when downward pressure is applied (along the thickness direction $Z_{BI}$), but sufficient strength to maintain the support legs 142 in their position relative to the channel 134.

According to embodiments, the germinant releaser support 140 further includes a tab 145 which protrudes downwardly from the seat 141. When the BI is in the non-activated state, the center leg projection portion 143b and the tab 145 are spaced vertically from the surface of the germinant container 160. As discussed above, when the BI is activated (i.e., upon actuation of the germinant release lever 401 of the BI reader 300), the force applied by the germinant release lever 401 overcomes the spring force of the support legs 142, which, in turn causes the center leg projection portion 143b and the tab 145 to come into contact with the germinant container 160. Upon this contact, each of the center leg projection portion 143b and tab 145 act as a spring to concentrate the downward force of the germinant releaser 170 onto the germinant container 160 (e.g., across a diameter of the germinant container).

The seat 141 further defines a germinant releaser opening 144 that is configured to receive the germinant releaser 170 and to maintain positioning between the germinant releaser 170 and the germinant releaser support 140. For example, the germinant releaser opening 144 may have a substantially cylindrical shape with a length along the width direction $X_{BI}$. According to embodiments, the length of the germinant releaser opening 144 is greater than a width of the germinant container 160 along the width direction $X_{BI}$ to ensure that the germinant releaser 170 contacts the germinant container 160 upon actuation of the germinant release lever 401 of the BI reader (discussed further below). The germinant releaser opening 144 may include one or more (or a plurality of) stops 146 extending toward each other along the length direction of the germinant releaser opening 144. The stops 146 serve to prevent the germinant releaser 170 from exiting the germinant releaser opening 144 above the seat 141 when downward pressure is applied to the germinant releaser support 140. Stated differently, the stops 146 serve to maintain the germinant releaser 170 in the germinant releaser opening 144 upon actuation of the germinant release lever 401 of the BI reader 300 (discussed further below), which ensures that the germinant releaser 170 contacts the germinant container 160 with enough force to rupture or break the germinant container 160.

After the biological indicator 100 is inserted into the BI bay 375, the germinant release lever 401 is activated, causing it to extend into the opening 121 of the biological indicator 100 and apply downward pressure onto the components inside of the biological indicator 100. More specifically, the germinant release lever 401 presses downwardly onto the germinant releaser support 140 (directly or via the sterilant membrane 105), which presses downwardly toward the bottom 131. The germinant releaser support 140 flexes downwardly, bringing the germinant releaser 170 into contact with the germinant container 160, thereby rupturing the germinant container 160 and releasing the germinant 165 into the BI housing 110. The germinant 165 flows downwardly toward a germinant pad 185, which captures (e.g., absorbs) the germinant 165, directing (e.g., wicking) the germinant 165 through the germinant pad toward the spore carrier 180. If the sterilization process was successful, the spores 181 on the spore carrier 180 were killed during the sterilization process, at which point the spores released DPA. The DPA from these dead spores may be bound by the photoluminescent component of the germinant and generate a static background level of DPA that is detected by the BI reader 300. However, if any of the spores on the spore carrier remain viable after completion of the sterilization process, those spores will germinate upon contact with the germinant compound, and will release DPA upon germination. Once the DPA is released from these viable spores, the DPA will be bound by the photoluminescent component, and detected by the BI reader 300 as a DPA signal above the static background level (when such a background signal is present). This detection and distinction between DPA signals is discussed in further detail below.

According to some embodiments, the biological indicator 100 may further include the germinant pad 185. The germinant pad 185 may be a wicking layer that is located below the germinant container 160. The germinant pad 185 may include any material capable of wicking a germinant (e.g., a germinant fluid) 165 that is expelled from the germinant container 160 after the germinant container 160 is ruptured. Nonlimiting examples of suitable such wicking materials include cotton and cellulose-based materials, and any other wicking materials known to those of ordinary skill in the art.

Upon rupture of the germinant container 160, the germinant 165 released from the germinant container 160 transports (or wicks) through the germinant pad 185 to a spore carrier 180 located below the germinant pad 185. The wicking (or transporting) function of the germinant pad 185 is generally provided by the material of the germinant pad 185, which as noted generally above, may be any material suitable for wicking or transporting a fluid having the composition and properties of the germinant solution, e.g., by capillary-like action. The germinant pad 185, therefore, provides a relatively controlled delivery of the germinant 165 through the germinant pad 185 to the spore carrier 180.

The germinant pad 185 may have any suitable shape and size without limitation so long as it is capable of transporting the germinant 165 through the pad to the spore carrier 180. In some embodiments, for example, as shown in FIG. 12, the germinant pad 185 may have a generally rectangular shape. As shown, the germinant pad 185 may have an area (i.e., width×length) greater than the area of the spore carrier 180 to ensure that the germinant 165 is delivered efficiently and in sufficient amount to the spore carrier 185. Additionally, in some embodiments, the greater area of the germinant pad 185 allows the germinant pad to maintain any rogue pieces of the broken germinant container 160 and keep those pieces from contaminating the spore carrier 180. In furtherance of that end, in some embodiments, the germinant pad 185 may also include a protrusion from a generally rectangular main body, which protrusion is configured to fit in the channel 134 holding the germinant container 160. And in embodiments in which the germinant pad 185 is not generally rectangular in shape, the germinant pad 185 may have any other shape with at least a portion extending into the channel 134.

The spore carrier 180 may include any support material capable of housing bacterial spores 181. The spores 181 may be any bacterial spores 181 suitable for use to determine the efficacy of a sterilization process. The bacterial spores selected to determine the efficacy of sterilization may differ depending on the type of sterilization process being tested. In general, highly resistant bacterial species are selected since these species are particularly difficult to kill, and therefore provide a more accurate assessment of sterilization efficacy. Traditionally, bacteria of the genera *Geobacillus* and *Bacillus* have been used due to their high resistance to sterilization, e.g., steam sterilization. Accordingly, the spores 181 on the spore carrier 180 may include a bacteria from these genera, but the present disclosure is not limited thereto, and any bacterial spores known for use in determining sterilization efficacy may be used without limitation, e.g., those of the genus *Clostridium*.

The spores 181 may be applied to the spore carrier 180 by any suitable means and methods, without limitation. According to embodiments, for example, the bacteria may be suspended in an alcohol (e.g., ethanol or 40% ethanol), and the spores 181 may include a spore population of between about $1.0 \times 10^7$ spores/0.1 ml to about $3.0 \times 10^7$ spores/0.1 ml. The spores 181 may have a D-Value Range of between about 1.9 to about 2.1 minute D-Value at 121 C steam. According to embodiments, approximately 200,000 spores 181 may be applied to the spore carrier 180, and in some embodiment, at least 100,000 spores 181 are applied to the spore carrier 180. According to embodiments, the spores 181 are applied to a bottom surface of the spore carrier 180 (or a surface of the spore carrier 180 facing the imaging window 190) so that the germinant 165 reaches the spores 181 after saturating the spore carrier 180. This prevents the flow of germinant 165 from oversaturating the spores 181, which may affect the readings by the BI reader 300.

The spore carrier 180 may be formed of any suitable material with sufficient porosity and density such that the spores 181 do not pass through the spore carrier 180, and such that the spore carrier 180 withstands the high temperatures encountered during the sterility procedure (e.g., an autoclave procedure). For example, the spore carrier 180 may have a pore size of approximately 0.1 to about 0.8 µm, about 0.2 to about 0.4 µm, or about 0.3 µm. According to embodiments, the spore carrier 180 may have a gray or black color to enable improved background correction during testing of the biological indicator 100, as discussed further below. Any suitable dye may be used to color the spore carrier 180 gray or black so long as the dye is not cytotoxic. Non-limiting examples of suitable spore carrier materials include cellophane-based materials, such as poly-cellophane materials, polyester materials (such as, e.g., polyethylene terephthalate), and the like.

Any of the spores 181 that were killed during the sterilization procedure released dipicolinic acid (DPA). The DPA released by these dead spores 181 may diffuse into a background DPA level that may be detected via an optical assembly of the BI reader 300 (discussed further below). In some embodiments, if the early DPA readings by the BI reader match expected levels based on the known bacterial spore population on the carrier, this provides an early indication that the spores inside the BI were sufficiently exposed to the sterilant during the sterilization procedure. Conversely, if the early DPA readings show an absence of DPA or DPA releases lower than the anticipated threshold, this may indicate that the sterilization process failed, or that the spores inside the BI were not sufficiently exposed to the sterilant. If any of the spores 181 remain viable after sterilization, the viable spores 181 will germinate upon exposure to the germinant 165 and release their DPA, resulting in time-lapsed DPA spikes indicative of spore germination (and thus spore survival) and sterilization failure. This is discussed in further detail below.

The shape and size of the spore carrier 180 is not particularly limited, and may be any shape and size suitable to hold the population of bacterial spores 181. However, in some embodiments, the spore carrier is not larger than the imaging window 190 so that the entire spore carrier can be imaged by the BI reader 300 and analyzed on a pixel-by-pixel basis, as discussed further below. According to some embodiments, for example, the spore carrier 180 may have a disc shape that generally corresponds in size and shape to the imaging window 190. According to embodiments, the spores 181 are deposited on the spore carrier 180 such that the spores 181 are centered in the bottom opening 132 so that an optical assembly of the BI reader 300 may be aligned to a center of the bottom opening 132 (and therefore to a location of the spores 181). The spores 181 are deposited on the spore carrier 180 according to any suitable method. For example, the spores 181 may be deposited on the spore carrier 180 while suspended in a liquid and by applying a vacuum to extract fluid during deposition of the spores 181, thereby creating a dry deposition of the spores 181 on the spore carrier 180. As such, the likelihood of the spores 181 moving on the spore carrier 180 after deposition is reduced. According to some embodiments, the spore carrier 180 may be pre-treated to improve hydrophilicity. As such, the germinant solution 165 may be more effectively transported to the spores 181, and the likelihood of imaging artifacts may be reduced. Examples of suitable hydrophilicity treatments include UV exposure, plasma oxygen, or the like, but the present disclosure is not limited thereto.

As noted generally above, the germinant container 160 houses a germinant (or germinant solution or liquid) 165. The material and construction of the germinant container 160 is not particularly limited so long as it can hold the germinant solution 165, withstand the conditions of the sterilization process (e.g., the high heat and steam of an autoclave), and can be broken or ruptured by the germinant releaser 170 upon actuation by the reader 300. Those of ordinary skill in the art would be capable of selecting an appropriate such material, but one non-limiting example includes glass.

According to some embodiments, the germinant container 160 may be an ampule (or ampoule) made of glass. The germinant container 160 has any suitable thickness such that the germinant container 160 contains the germinant 165 during the sterilization cycle (e.g., an autoclave cycle), and that the germinant container 160 ruptures when pressure is applied to the germinant container 160 by the germinant releaser 170. According to one or more embodiments, the germinant releaser 170 may be a dowel comprising metal, ceramic, or the like, though the present disclosure is not limited thereto. The germinant releaser 170 (e.g., as a dowel) may have a length in the width direction $X_{BI}$ that is greater than a width of the germinant container 160 in the width direction $X_{BI}$ to increase the likelihood that the germinant releaser 170 ruptures the germinant container 160. According to example embodiments, the germinant releaser 170 may have a spherical shape (such as a BB), or any other suitable shape and density that allows for rupture of the germinant container 160.

According to embodiments, the biological indicator 100 may further include a gauze or other wrap provided around the germinant container 160, which helps collect broken pieces of the germinant container 160 (e.g., glass pieces of the ampule) that are created by rupturing the germinant container 160.

The germinant solution 165 is housed inside the germinant container 160 such that the germinant solution 165 is not exposed to the sterilization conditions of the sterilization process (e.g., is not exposed to the steam produced in an autoclave). The germinant solution contains at least a germinant compound and a photoluminescent component, and may further contain a solvent, e.g., water. According to embodiments, a surfactant, such as sodium dodecyl sulfate (SDS) may be added to the germinant solution 165, which further improves hydrophilicity of the spore carrier 180 upon exposure to the germinant solution 165. The germinant compound is not particularly limited, and may be any compound capable of inducing germination of the bacterial spores 181 carried on the spore carrier 180. Those of ordinary skill in the art would be capable of selecting an appropriate such germinant compound, e.g., based on the type of bacterial spores carried on the spore carrier. Non-limiting examples of suitable germinants includes L-alanine, potassium combined with one or more simple sugars, and a combination of valine and isoleucine.

The photoluminescent component is also not particularly limited, but should be a component suitable to cause or enhance the photoluminescence of the DPA expelled by the bacterial spores in the visible light range, thereby improving the detectability of released DPA by the BI reader 300. Non-limiting examples of suitable such components include lanthanide complexes, e.g., complexes including a lanthanide ion and a counter-ion. As would be understood by those of ordinary skill in the art, "lanthanides" encompass elements 57-71 of the periodic chart, i.e., La, Ce, Pr, Nd, Pm, Sm, Eu, Gb, Tb, Dy, Ho, Er, Tm, Yb, and Lu. In some embodiments, the lanthanide ion of the photoluminescent compounds may include La, Ce, Eu or Tb, for example, Eu or Tb, and in some embodiments, the lanthanide ion may be Tb. Those of ordinary skill in the art are capable of selecting an appropriate anion for the lanthanide complex, but some nonlimiting examples include halides (e.g., chlorides, fluorides, bromides or iodides). In some embodiments, for example, the anion may be a chloride. For example, in some embodiments the photoluminescent component includes terbium chloride hexahydrate. It will be appreciated by those of ordinary skill in the art that the methods, systems, and apparatuses, including the germinant solution compositions, disclosed in U.S. Pat. No. 7,306,930 to Ponce et al. titled "Method bacterial endospore quantification using lanthanide dipicolinate luminescence," U.S. Pat. No. 7,608,419 to Ponce titled "Method and apparatus for detecting and quantifying bacterial spores on a surface," U.S. Pat. No. 7,611,862 to Ponce titled "Method and apparatus for detecting and quantifying bacterial spores on a surface," U.S. Pat. No. 9,469,866 to Ponce titled "Method and apparatus for detecting and quantifying bacterial spores on a surface," U.S. patent application Ser. No. 15/283,268, which is currently pending, to Ponce titled "Method and apparatus for detecting and quantifying bacterial spores on a surface," and U.S. Pat. No. 9,816,126 to Ponce titled "Method and apparatus for detecting and quantifying bacterial spores on a surface," U.S. Pat. No. 7,563,615 to Ponce titled "Apparatus and method for automated monitoring of airborne bacterial spores," U.S. patent application Ser. No. 10/355,462 to Ponce et al., now abandoned, titled "Methods and apparatus for assays of bacterial spores," U.S. Pat. No. 8,173,359 to Ponce et al. titled "Methods and apparatus and assays of bacterial spores," U.S. patent application Ser. No. 13/437,899 to Ponce et al., now abandoned, titled "Methods and apparatus for assays of bacterial spores," U.S. Pat. No. 10,612,067 to Ponce et al. titled "Methods and apparatus for assays of bacterial spores," U.S. patent application Ser. No. 16/841,534 to Ponce et al. titled "Methods and apparatus for assays of bacterial spores," each of which is incorporated herein by reference in its entirety, may also be utilized.

According to some embodiments, the biological indicator 100 may also include a sterilant membrane 105 that is located between the protrusion portion 120a of the first shell 120 and the germinant releaser support 140. The sterilant membrane 105 is sterilant permeable (e.g., steam permeable) to allow the sterilant access to the interior of the BI 100. The material of the sterilant membrane 105 is not particularly limited so long as it is permeable to the sterilant. Non-limiting examples of suitable sterilant membrane materials include cellulose-based papers and Kraft paper, e.g., 40 pound Kraft paper. The sterilant membrane 105 may have any suitable shape and size, without limitation. In some embodiments, for example, the sterilant membrane may have a generally circular shape, and may be configured to fit inside the protrusion portion 120a of the first shell 120. According to embodiments, the sterilant membrane 105 may be omitted.

According to some embodiments, the biological indicator 100 may further include a secondary spore carrier and secondary spores at a second location separate from the spore carrier 180. The secondary spores are also exposed to the sterilant when the biological indicator 100 undergoes a sterilization process. However, unlike the spores 181 on the spore carrier 180, the secondary spores are not exposed to the germinant 165 when the biological indicator 100 is activated in the BI reader 300, and can instead be used in a reference culture test to verify the results obtained from the BI reader 300. According to embodiments, the secondary spores may be located outside of the channel wall 135, e.g., between the channel wall 135 and the side wall 136.

The biological indicator 100 according to embodiments may be assembled as follows. First, the spore carrier 180 is arranged inside the second shell 130 above the bottom opening 132 and the spores 181 are deposited on the spore carrier 180. Then, the imaging window 190 is inserted into the window notch 133 of the second shell 130 and is secured in place using the retaining ring 191. The germinant pad 185 is arranged above the spore carrier 180. The germinant container 160 is arranged above the germinant pad 185 and in the channel 134, such that the germinant container 160 rests in the channel 134 and is downwardly angled toward the bottom 131 of the second shell 130. The germinant releaser 170 is inserted into the germinant releaser opening 144, typically before insertion of the germinant releaser support 140. The germinant releaser support 140 is arranged above a portion of the germinant container 160 above the imaging window 190, such that the extension portions 142a of the support legs 142 rest on the connecting portions 135a, and the center leg 143 rests on another portion of the germinant container 160. In some embodiments, the germinant releaser 170 is freestanding, i.e., it is not attached to another component of the BI, and enjoys a certain amount of free-play within the BI. The sterilant membrane 105 is arranged above the germinant releaser support 140, and the first shell 120 is arranged above the sterilant membrane 105, such that the protrusion portion 120a, the sterilant membrane 105, the germinant releaser support 140, the germinant releaser 170, the germinant container 160, the spore carrier 180, and the imaging window 190 are in a stacked configuration (see, e.g., FIG. 12). The grooves 125 of the first shell 120 and the protrusions 139 of the second shell 130 (or vice versa) are then mated together to securely fasten the BI housing 110. The process indicator 137b may be affixed at the indentation 137a before, during, or after assembly of the BI housing 110, or may be omitted.

FIGS. 13-18 illustrate an alternative biological indicator 100' including a germinant container (e.g., a sealed germinant reservoir) 160' seated above a germinant releaser 170', both accommodated in a second shell 130' and which omits the germinant releaser support 140 described above. Various features of the biological indicator 100' are substantially the same as those described above with reference to the biological indicator 100. As such, additional descriptions thereof may be omitted.

According to embodiments of the present disclosure, the germinant container 160' may be seated on the germinant releaser 170'. The germinant releaser 170' is configured to puncture a barrier 161' of the germinant container 160' when downward pressure is applied to the germinant container 160'.

The germinant container 160' may include an outer container 162' having a hollow interior which houses the germinant 165. The material of the outer container 162' is not particularly limited so long as it can withstand the sterilization conditions and securely house the germinant solution 165. In some embodiments, the germinant container is made of a polymeric material, nonlimiting examples of which include polypropylene homopolymers. The outer container 162' is sealed by the barrier 161', for example, an aluminum foil, that may be heat-sealed to a bottom of the outer container 162'. The barrier 161' is sufficiently robust to eliminate the risk of friction erosion at the interface of the barrier 161' and releaser protrusions 171' of the germinant releaser 170', discussed further below.

In a normal or unactivated state (i.e., when the germinant container 160' is not depressed by the germinant release lever 401), there may be a gap (e.g., about a 1 mm gap) between an interior surface of the first shell 110 and a top 163' of the outer container 162'. The gap may allow for transverse movement of the germinant container 160' within the BI housing 110. The top 163' of the outer container 162' may have a plurality of radial sterilant release pathways (e.g., radial steam release channels) 164' that aid the flow of sterilant toward an interior of the BI housing 310 when the biological indicator 100 is undergoing sterilization. The sterilant release pathways 164' may also prevent the sterilant membrane 105 from collapsing flat against the top 163' of the germinant container 160' and blocking the inflow of sterilant, or reducing the likelihood thereof. The sterilant membrane 105 may be deformable and may increase resistance to the sterilant to limit sterilant access inside of the BI housing 110.

When the germinant container 160' is depressed by the germinant release lever 401 of the BI reader 300, the outer container 162' of the germinant container 160' is configured to not deflect under the pressure, and the germinant container 160' in its entirety is moved vertically (along the thickness direction $Z_{BI}$) down toward and over the germinant releaser 170', which breaks the seal at the barrier 161' and displaces the germinant 165 under pressure. The pressurized evacuation of the germinant 165 can provide reproducibility and speed of release for operation of the BI reader 300.

Figure 14:
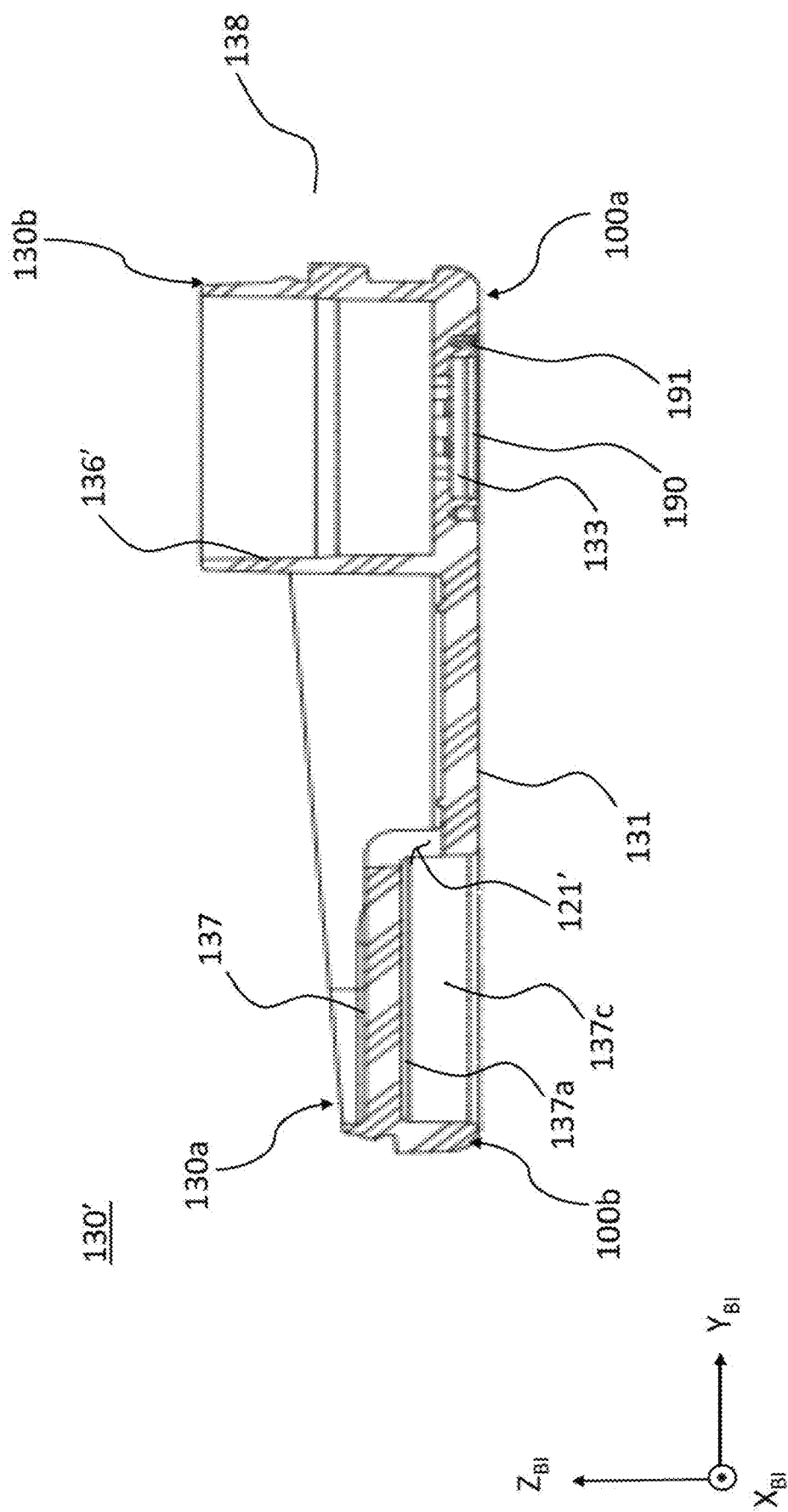
FIG. 14 is a cross-sectional view of a second shell of the biological indicator (BI) of FIG. 13.
Figure 15:
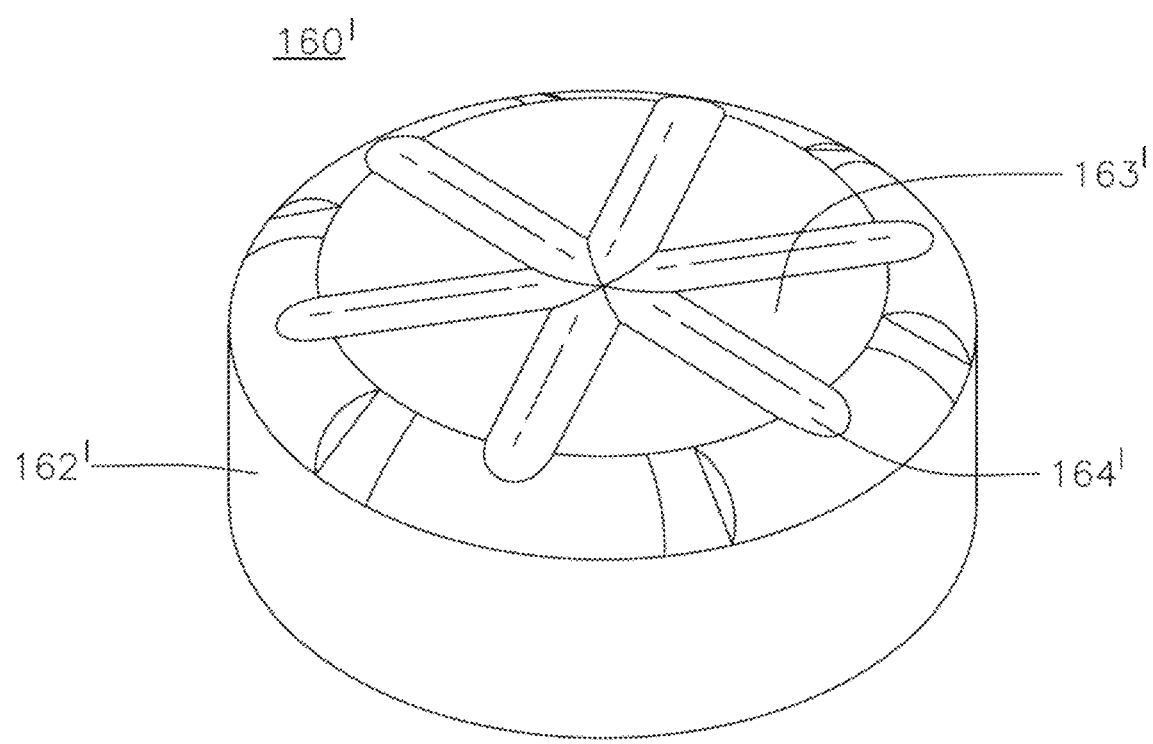
FIG. 15 is a perspective view of a germinant container of the biological indicator (BI) of FIG. 13.

In some embodiments, as generally discussed above, the sterilant opening 121' may be formed in the indentation 137a of the second shell 130'. For example, the indentation 137a may be defined by a short circumferential (or peripheral) sidewall 137c of the projection 137, and the sterilant opening 121' may be formed in the circumferential (or peripheral) sidewall 137c to provide sterilant access into the cavity or interior of the BI housing. The second shell 130' may further include a substantially cylindrical sidewall 136' which houses the germinant container 160' and the germinant releaser 170', as illustrated in FIG. 14.

Figure 18:
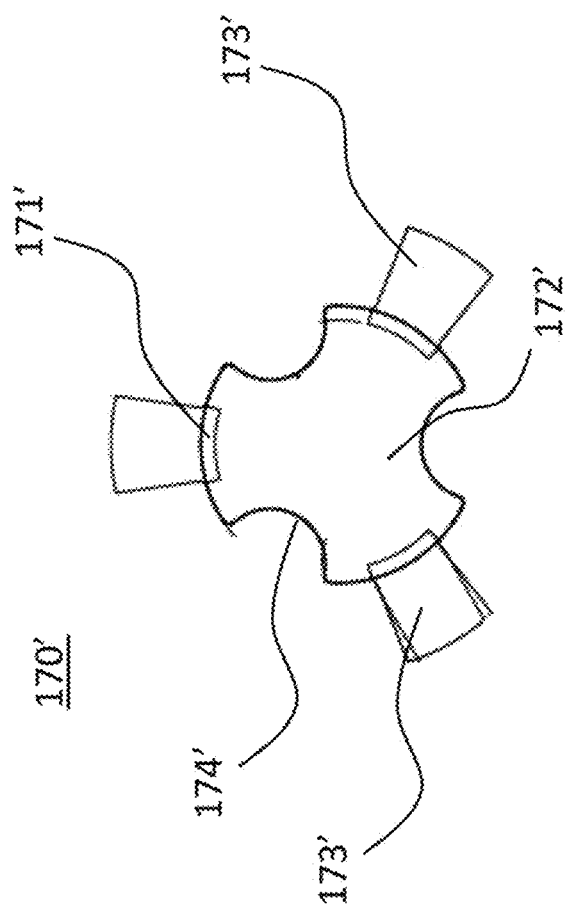
FIG. 18 is a top plan view of the germinant releaser of FIG. 17.
Figure 17:
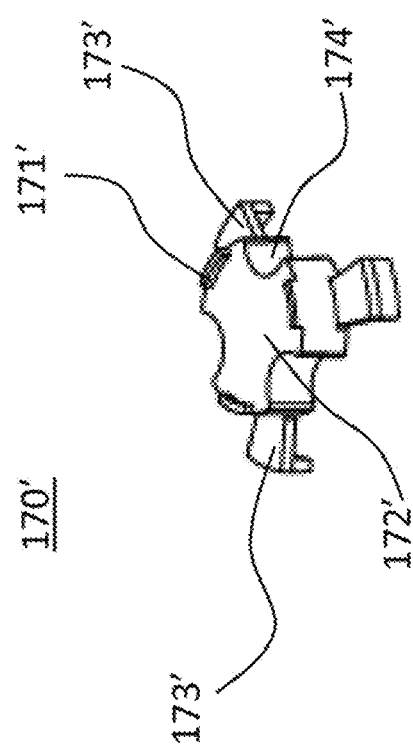
FIG. 17 is a perspective view of a germinant releaser of the biological indicator (BI) of FIG. 13.
Figure 19:
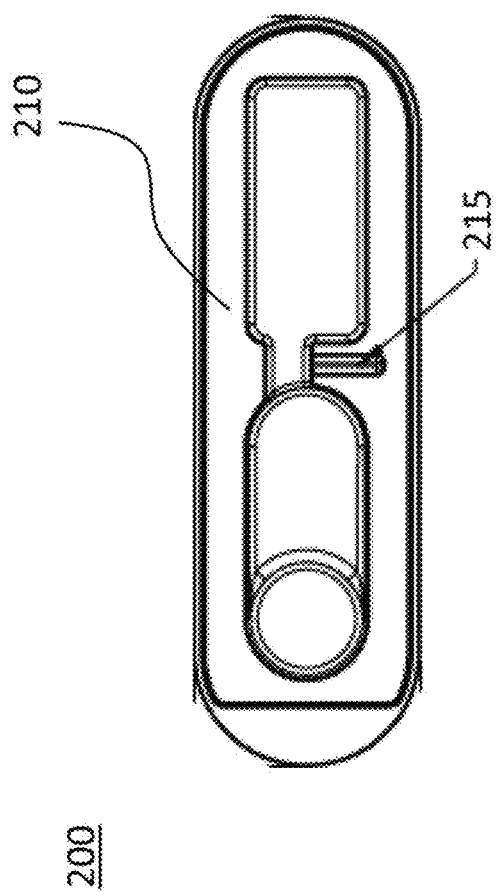
FIG. 19 is a bottom plan view of a process challenge device according to embodiments of the present disclosure.
Figure 20:
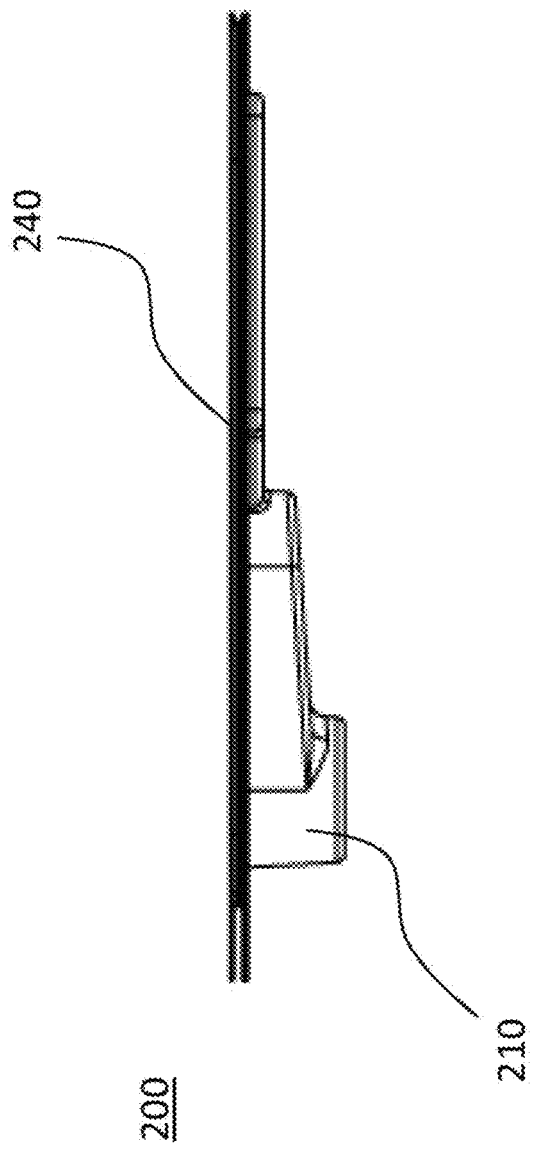
FIG. 20 is a side elevational view of the process challenge device of FIG. 19.
Figure 21:
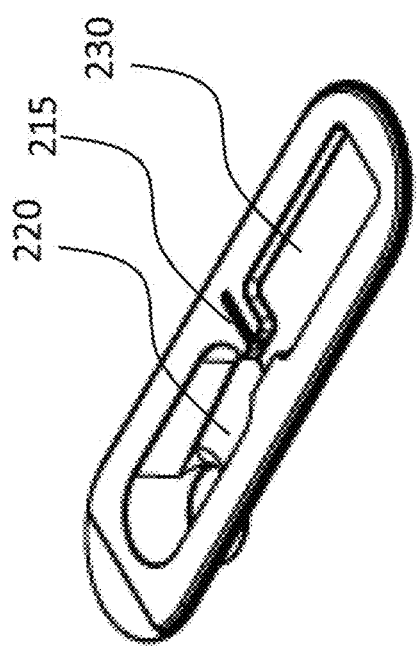
FIG. 21 is a perspective view of a tray of the process challenge device of FIG. 19.
Figure 23:
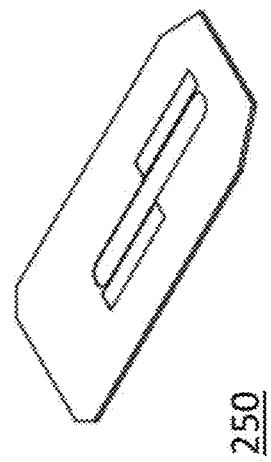
FIG. 23 is a perspective view of a bottom of the steam sterilization integrator of FIG. 22.
Figure 22:
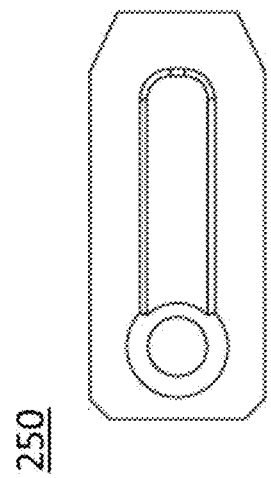
FIG. 22 is a top elevational view of a steam sterilization integrator according to embodiments of the present disclosure.
Figure 24:
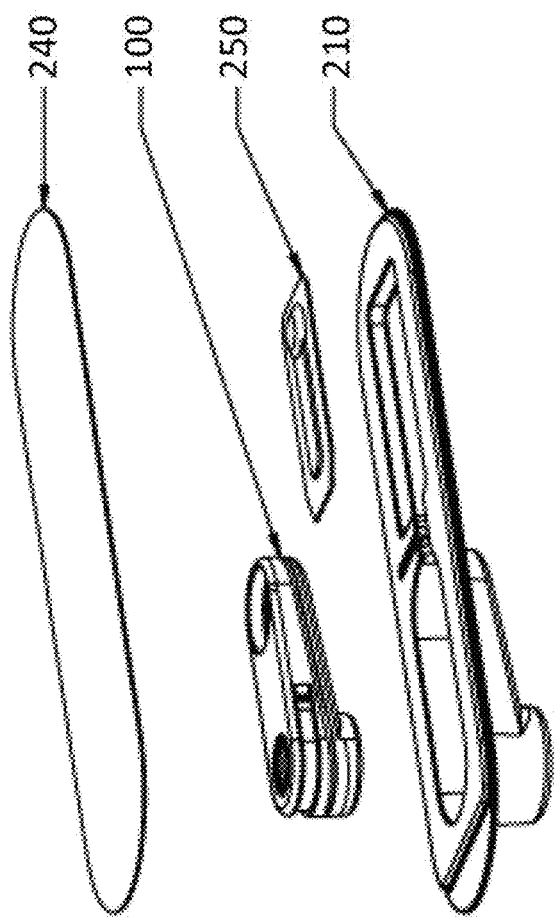
FIG. 24 is an exploded perspective view of the process challenge device of FIG. 19.

Referring to FIGS. 17-18, the germinant releaser 170' may include a plurality of support legs 173' (e.g., three support legs 173') extending from (e.g., extending radially from) a body portion 172' of the germinant releaser 170'. The support legs 173' may separate the body portion 172' of the germinant releaser 170' from the bottom 131 of the second shell 130. The body portion 172' includes releaser protrusions 171', which protrude upwardly along the thickness direction $Z_{BI}$ and toward the germinant container 160'. The releaser protrusions 171' are configured to engage the barrier 161' at the bottom of the germinant container 160'. As the germinant container 160' is depressed toward the body portion 172', the releaser protrusions 171' press against the barrier 161' and break the seal formed by the barrier 161', thereby releasing the germinant 165. The body portion 172' may include one or more releaser notches 174' around a periphery of the body portion 172' that facilitate flow of the germinant 165 past the germinant releaser 170' and toward the germinant pad 185 when the barrier 161' of the germinant container 160' is ruptured.

According to embodiments, the germinant releaser 170' is free of any sharp edges or pointed upward facing surfaces, including the releaser protrusions 171', so that the germinant container 160' may safely rest on top of the body portion 172' by way of gravity without prematurely rupturing (e.g., inadvertently rupturing) the germinant container 160'.

The material of the germinant releaser is not particularly limited, as discussed generally above in connection with germinant releaser 170. In some embodiments, for example, the germinant releaser 170' may be made of a polypropylene homopolymer.

The germinant container 160' utilizing a sealed foil, for example, may provide for a relatively long shelf life and durability during the sterilization cycle. However, the foil barrier 161' may fail during a subsequent dry time following the sterility procedure (e.g., autoclave cycle), and the barrier 161' may separate to some degree from the outer container 162'. Suitable material selection for the barrier 161' may reduce the likelihood of separation.

For convenience, reference is made to the biological indicator 100 in the detailed description below. However, it will be appreciated that other embodiments, including the biological indicator 100', may be utilized with the process challenge device 200 and the BI reader 300.

Referring to FIGS. 19-24, the biological indicator 100 may be inserted into a process challenge device (PCD) 200 prior to being subjected to the sterilization process. In some embodiments, the PCD 200 may include a tray 210, a closure portion 240, a sterilant sterilization integrator (or chemical integrator) 250, and the BI 100.

According to embodiments, the tray 210 may define a first cavity 220, a second cavity 230, and a sterilant access port 215. The first cavity 220 has a shape corresponding to a shape of the biological indicator 100 (i.e., of the BI housing 110), and is configured to receive the biological indicator 100 in a "face-down" configuration, i.e., with the first shell 120 facing and contacting the first cavity 220 and the bottom 131 facing away from the first cavity 220. The second cavity 230 is configured to receive the sterilant sterilization integrator 250. The first cavity 220 and the second cavity 230 are in fluid communication with each other. In some embodiments, the sterilant access port 215 is located at a central portion of the tray 210 between the first cavity 220 and the second cavity 230, but the present disclosure is not limited thereto, and the sterilant access port 230 may be located in any suitable position. The sterilant access port 215 is also in fluid communication with the first cavity 220 and the second cavity 230.

The material of the tray is not particularly limited so long as it can withstand the sterilization conditions to which is subjected. Some non-limiting examples of suitable materials for the tray 210 include polymeric materials with resistance to sterilization conditions, e.g., polypropylenes. Additionally, the material of the tray may be at least partially transparent to allow for visual confirmation of the sterilant sterilization integrator 250 while sealed.

The sterilant sterilization integrator 250 may be used to confirm that desired sterilant sterilization criteria are met during sterilization by visual confirmation through the tray 210. For example, the sterilant sterilization integrator 250 may be a PROPPER® VAPOR LINE® steam sterilization integrator, model number 26900925 (PROPPER® and VAPOR LINE® are registered trademarks of Propper Manufacturing Company, Inc.). However, the present disclosure is not limited thereto, and any suitable means for providing an indication of sterilant introduction into the PCD may be utilized.

According to embodiments, the closure portion 240 may be a foil sheet or other material that can maintain a firm seal but is also relatively easily ruptured to allow for removal of the biological indicator 100 after the sterilization procedure. The closure portion 240 may be sealed (e.g., heat sealed) to the tray 210 after the sterilant sterilization integrator 250 and the biological indicator 100 are inserted into the tray 210.

The assembled PCD 200, including the biological indicator 100, may be subjected to the sterilization procedure for testing. During the sterilization procedure, sterilant enters the PCD tray 210 via the sterilant access port 215, and travels through the tray to the BI housing 110 where it enters the BI via the opening 121'. After the sterilization procedure is completed, the biological indicator 100 may be removed from the PCD 200 (i.e., from the tray 210) by puncturing or otherwise separating at least a portion of the closure portion 240 from the tray 210. The biological indicator 100 is then inserted into the BI reader 300 to determine the efficacy of the sterilization procedure, as discussed in greater below.

Referring to FIGS. 25-28, an alternative tray 210' of a PCD 200' is shown. Various features of the alternative PCD are substantially the same as those described above with reference to the PCD 200. As such, additional descriptions thereof may be omitted.

Figure 26:
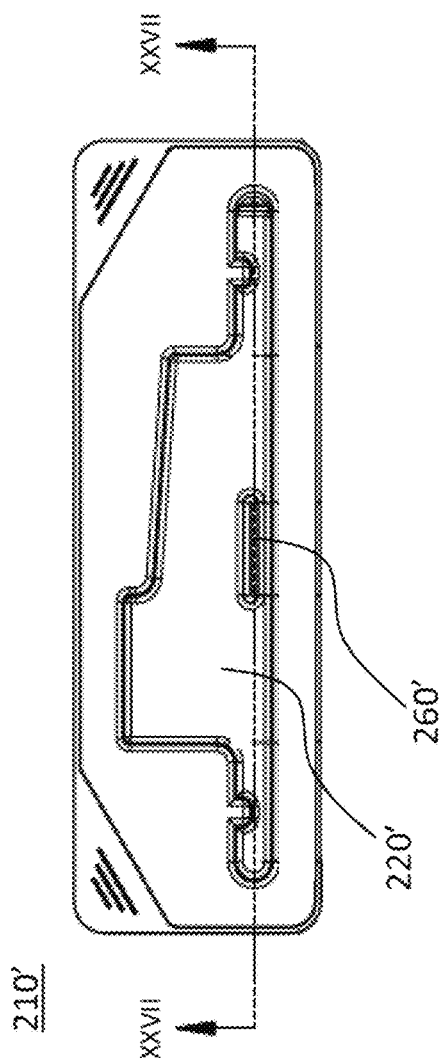
FIG. 26 is a side elevational view of the tray of the process challenge device of FIG. 25.
Figure 25:
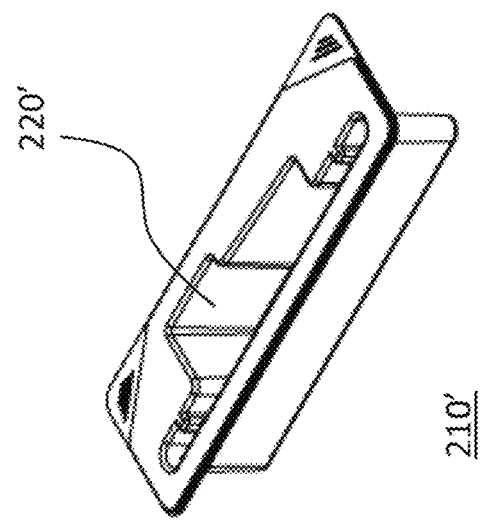
FIG. 25 is a perspective view of a tray of a process challenge device according to embodiments of the present disclosure.
Figure 28:
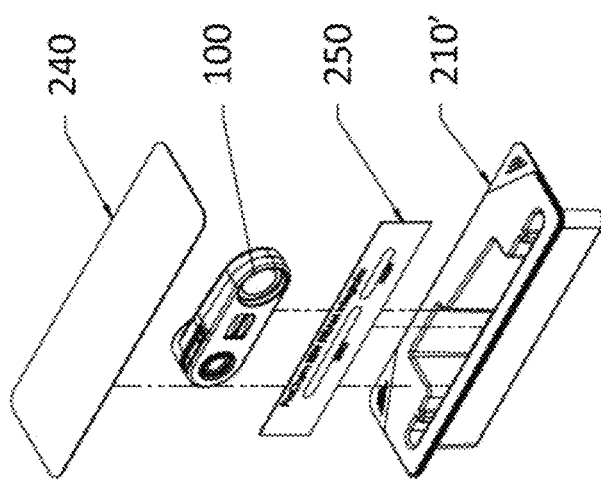
FIG. 28 is an exploded perspective view of the process challenge device of FIG. 25 and a biological indicator (BI) according to embodiments of the present disclosure.

According to some embodiments, the tray 210' of the PCD includes a first cavity 220' and a tab 260'. As illustrated in FIGS. 25 and 26, the first cavity 220' has a shape corresponding to a shape of the biological indicator 100 (i.e., of the BI housing 110), and is configured to receive the biological indicator 100 in a sideways configuration, as opposed to the face-down configuration of the first cavity 220 of the PCD 200. The tray 210' may have a smaller surface area than the tray 210 described above, and therefore may reduce the likelihood of post-processing warpage of the tray 210'.

According to embodiments, the first cavity 220' may receive both the biological indicator 100 and the sterilant sterilization integrator 250. The sterilant sterilization integrator 250 is separated from the first cavity 220' by the tab 260' and is held in place by the tab 260'. The tray 210' further includes a sterilant access port 215', which is formed near a portion of the tray 210' to which the closure portion 240 attaches (see FIG. 27).

The assembled PCD 200', including the biological indicator 100, may be subjected to a sterilization procedure for testing. During the sterilization procedure, sterilant enters the PCD tray 210' via the sterilant access port 215', and travels through the tray 210' to the BI housing 110 where it enters the BI via the opening 121'. After the sterilization procedure is completed, the biological indicator 100 may be removed from the PCD 200' (i.e., from the tray 210') by puncturing or otherwise separating at least a portion of the closure portion 240 from the tray 210'. The biological indicator 100 is then inserted into the BI reader 300 to determine the efficacy of the sterilization procedure, as discussed in greater detail below.

According to embodiments of the present disclosure, the BI reader 300 determines the efficacy of a sterilization run by reading the levels of DPA released by the spores housed in the biological indicator 100 over time. The BI reader 300 includes various modular functional subassemblies that are integrated and interconnected within the BI reader 300 to determine the efficacy of a sterilization run. The BI reader 300 may be operated utilizing an external power supply, for example, a DC power supply.

Figure 29:
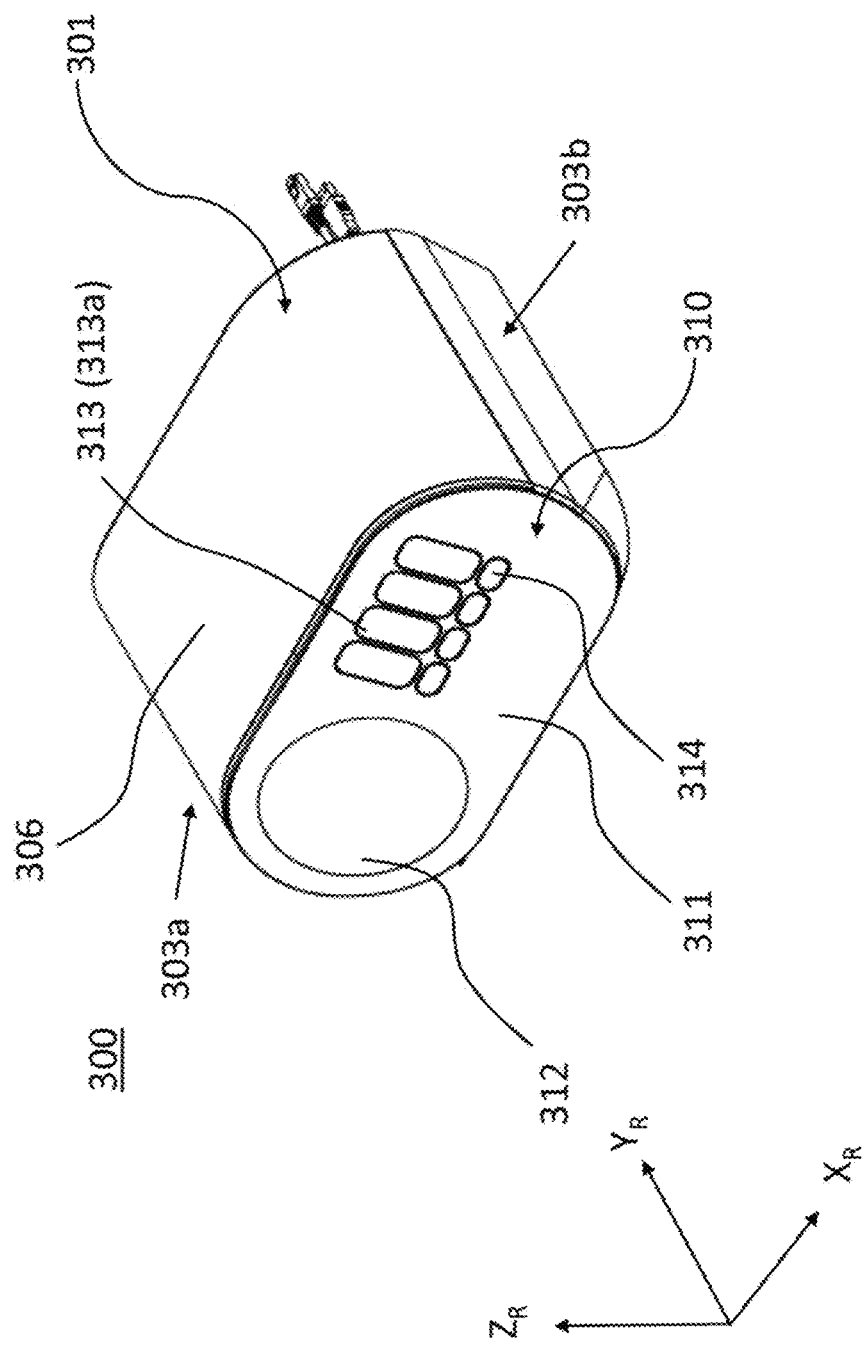
FIG. 29 is a perspective view of a biological indicator (BI) reader according to embodiments of the present disclosure.

According to embodiments of the present disclosure, the BI reader 300 includes a BI reader housing 301 including a front panel assembly 310 and a rear panel assembly 390, an optical assembly including a positioning assembly 340 and a camera assembly 360, and a heater block assembly 370. Referring to FIG. 29, the front panel assembly 310 may include a front panel 311 including a display 312, one or more access doors 313, and corresponding access door releases 314. According to embodiments, the display 312 may be a touch panel display, such as a thin film transistor liquid crystal display module or an OLED display, that is configured to receive user inputs via touch screen and to display information to a user. However, the present disclosure is not limited to such touch panel displays, and may be any display capable of receiving user inputs (e.g., via tactile buttons which may be designed to allow a user to scroll through various menu options), and displaying necessary information (e.g., via a non-touch screen display window). The display 312 is connected to a display control board 315 (see FIG. 32), which communicates with various other control boards in the BI reader 300 to operate the BI reader 300, as discussed further below. The control boards of the BI reader 300 are collectively referred to herein as the control system.

Figure 30:
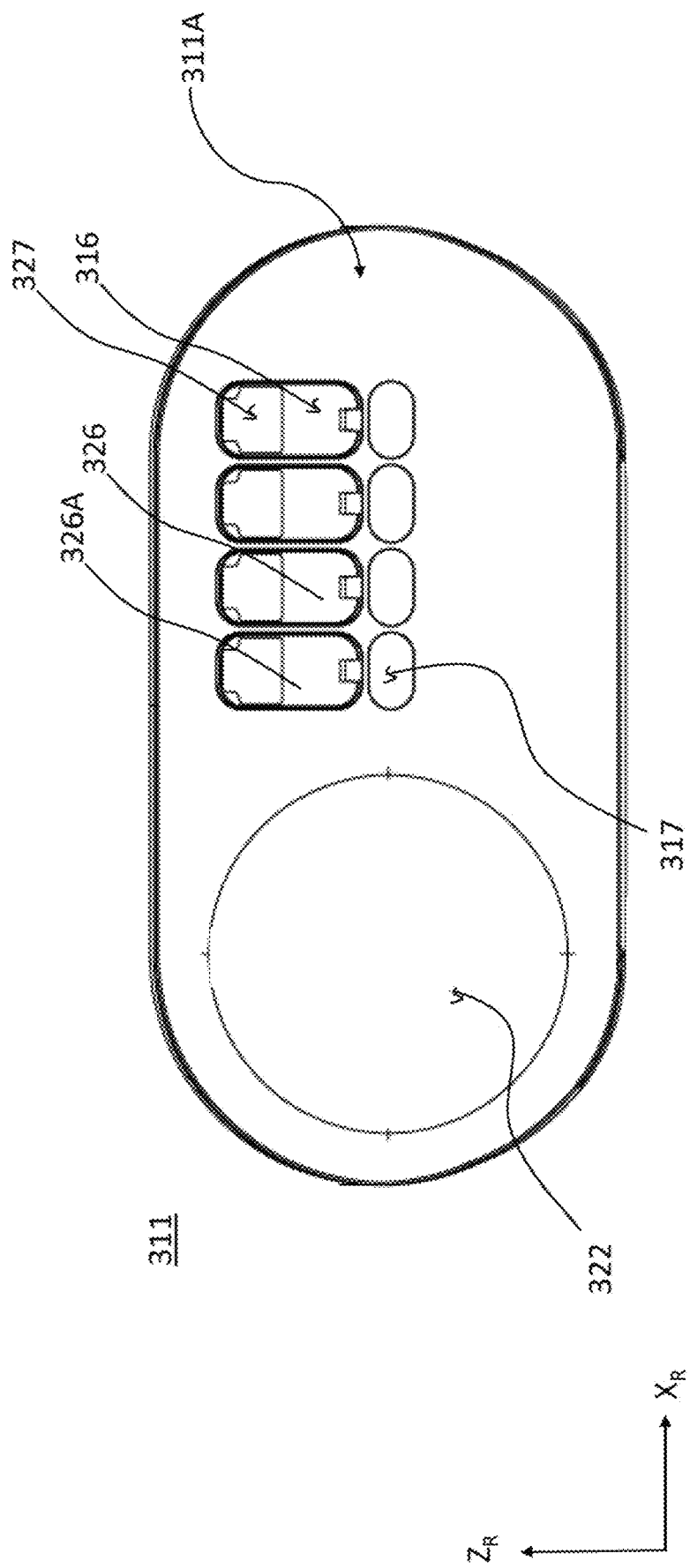
FIG. 30 is a front elevational view of a front surface of a front panel of the biological indicator (BI) reader of FIG. 29.
Figure 31:
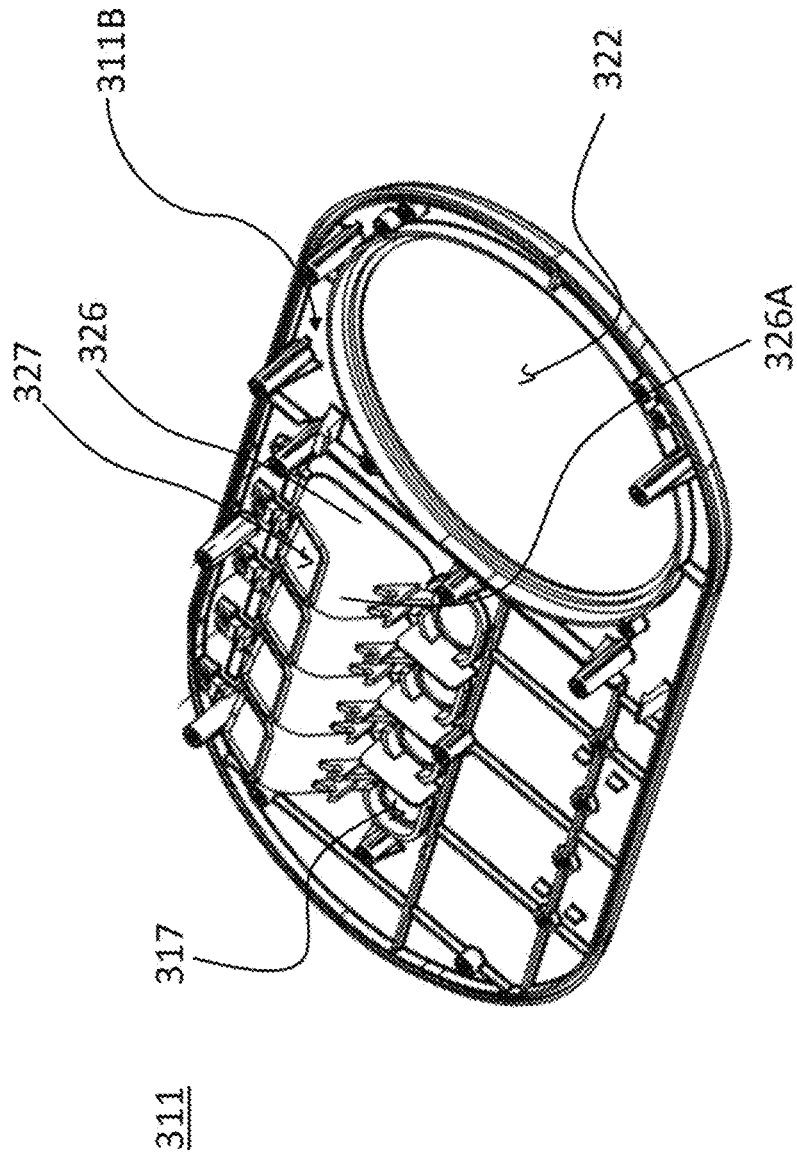
FIG. 31 is a perspective view of a back surface of the front panel of FIG. 30.

Referring to FIGS. 30-31, the front panel 311 may define one or more door openings 316, one or more door release openings 317, and a display opening 322. The size and shape of the door openings 316 are not particularly limited so long as the BIs 100 fit within the openings and the openings can accommodate the access doors when the Bis 100 are inserted, as discussed further below. For example, in some embodiments, the door openings 316 may have a substantially rectangular shape when viewed in the plane of the front surface 311A of the front panel 311, and may have rounded corners.

As illustrated in FIGS. 30-31, the front panel 311 may include one or more chambers 326 that respectively correspond to and define the one or more door openings 316, each having a chamber opening 327 in fluid communication with the respective door openings 316. The chambers 326 each protrude from a back surface (or inner surface) 311B of the front panel 311 and are configured to guide the biological indicator 100 to the heater block assembly 370 when it is inserted into the door opening 316, as discussed further below. The chambers 326 may have any suitable shape without limitation. According to embodiments, the door opening 316 may have a height that is greater than a height of the biological indicator 100. In such embodiments, the chambers 326 may each have an upwardly sloped portion 326A (seen best in FIG. 34) that extends from the back surface 311B at a lower portion of the door opening 316 and that guides the biological indicator 100 toward the chamber opening 327 when the biological indicator 100 is inserted from below the chamber opening 327. The chambers 326 may similarly each have a downwardly sloped portion 326B (seen best in FIG. 34) that extends from the back surface 311B at an upper portion of the door opening 316 and that helps guide the biological indicator 100 toward the chamber opening 327 when the biological indicator 100 is inserted from above the chamber opening 327.

The size and shape of the door release openings 317 are also not particularly limited, and may have any suitable size and shape so long as they can receive the corresponding access door releases 314. For example, in some embodiments, each of the door release openings 317 may have a substantially obround shape and may be located adjacent its corresponding door opening 316 such that each door opening 316 has a corresponding door release opening 317. In some embodiments, the door release openings 317 may be located beneath their corresponding door openings 316, but the present disclosure is not limited thereto, and the door release openings may be located anywhere on the front panel 311. Indeed, in some embodiments, the door release openings 317 may be located on the front panel in positions that do not correspond, or are not adjacent the corresponding door openings. Each of the door release openings 317 may occupy an area on the front panel that is smaller than the area occupied by their corresponding door openings 317, but the present disclosure is not limited thereto, and the door release openings 316 may have any suitable size and shape, as noted above.

Figure 32:
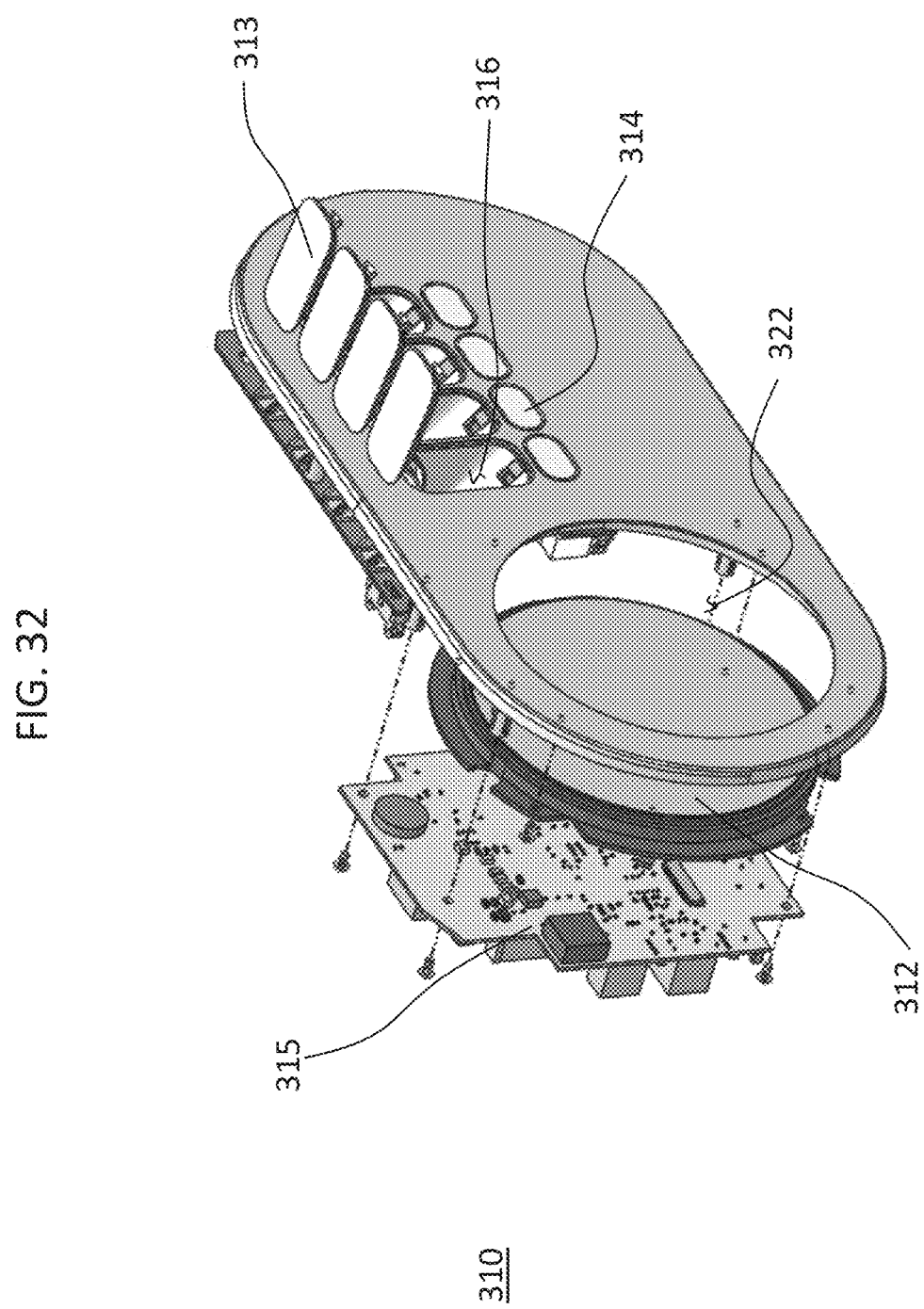
FIG. 32 is an exploded perspective view of a front panel assembly of the biological indicator (BI) reader of FIG. 29.

Referring to FIG. 32, the display 312 is received in the display opening 322. According to embodiments, the display 312 and the display opening 322 may each have a substantially circular shape when viewed in a plan view. However, the present disclosure is not limited thereto, and the display 312 and the display opening 322 may have any suitable shape such that the display 312 may be received in the display opening 322 and such that the display 312 may receive instructions from the display control board 315 and be visible to a user. For example, in some embodiments, the display 312 and the display opening 322 may have a square, rectangular, ovular or any other geometric shape. The display 312 provides information to a user, such as whether the BI reader 300 is ready to receive a BI 100, cycle history, date, time, an associated IP address, etc.

Figure 34:
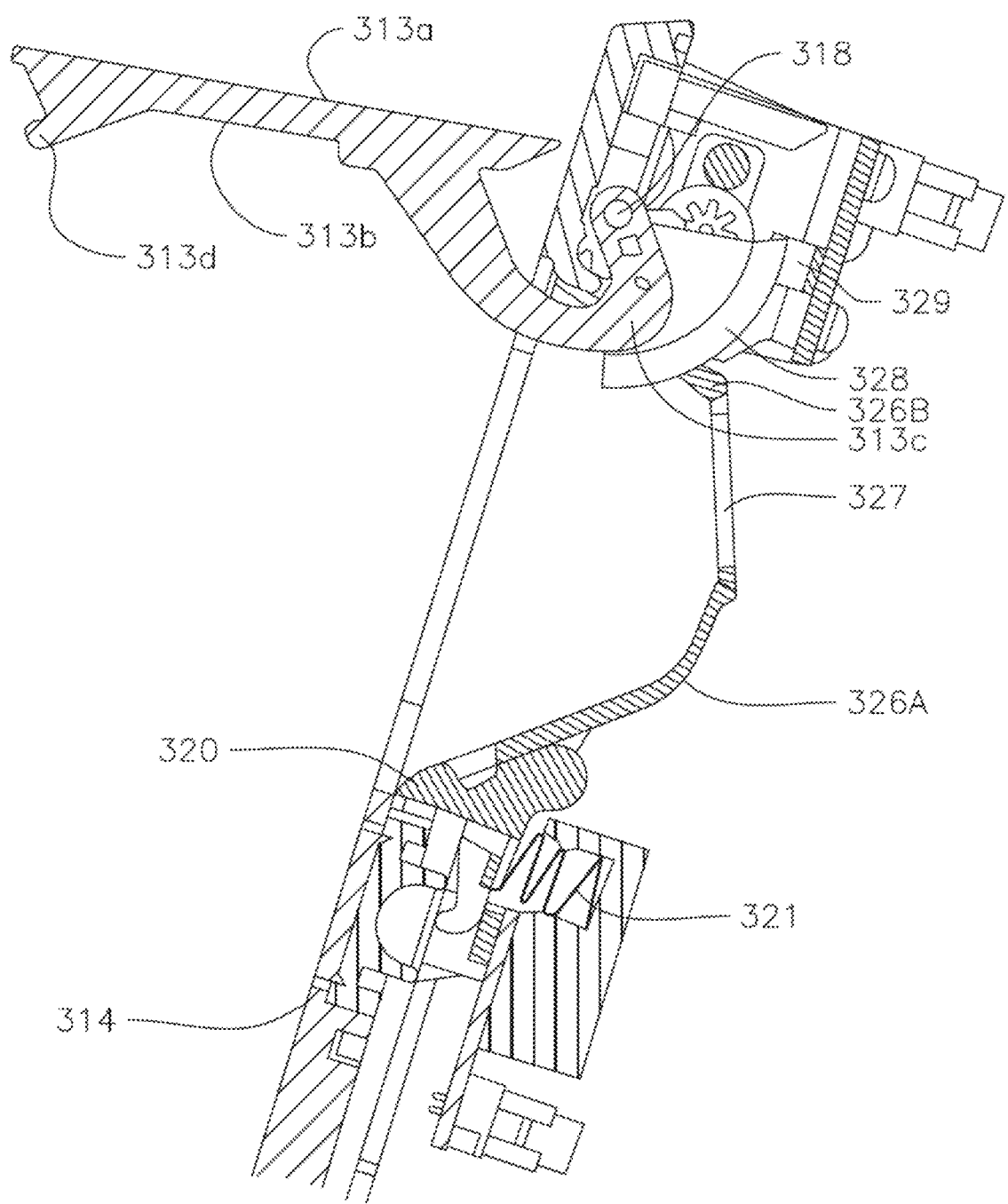
FIG. 34 is a side view of an access door in an open configuration attached to the front panel of the biological indicator (BI) reader of FIG. 29.

The access doors 313 are configured to fit inside of the door openings 316, and to be moved between an opened configuration (to receive or remove a BI 100) and a closed configuration (during operation of the reader or when in stand-by). Similarly, the access door releases 314 are configured to fit inside of the door release openings 317. As shown in FIGS. 31 and 34, the access door releases 314 may be configured as mechanical buttons that are depressed into the door release openings 317 to actuate the access doors 313. However, the present disclosure is not limited to such a configuration of the access door releases 314, and indeed, any mechanism for actuating the access doors 313 can be used. In some embodiments, for example, the access door releases 314 may be electronic, and actuated by a simple touch of the access door release 314 or depression of a tactile button that triggers the relevant control board to actuate the corresponding access door 313.

Figure 33:
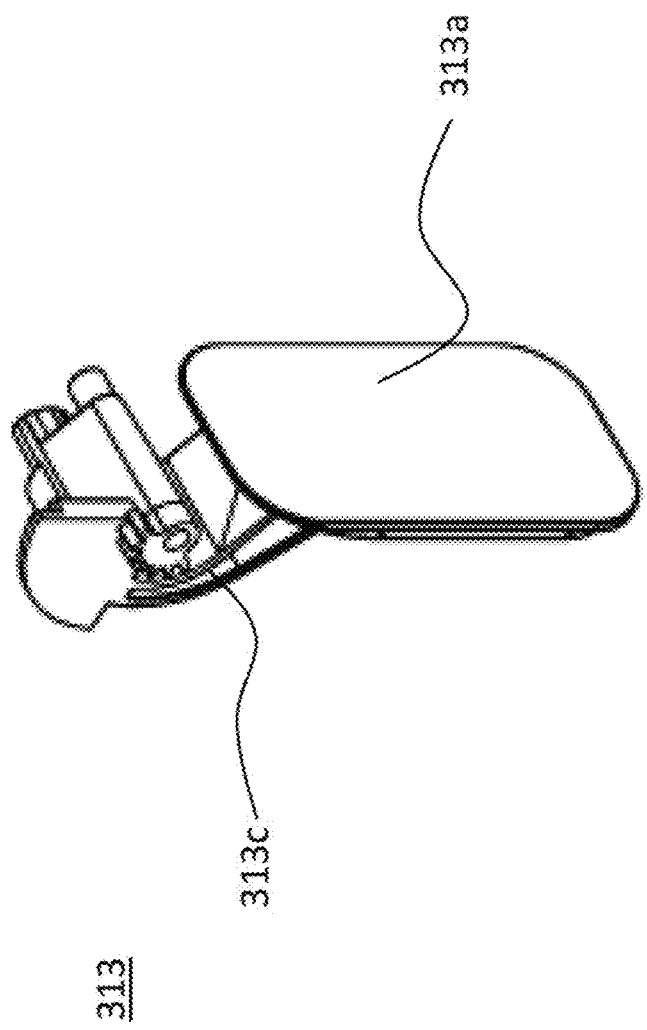
FIG. 33 is a perspective view of an access door of the front panel assembly of the biological indicator (BI) reader of FIG. 29.

Referring to FIGS. 33-34, each of the access doors 313 has an outer panel 313a that faces a user when the access door 313 is in a closed configuration, and an inner panel 313b that faces inside the BI reader 300 when the access door 313 is in a closed configuration. The access door 313 further includes a hook portion 313c at an upper portion thereof, which is connected to a pin 318 at an inner face of the front panel 311. The hook portion 313c of the access door 313 is configured to pivot about the pin 318, allowing the access door 313 to be moved between the opened configuration and the closed configuration when the access door 313 is unlocked and actuated by the access door release 314. The front panel assembly 310 may further include a latch 320 and a latch spring 321 adjacent a lower portion of the door opening 316. The latch 320 is configured to mate with a latch plate 313d at a lower portion of the inner panel 313b of the access door 313. When mated, the latch plate 313d and the latch 320 lock the access door 313 in the closed position. And the access door release 314 is configured to release the latch plate 313d from the latch 320 by depressing the latch spring 321, thereby opening the access door 313, as discussed further below.

The access door release 314 may be located directly beneath the access door 313 (or in any other position on the front panel 311). In some embodiments, the access door release 314 may be heat-staked onto a leaf spring, which connects the access door release 314 to the latch spring 321. When the access door release 314 is activated (e.g., pushed inwardly), the latch spring 321 is compressed, shifting the latch 320 and releasing the latch plate 313d so that the access door 313 may pivot about the pin 318 and be moved into the open configuration. According to embodiments, the front panel assembly 310 may further include one or more rotary dampers adjacent the hook portion 313c to dampen action of a torsion spring at the hook portion 313c during actuation of the access door 313.

The access door 313 may include one or more sensors that provide signals to the control system, e.g., relating to whether the access door 313 is in the opened or closed configuration, and indicating whether the BI reader 300 is in operation. For example, the one or more sensors may include a door position sensor, which provides a signal indicating that the access door 313 is in a closed position. Responsive to a signal supplied by one or more of the sensors, the BI reader 300 (via the control system) may prohibit release of the latch plate 313d and lock the door 313 in place, for example, during operation of the BI reader 300, or may prohibit the start of a detection cycle (or cycle) of the BI reader 300 if the access door 313 is in an open configuration. As another example, each of the access doors 313 may include a round segment flag 328 that passes through a slot sensor 329 as the access door 313 is opened, indicating whether the access door 313 is in an open configuration or a closed configuration.

According to embodiments, the front panel assembly 310 may further include a light source (e.g., a backlit LED) located around the periphery of the door release openings 317 such that, when lit, the light source emits a ring of light surrounding the periphery of the door release 314. The light source may be configured to emit light in a variety of colors, for example, red, green, white, and yellow, to provide a user with an indication of the status of a cycle of the BI reader 300. For example, in some embodiments, the light source may emit green light to indicate that the bay 375 corresponding to the access door 313 associated with the door release 314 is empty (i.e., no BI 100 is inserted), may emit red light when the bay 375 is occupied by a BI 100, may emit white light to represent that a test is in process, and may emit a yellow light to represent a warning signal. Alternatively or additionally, the light sources of all door releases 314 may emit green light when the BI reader 300 is ready for use, and emit red light when the BI reader 300 is in operation during a detection cycle. Also alternatively or additionally, the light source of an individual door release 314 may change from red to green upon completion of a detection cycle. Also, the light source (either individually, or all of them at once) may flash red to indicate a reader fault, or may flash individually to indicate that the reader 300 detected a viable spore in the BI 100 inserted in the corresponding bay 375. As would be understood by those of ordinary skill in the art, the light sources associated with the door releases 314 may be programmed and controlled by the control system to emit light of any color, to change from one color to another, or to flash in any of a variety of patterns to indicate various system conditions, without limitation.

Figure 35:
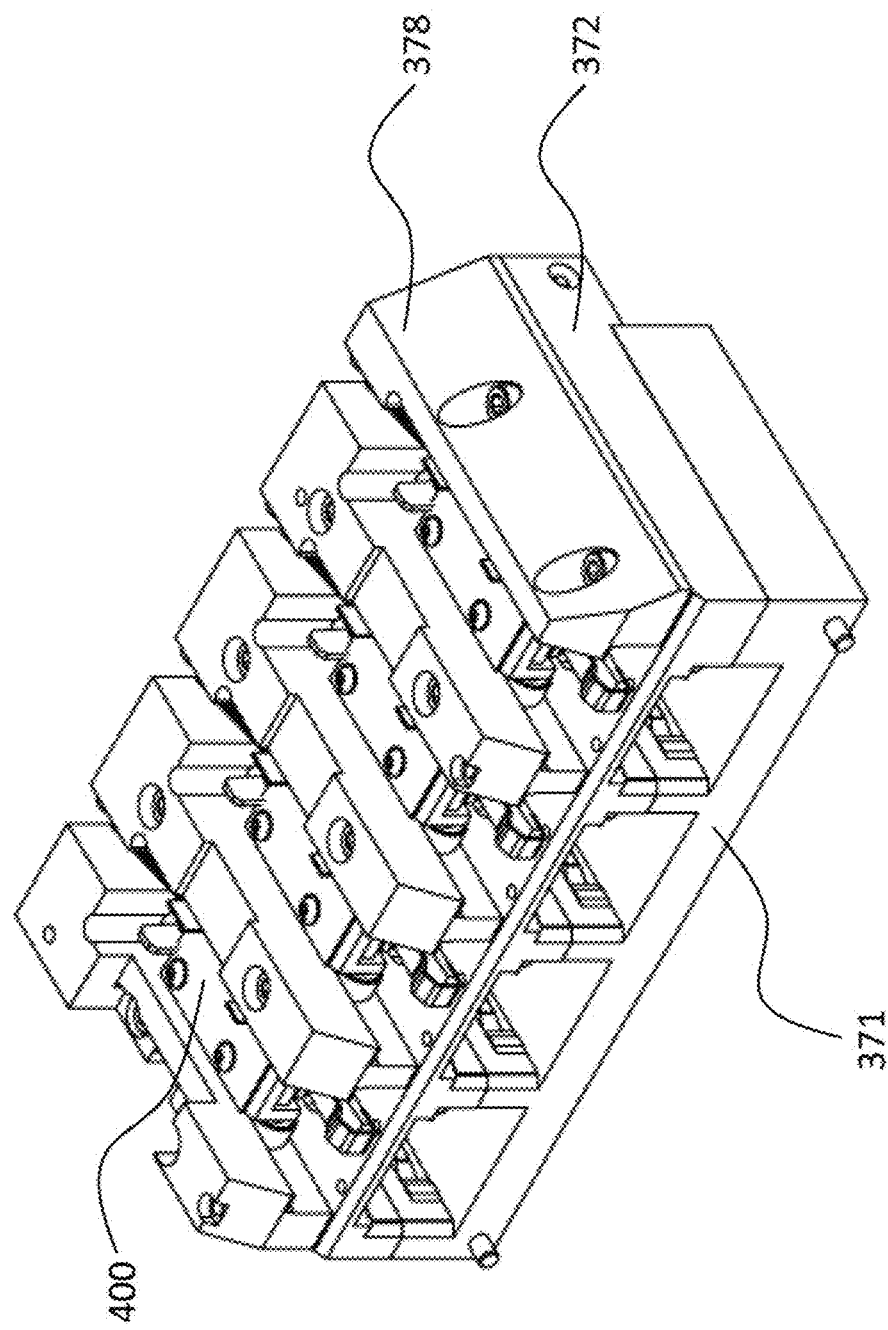
FIG. 35 is a perspective view of a heater block assembly of the biological indicator (BI) reader of FIG. 29.
Figure 36:
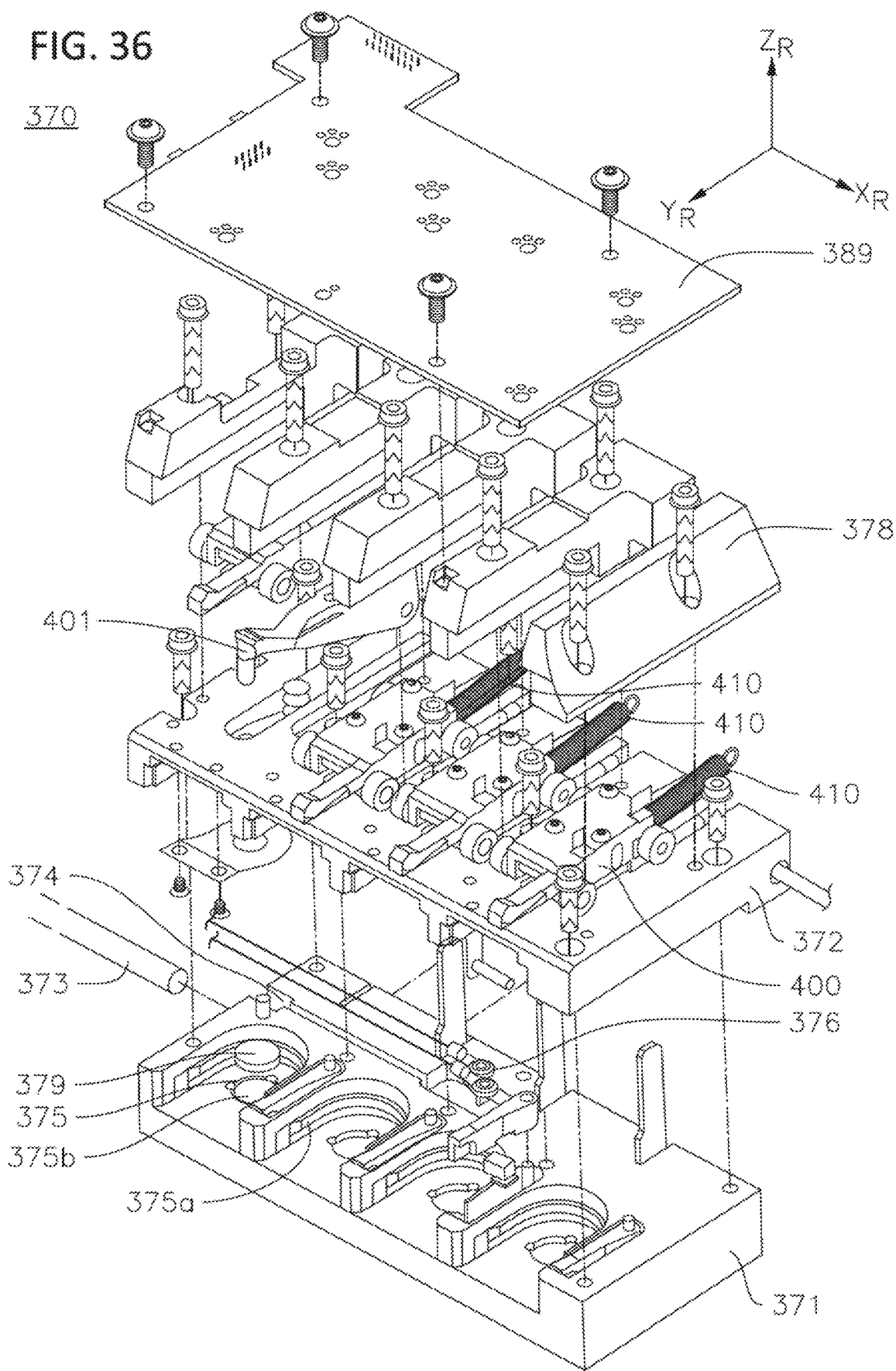
FIG. 36 is an exploded perspective view of the heater block assembly of FIG. 35.

As briefly discussed above, the front panel assembly 310 forms a portion of the BI reader housing 301 and provides access to the heater block assembly 370 located inside the BI reader housing 301. Referring to FIGS. 35-36, the heater block assembly 370 may include a first heating plate (or a lower heating plate) 371, a second heating plate (or an upper heating plate) 372, and a heater cartridge 373. The second heating plate 372 is firmly mounted on the first heating plate 371 to establish a strong thermal contact between the first and second heating plates 371, 372. The heater cartridge 373 may be inserted into a heater channel 374 defined in the first heating plate 371. The heater cartridge 373 may be configured to heat the first heating plate 371 to approximately 56 degrees C. to above 62 degrees C., and more preferably to approximately 60 degrees C. and may be configured to maintain a relatively constant temperature of the first heating plate 371 during operation of the BI reader 300. For example, the heater cartridge 373 may be configured to maintain a temperature of the first heating plate 371 at a temperature of +/−2 degrees C. from a predetermined temperature (e.g., between 54 degrees C. and 64 degrees C., depending on the predetermined temperature of the heater cartridge 373). It will be appreciated that the heater cartridge 373 is configured to heat the first heating plate 371 to a temperature that is below a maximum temperature at which the spores 181 incubate. As such, the temperature at which the first heating plate 371 is heated may differ depending on the type of spores used in the BIs 100 being tested, and thus, the temperature of the heating cartridge 373 and the first heating plate 371 is adjustable.

According to embodiments, the heater block assembly 370 is configured to reach a set temperature, e.g., 60 degrees C., within 15 minutes of operation of the heater block assembly, and to maintain (or substantially maintain) the set temperature for a prolonged period of time (e.g., during operation of the BI reader 300).

The heater cartridge 373 is not particularly limited, and may be any suitable heating element having any size and shape so long as it is capable of fitting in a dedicated space within the first heating plate 371 and generating enough heat to maintain the first and second heating plates 371 and 372 at the selected temperature. In some embodiments, for example, the heating cartridge 373 may include a metal sheath (e.g., a 304 stainless steel sheath) having a substantially cylindrical shape and operating at 12 V/24 W that is designed for high temperature operation and to transfer heat from the heater cartridge 373 to the first and second heating plates 371, 372.

The first and second heating plates 371, 372 are also not particularly limited, and may be made of any suitable material and have any size and shape so long as they are able to fit in their designated space within the BI reader 300 and maintain the selected temperature. For example, in some embodiments, the first and second heating plates 371 and 372 may be made of a metal with high thermal conductivity, e.g., an anodized metal such as aluminum, so that the first and second heating plates 371, 372 may be efficiently heated by the heater cartridge 373. The heater block assembly 370 may be configured to maintain a temperature that is the same (or substantially the same) across an entirety of the first heating plate 371, such that each of the BI bays 375 (e.g., four BI bays 375) are maintained at substantially the same temperature. As used herein, the term "substantially" is used as term of approximation, and not as a term of degree, and is intended to account for inherent deviations and inaccuracies in certain measurements, observations or properties. For example, as used herein, "substantially the same temperature" denotes that the BI bays 375 are maintained at a temperature that those of ordinary skill in the art would understand to impart no or only negligible changes in the outcome of the detection cycle associated with a particular BI bay 375, but accounts for the possibility that not all of the BI bays 375 may be maintained at exactly the same temperature.

According to embodiments, one or more temperature sensors (e.g., thermistors) 376 may be mounted on the first heating plate 371. The temperature sensors 376 may be spaced apart from each other to obtain temperature readings at different locations on the first heating plate 371. The temperature sensors 376 monitor the temperature of the first heating plate 371 and output temperature readings (e.g., with averaging) to the control system, and the control system, in response to the temperature readings may then regulate (or adjust) heat output from the heater cartridge 373 accordingly. The temperature sensors 376 may also be used to determine when the first heating plate 371 has reached the set temperature (e.g., upon start-up of the BI reader 300), indicating that the BI reader 300 is ready for insertion of the biological indicator 100. For example, the control system receives temperature readings from the temperature sensors 376, and displays information regarding that reading on the display 312. In response to the temperature readings, the control system may also activate one or more of the light sources associated with the door releases 314. For example, upon start-up of the BI reader 300, and upon receiving temperature readings from the temperature sensor(s) 376 that the heater block 370 (or the first heating plate 371) has reached the threshold (or set) temperature, the control system may activate the light sources to change from red to green and/or may display a ready-for-use message on the display 312.

One or more BI bays 375 may be formed in the first heating plate 371. As discussed above, each of the BI bays 375 may have a shape that substantially corresponds to the obround shape of the first end 100a of the biological indicator 100 so that the first end 100a of the biological indicator 100 may be securely inserted into the BI bay 375, e.g., with a transition fit. For example, the BI bays 375 may each have a partially obround shape, as illustrated in FIGS. 36-39. The BI bay 375 may include a tongue 375a that mates with the insertion groove 138 of the BI 100 to further aid in providing proper alignment of the biological indicator 100 inside the BI bay 375.

A lower surface of the BI bay 375 includes an opening 375b, which is configured to align with the imaging window 190 when the biological indicator 100 is inserted in the BI bay 375. A BI window 379 may be located in the opening 375b. The BI window 379 may be transparent so that light can travel through the BI window 379 to the imaging window 190. For example, the BI window 379 may be transparent to UV light, and in some embodiments may include a UV grade fused silica quartz, which reduces the likelihood of condensation forming on the BI window 379 during operation of the BI reader 300. The lower surface of the BI bay 375 is configured to contact the bottom 131 of the biological indicator 100 when the biological indicator 100 is inserted into the BI reader 300.

According to embodiments, the first heating plate 371 further includes a movable rod 380, which contacts a movable BI presence flag 381 that is in communication with a BI presence sensor 382. The movable rod 380 may be slidable, for example, and may be configured to partially extend into the BI bay 375 when there is no biological indicator 100 in the BI bay 375. When the biological indicator 100 is inserted into the BI bay 375, the biological indicator 100 moves the movable rod 380 in an insertion direction of the biological indicator 100, which brings the movable rod 380 into contact with the movable BI presence flag 381, thereby triggering the BI presence sensor 382, which then communicates with the control system of the BI reader 300.

According to embodiments, the first heating plate 371 further defines one or more BI latch openings 383 that are respectively adjacent each of the BI bays 375. The BI latch openings 383 are configured to accommodate a BI latch 384 having a rib 387 that engages a portion of the insertion groove 138 of the biological indicator 100 (between the second end 100b of the biological indicator 100 and the protrusion 339) when the biological indicator 100 is fully inserted into the BI bay 375. The BI latch 384 is configured to lock the biological indicator 100 in place and to assist in proper alignment of the biological indicator 100 within the BI bay 375 and to reduce the likelihood of the biological indicator 100 moving after insertion into the BI bay 375. In this way, the latch also provides additional assurance that the BI 100 is properly positioned within the BI bay 375 to align the bottom opening 132 and imaging window 190 for proper reading by the BI reader 300, as discussed further below.

Figure 37:
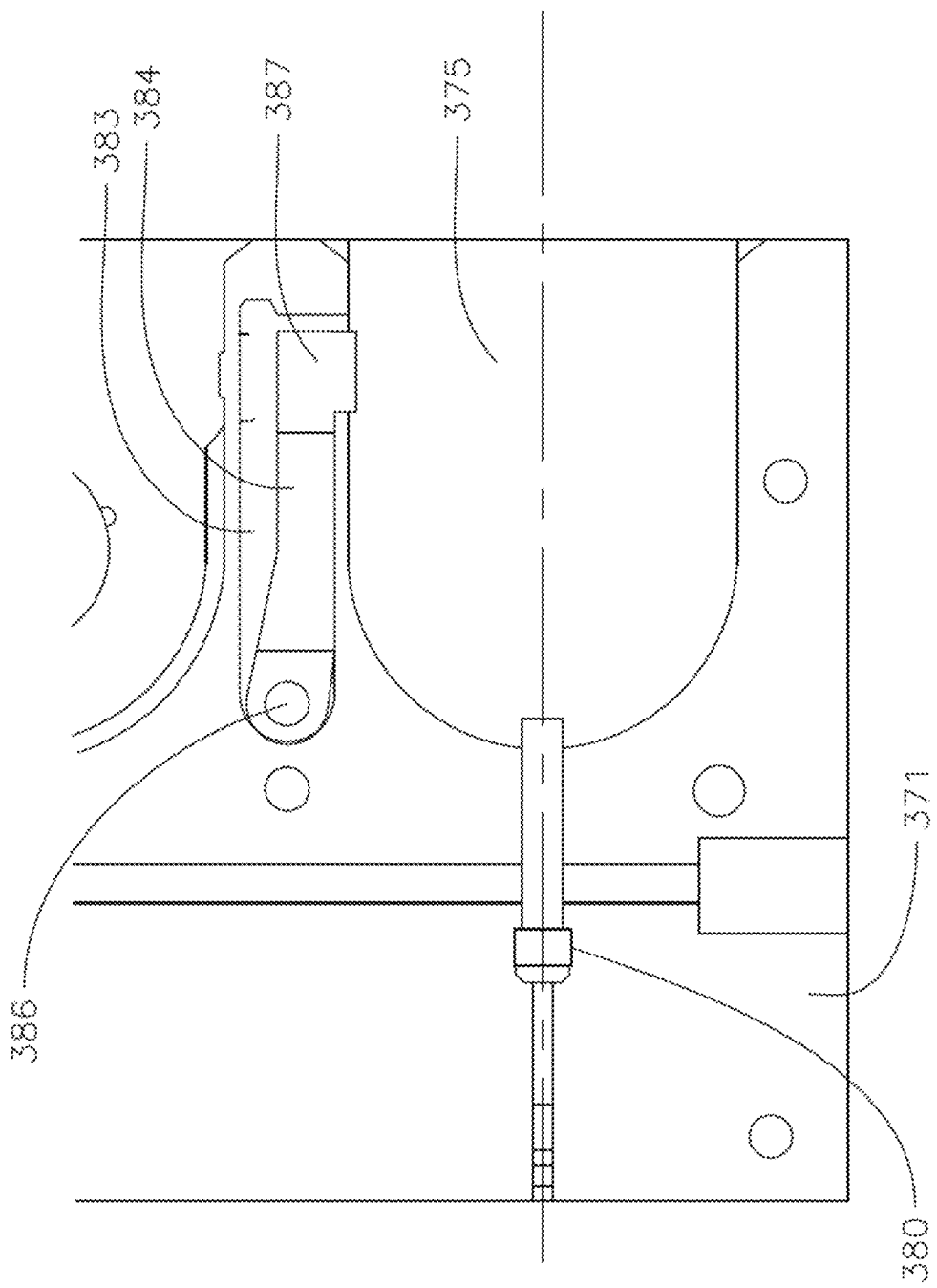
FIG. 37 is a top view of a biological indicator bay of a first plate of the heater block assembly of FIG. 35 prior to insertion of a biological indicator (BI) therein according to embodiments of the present disclosure.
Figure 38:
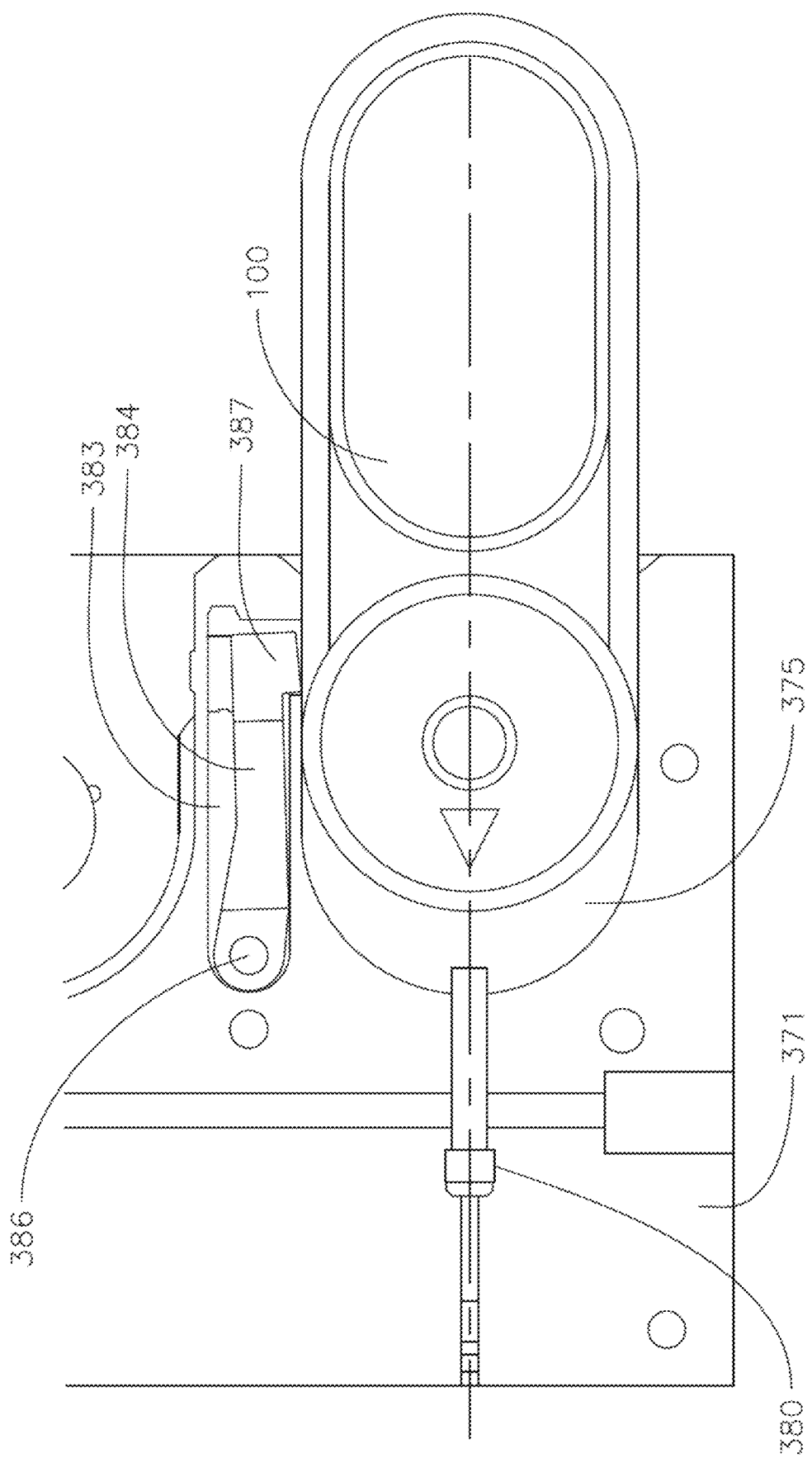
FIG. 38 is a top view of the biological indicator (BI) bay of the first plate of the heater block assembly of FIG. 35 during insertion of the biological indicator (BI) therein according to embodiments of the present disclosure.
Figure 39:
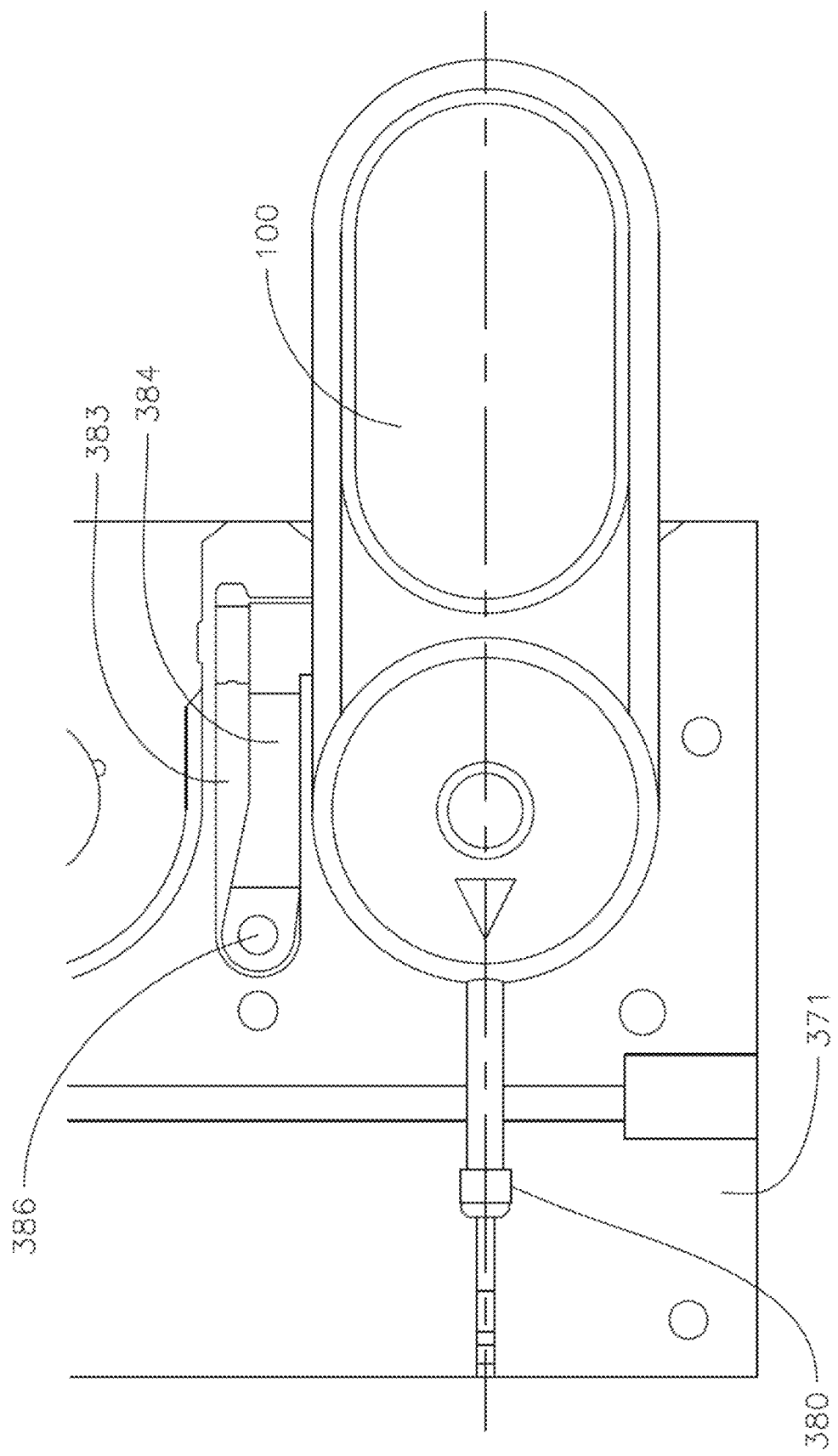
FIG. 39 is a top view of the biological indicator (BI) bay of the first plate of the heater block assembly of FIG. 35 after insertion of the biological indicator (BI) therein according to embodiments of the present disclosure.

Referring to FIGS. 37-39, according to embodiments, the BI latch 384 is movable within the BI latch opening 383 by rotating about a BI latch pin 386. Prior to insertion of the biological indicator 100, the rib 387 extends into the BI bay 375, as shown in FIG. 37. During insertion of the biological indicator 100, the first end 100a of the groove 138 of the biological indicator 100 contacts the rib 387, which helps guide insertion of the biological indicator 100 via contact between the rib 387 and the groove 138. When the rib 387 and the insertion projection 138a of the BI 100 come into contact, the BI latch 384 pivots about the BI latch pin 386 and moves away from the BI bay 375 into the BI latch opening 383 to allow for insertion of the biological indicator 100. As the biological indicator 100 is further inserted into the BI bay 375, and when the insertion notch 138b of the biological indicator 100 is aligned with the rib 387, the BI latch 384 pivots back toward the BI bay 375, and the rib 387 is inserted into the insertion notch 138b of the biological indicator 100, thereby assisting alignment of the biological indicator 100 and reducing the likelihood of the biological indicator 100 moving after insertion into the BI bay 375. Additionally, as noted above, the alignment assistance provided by the latch imparts added assurance of the alignment of the bottom opening 132 and imaging window 190 within the BI bay 375, as noted above. The BI reader 300 may also include a BI presence sensor, which detects the insertion of the biological indicator 100 into the BI bay 375. The BI presence sensor may provide a signal to the control system of the BI reader 300, to prompt the user to close the access door 313.

Figure 40:
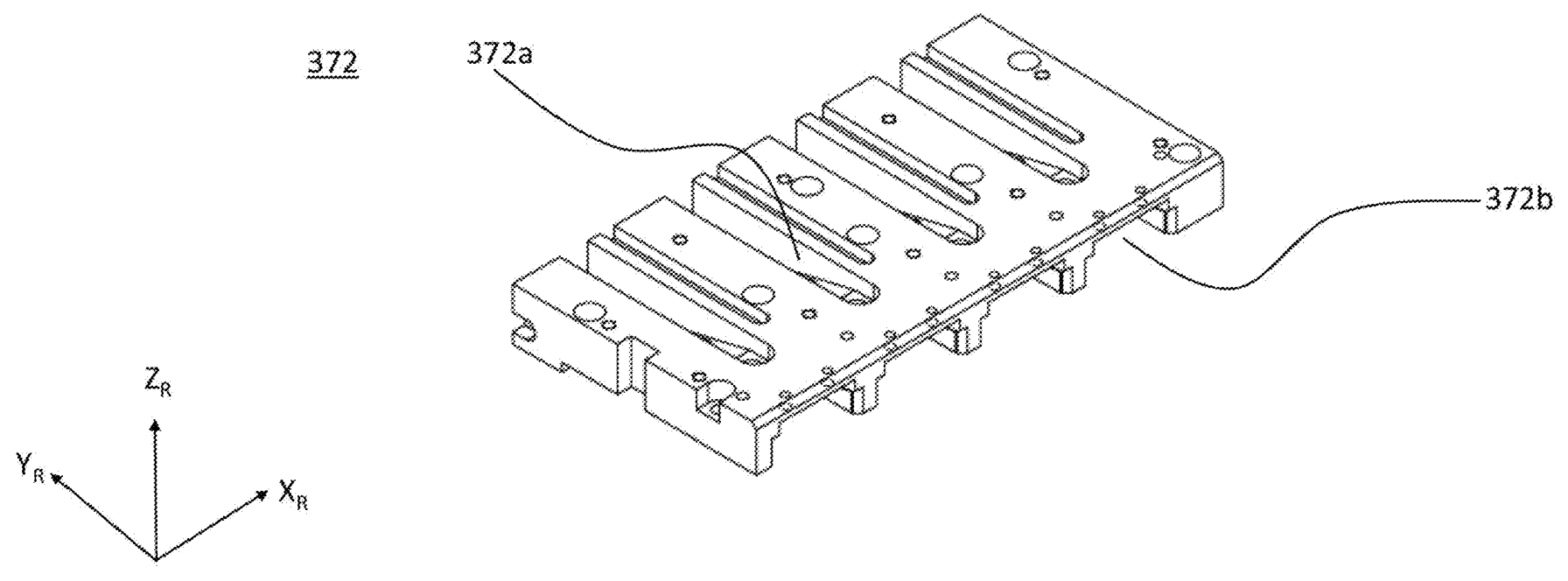
Figure 41:
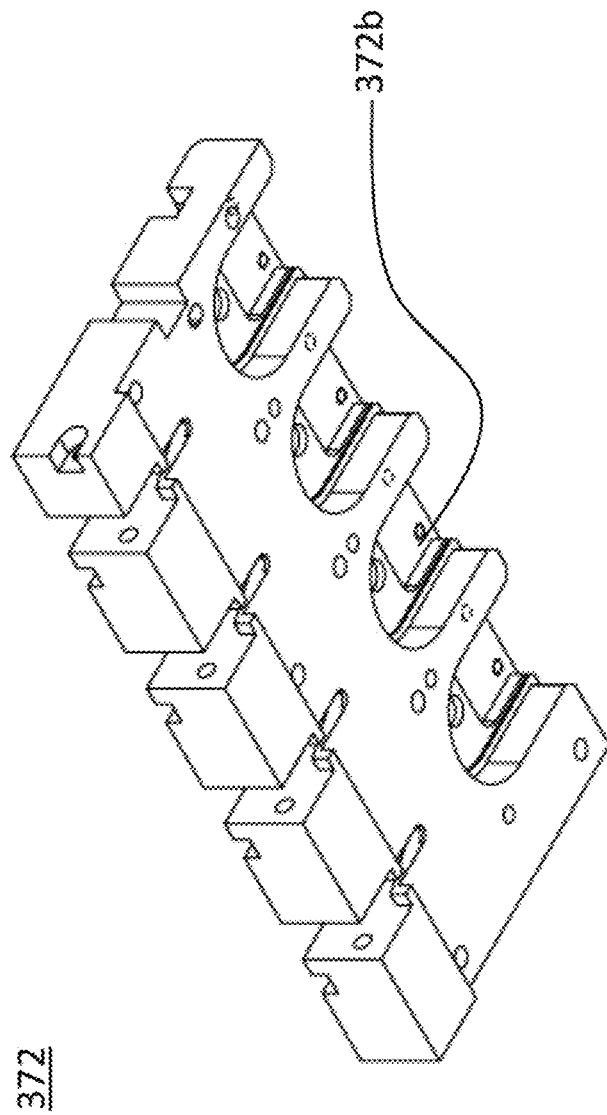
FIG. 41 is a bottom perspective view of the second plate of FIG. 40.

The second heating plate 372 is located above the first heating plate 371. Referring to FIGS. 40-41, the second heating plate 372 includes one or more actuator channels 372a formed in an upper surface thereof, which are each configured to receive a germinant release lever 401 (see FIG. 36). The germinant release levers 401 are configured to interact with the biological indicators 100 inserted in the respective BI bays to activate the germinant releaser 170 inside the BI 100, as discussed further below. The second heating plate 372 further includes a plurality of upper BI bays 372b formed in a lower surface thereof, which correspond to the BI bays 375 formed in the first heating plate 371.

According to embodiments, the upper surface of the second heating plate 372 may also include one or more actuator brackets (e.g., plate guides) 378 that respectively retain one or more actuators 400. In some embodiments, for example, the second heating plate 372 may include a plurality of separate actuator bracket(s) 378, one for each actuator 400. However, according to some embodiments, the second heating plate 372 includes a monolithic (or otherwise connected) actuator bracket construction in which the actuator brackets 378 are connected together (or formed as a monolithic unit) to form a bracket plate that supports and retains all of the actuators 400. The actuators 400 may be paired with respective solenoids 405 to each activate one of the germinant release levers 401, which interact with the BI 100 (when inserted in the respective BI bay) to actuate the germinant releaser 170, thereby releasing the germinant 165 into the interior of the BI housing 110. The germinant release lever 401 may include a cam surface 402 and a push rod 403. As discussed further below, when activated, the cam surface 402 may be rotated, translating its rotation into linear movement of the push rod 403 downwardly toward the biological indicator 100. The push rod 403 may have any suitable shape, e.g., a substantially cylindrical shape, and is configured to be inserted into the opening 121 in the first shell 120 of the BI housing 110. As the push rod 403 moves downwardly into the opening 121, the germinant releaser 170 is forced downward against the germinant releaser support 140, which in turn brings the germinant releaser 170 in contact with the germinant container 160, thereby rupturing the germinant container 160 and releasing the germinant 165 from the germinant container 160 onto the germinant pad 185.

Figure 43:
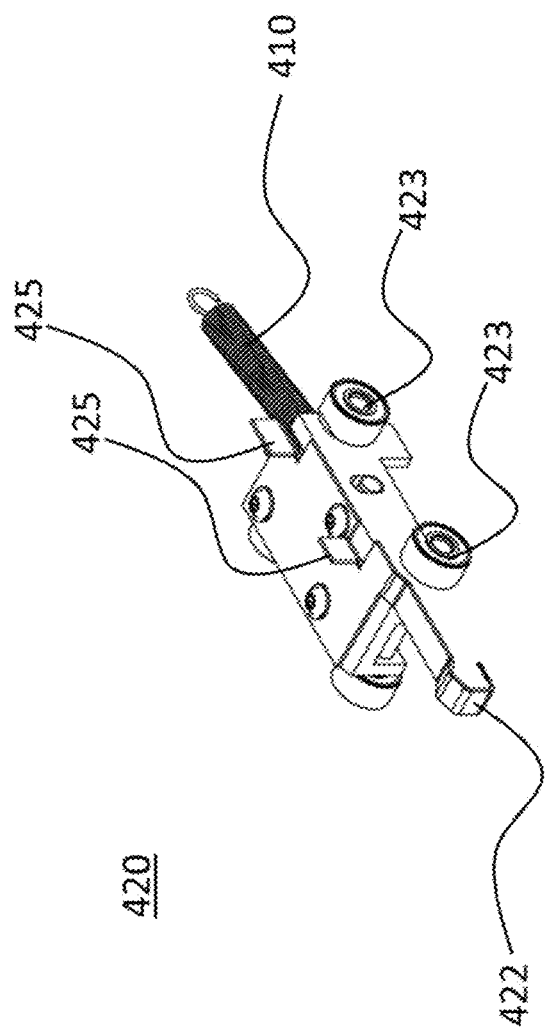
FIG. 43 is a perspective view of a shuttle of the heater block assembly of FIG. 35.
Figure 44:
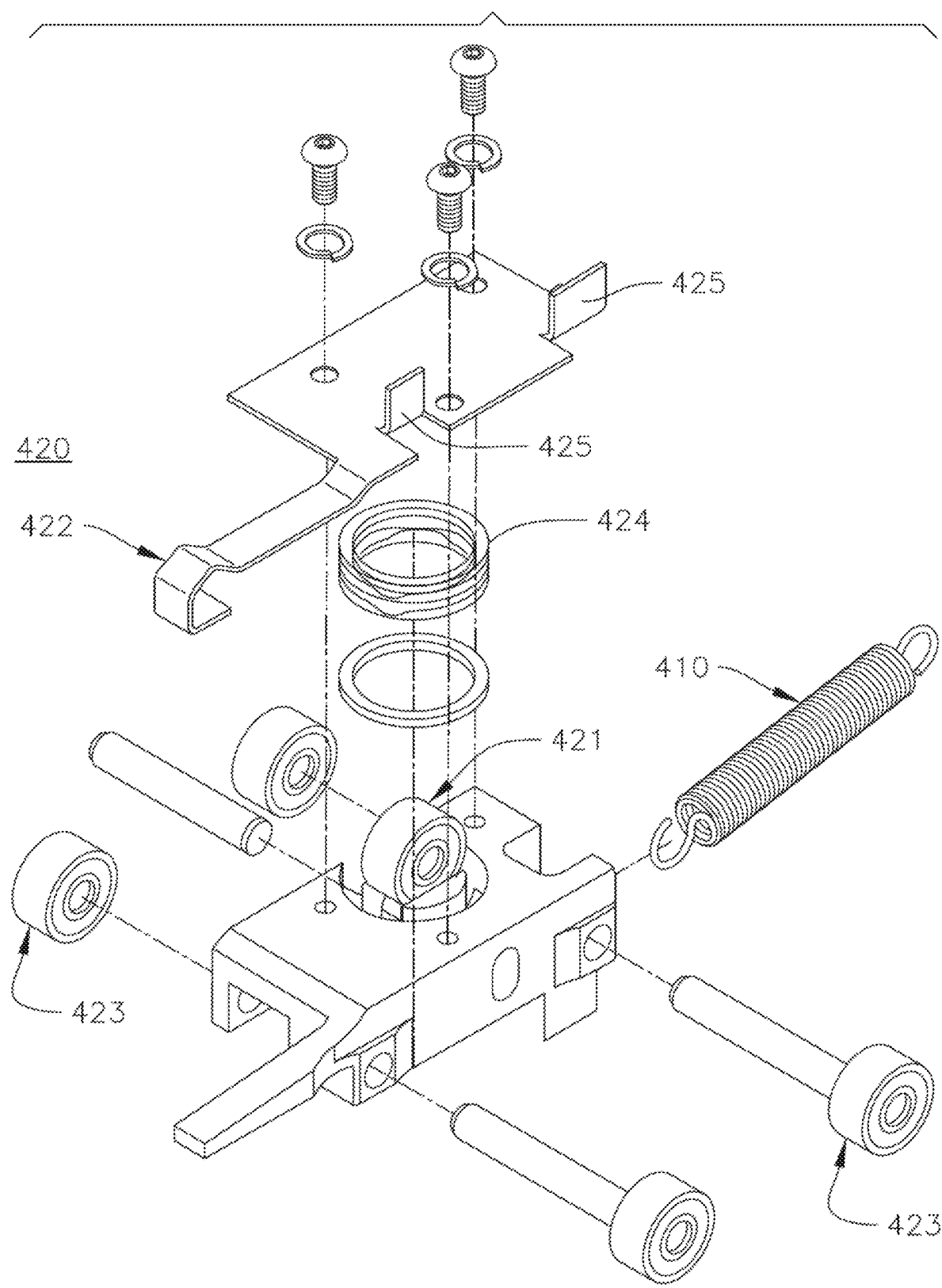
FIG. 44 is an exploded perspective view of the shuttle of FIG. 43.

According to some embodiments, the actuator 400 may include a shuttle 420 (see, e.g., FIGS. 43-44) that is configured to move linearly along a depth direction $Y_R$ of the BI reader 300. Each shuttle 420 may be retained by a respective actuator bracket 378 and connected to a shear wall (not shown) via a shuttle spring 410, which is tensioned to hold the shuttle 420 in position when the BI reader 300 is not activated. According to some embodiments, each of the actuators 400 may be activated by the corresponding solenoid 405. The solenoid 405 may activate the shuttle 420, driving the shuttle 420 toward the front panel 311. For example, a center rod 406 of the solenoid 405 may be driven toward the shuttle 420 along the depth direction $Y_R$ of the BI reader 300, overcoming the tension of the shuttle spring 410 and driving the shuttle 420 toward the front panel 311. The shuttle 420 may include a plurality of movement bearings 423 that function as wheels, which allow for relatively easy movement of the shuttle 420. As the shuttle 420 moves forward, a cam bearing 421 of the shuttle 420 interacts with the cam surface 402 of the germinant release lever 401, actuating the cam surface 402 in a clockwise direction. A wave spring 424 may surround the cam bearing 421, which applies contact pressure on the cam surface 402 as the cam bearing 421 rides over the cam surface 402. The push rod 403 then extends downwardly toward the BI bay 375 (and into the opening 121 in the BI housing 110). After completion of a test cycle, the solenoid 405 retracts the center rod 406, and the shuttle 420 is returned to its starting position by the shuttle spring 410, disengaging the germinant release lever 401 from the biological indicator 100. The solenoid 405 is not particularly limited, and may be any suitable solenoid capable of actuating the shuttle 420 as described herein. In some embodiments, for example, the solenoid 405 may be a push tubular solenoid, for example, a 1" dia.×2" push solenoid.

The BI reader 300 may include one or more sensors that monitor the location of the shuttle 420, such as a solenoid forward limit sensor, which senses whether the solenoid 405 is activated and the shuttle 420 is advanced (e.g., the center rod 406 is driven to the shuttle 420) and a solenoid return limit sensor, which senses whether the solenoid 405 is deactivated and the shuttle 420 is retreated (e.g., the center rod 406 is retracted). The solenoid forward limit sensor and the solenoid return limit sensor may provide a signal to the control system of the BI reader 300, to assist in determining whether the access door 313 of the BI bay 375 is locked or if the BI bay 375 is accessible.

Figure 45:
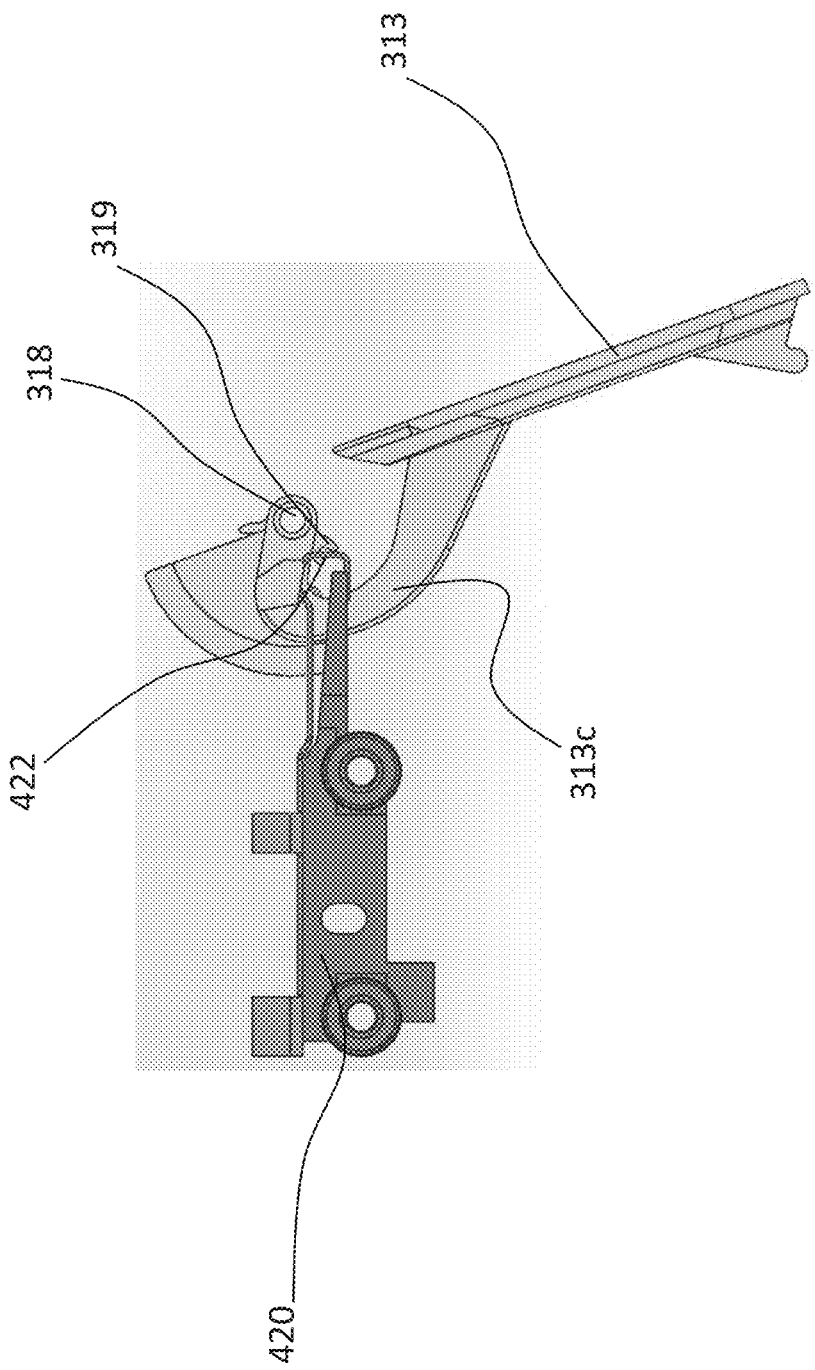
FIG. 45 is a side view of a shuttle having a door interlock spring and an access door of the biological indicator (BI) reader according to embodiments of the present disclosure.
Figure 46:
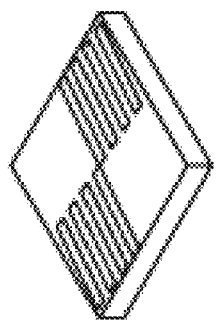
FIG. 46 is a bottom perspective view of a self-calibration target according to embodiments of the present disclosure.

The shuttle 420 may include a door interlock spring 422, which is configured to engage with a retaining clip 319 adjacent the pin 318 of the access door 313, as illustrated in FIG. 45. For example, the door interlock spring 422 may interact with the retaining clip 319 to prevent rotation of the access door 313 while the shuttle 420 is advanced toward the front panel 311. When the shuttle 420 is retracted toward the rear panel 391, the door interlock spring 421 moves away from the retaining clip 319, thereby unlocking the access door 313 at the hook portion 313*c*. The door interlock spring 422 provides an additional locking mechanism that prevents movement of the access door 313 during a test cycle of the BI reader 300.

Figure 42:
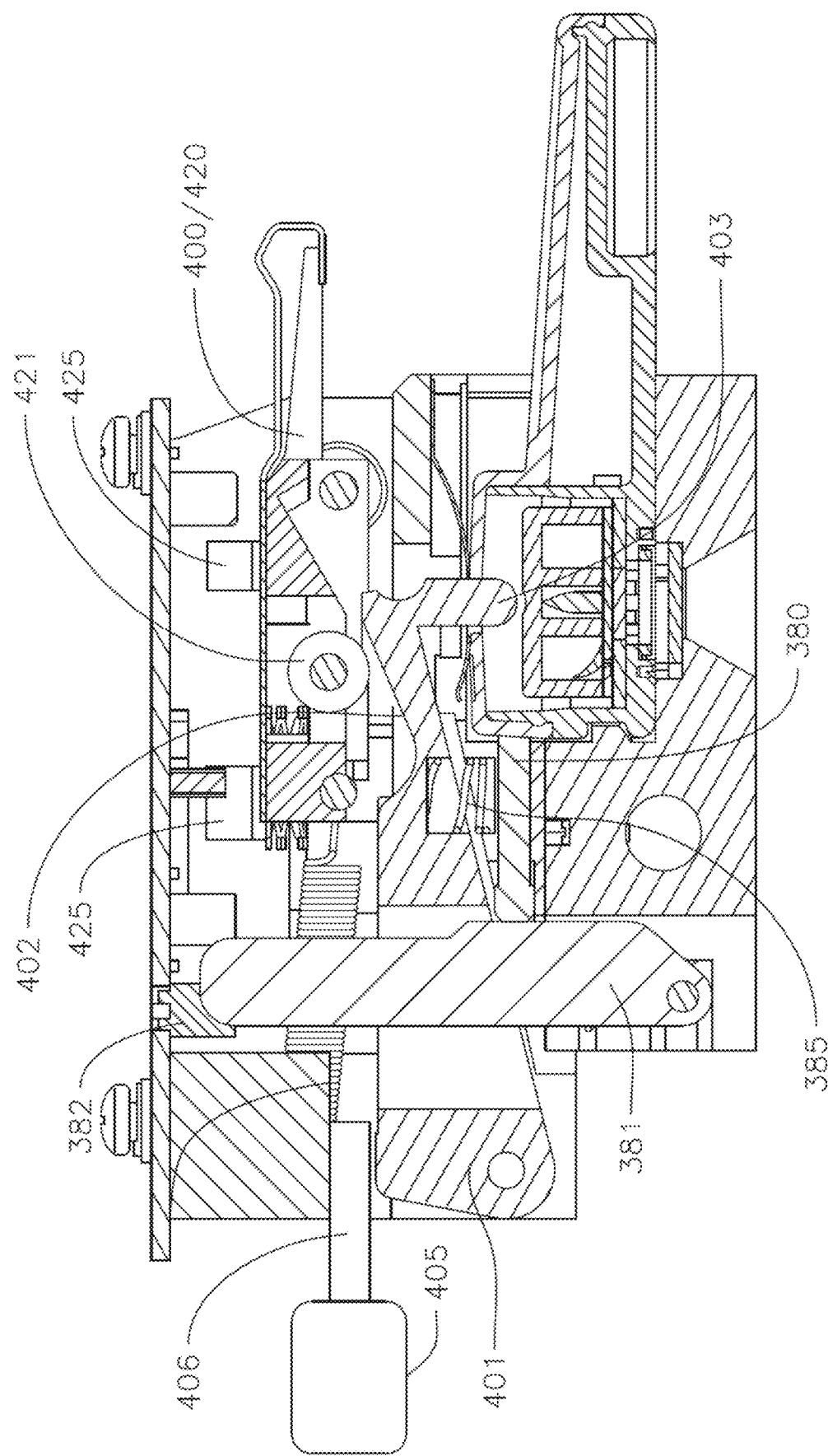
FIG. 42 is a side elevational view of a biological indicator (BI) bay of the heater block assembly of FIG. 35 after insertion of a biological indicator (BI) therein and during operation of the biological indicator (BI) reader.

The second heating plate 372 may further include a lever return spring 385 (see FIG. 42), which is tensioned to drive the germinant release lever 401 back to a starting position (and to move the push rod 403 up and out of the opening 121) when the actuator 400 is retracted.

The shuttle 420 may further include one or more shuttle flags 425 and/or corresponding sensors, which are used to communicate a location of the shuttle 420 to the control system of the BI reader 300. As such, the control system of the BI reader 300 may receive a signal from the shuttle flag/sensor 425 that the shuttle 420 has moved, indicating that the designated BI bay 375 has been actuated, which the control system may then use to signal that the BI bay 375 is active and/or to activate the optical assembly.

It will be appreciated that although the actuator 400 is described herein in connection with the shuttle 420, any suitable actuator or actuation mechanism that allows for activation of the germinant releaser 170 when the BI 100 is inserted in the BI bay 375 may be used, and the present disclosure is not limited to the specifically described actuator embodiments.

According to embodiments, the control system may include a lower BI sensor board 389 (shown in FIG. 36), which may be located above the actuator bracket(s) 378. The lower BI sensor board 389 may include sensors that are configured to detect the presence (or absence) of the biological indicator 100 in the BI bays 375 and/or to detect a location of the actuators 400. The lower BI sensor board 389 may be spaced apart from the second heating plate 372 via the actuator bracket(s) 378, thereby reducing the likelihood of damage to the lower BI sensor board 389 while the second heating plate 372 is heated (or held at an elevated temperature).

The heater block assembly 370 serves to heat the biological indicator 100 when it is inserted in the corresponding BI bay 375 to allow for germination of the spores 181. The heater block assembly 370 also provides datum locations for the biological indicator 100 for illumination and imaging of spore imaging areas inside the biological indicator 100. The heater block assembly 370 may include a self-calibration target 369 at a lower surface of the first heating plate 371, which allows for calibration of the positioning assembly 340 (discussed further below) and the heater block assembly 370. According to some embodiments, the self-calibration target 369 may include a substrate (e.g., soda lime glass) having a substantially square shape and offset, angled parallel striping, which may be utilized to calibrate the positioning assembly 340 during operation.

Figure 47:
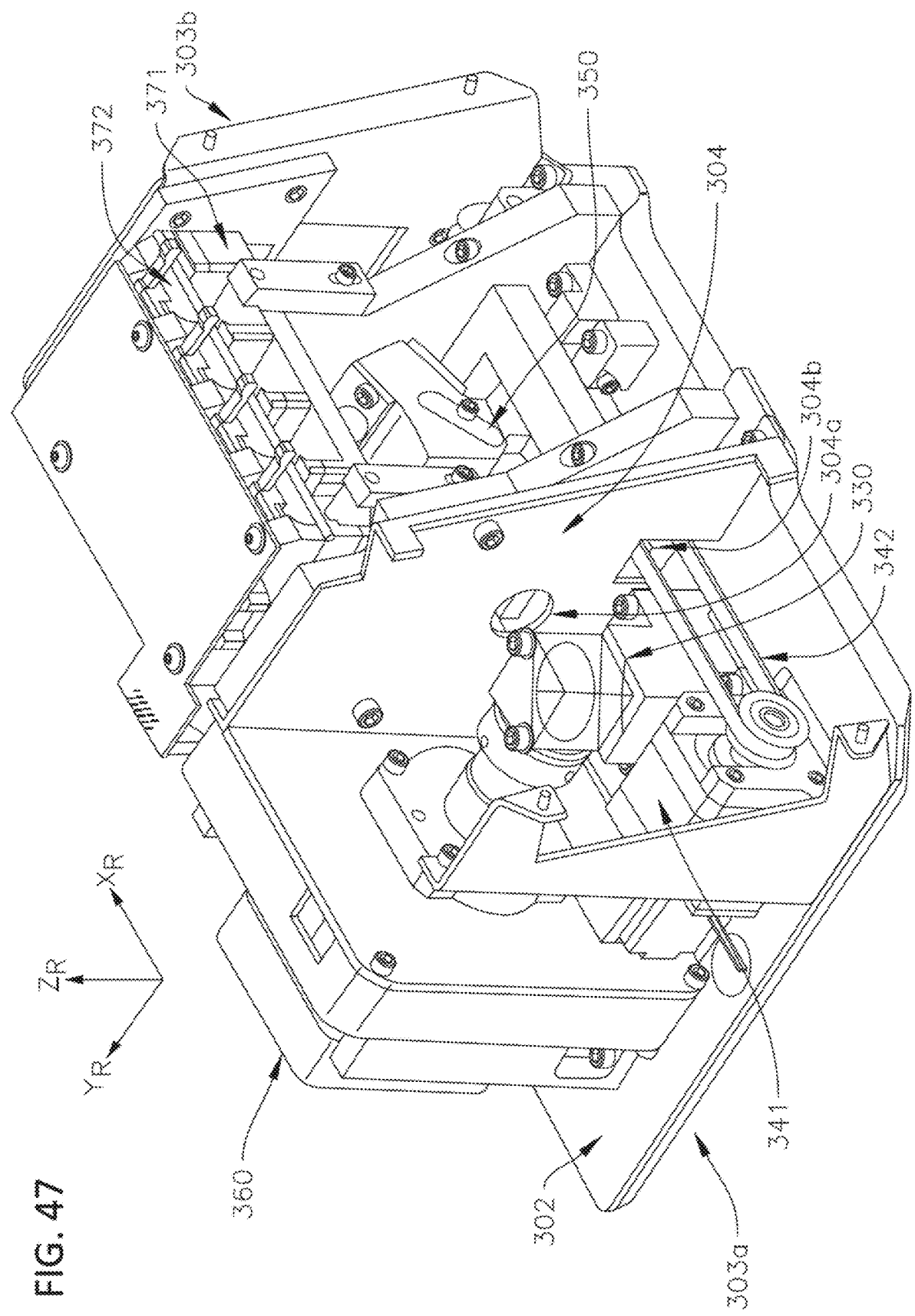
FIG. 47 is a perspective view of a heater block assembly, a positioning assembly, a mirror mount, and a camera assembly according to embodiments of the present disclosure.

As shown in FIG. 47, the heater block assembly 370 is located in an upper portion of the BI reader housing 301 (e.g., along a height direction $Z_R$ of the BI reader 300), and the positioning assembly 340 is located in a lower portion of the BI reader housing 301. However, the present disclosure is not limited to this configuration, and any configuration of the subassemblies of the BI reader 300 (including the heater block assembly 370 and positioning assembly 340) may be used so long as the BI reader can function as described herein.

Figure 48:
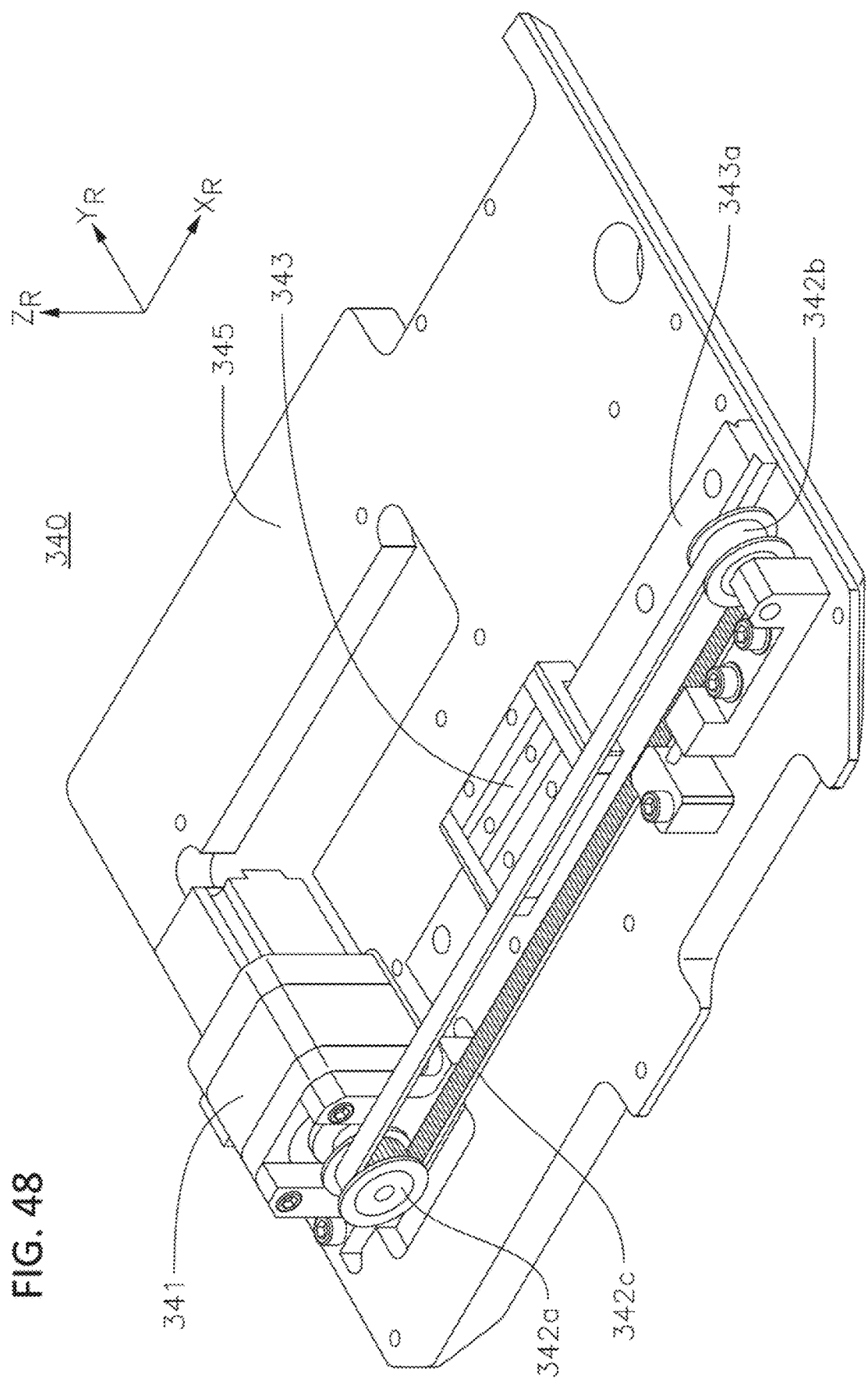
FIG. 48 is a perspective view of the positioning assembly of FIG. 47.
Figure 49:
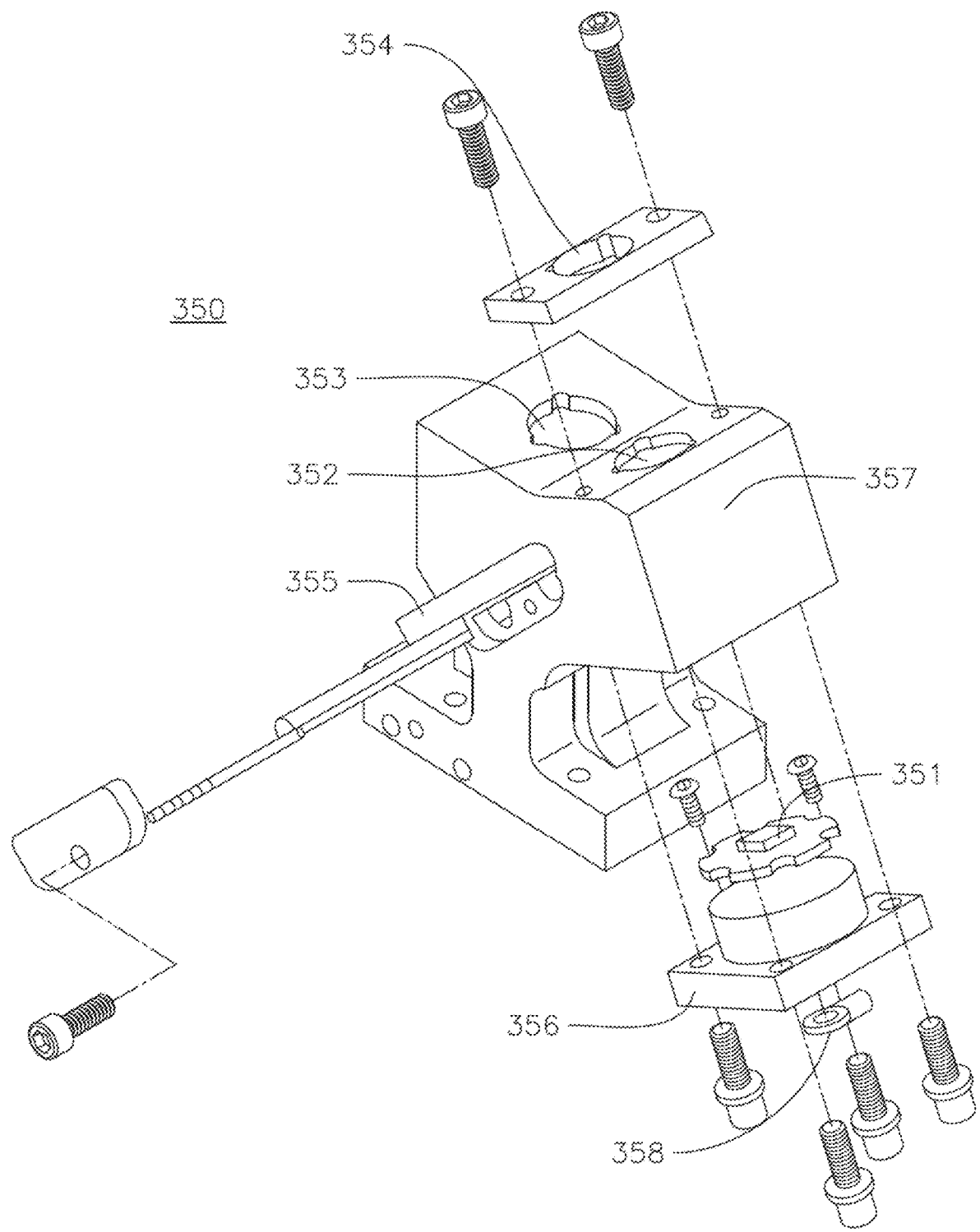
FIG. 49 is an exploded perspective view of a scan head assembly of the positioning assembly of FIG. 47.

Referring to FIGS. 48 and 49, the positioning assembly 340 includes a stepper motor 341 and belt drive 342 which move a scan head assembly 350 below the BI bays 375. The stepper motor 341 may drive the belt drive 342. The stepper motor 341 is not particularly limited, and may include any such motor capable of driving the belt drive 342. In some embodiments, for example, the stepper motor 341 may include a high torque motor with an integrated brake system, which is mounted on a deck 345 with a linear guide block 343 riding in a guide rail 343a adjacent thereto in a width direction $X_R$ of the BI reader 300. The belt drive 342 is also not particularly limited, and may have any suitable construction. In some embodiments, for example, the belt drive 342 may include a drive pulley 342a, an idler pulley 342b, and a timing belt 342c. The timing belt 342c and the linear guide block 343 may extend parallel to each other along the width direction $X_R$, such that as the belt drive 342 is driven by the stepper motor 341, the linear guide block 343 moves along the width direction $X_R$. According to some embodiments, the positioning assembly 340 may be configured to move a load at 60 mm per full revolution, however, the present disclosure is not limited thereto. According to embodiments, the stepper motor 341 may include a magnetic brake (e.g., an integrated magnetic brake), which prevents (or reduces the likelihood of) movement of the linear guide block 350 (on which the scan head assembly 350 is situated) when the BI reader 300 is not in use. According to embodiments, the timing belt 342c may be a circular tooth profile GT belt, but the present disclosure is not limited thereto, and the timing belt 342c may have any suitable construction. In use, the stepper motor 341 drives the driver pulley 342a causing it to rotate, which in turn causes the timing belt 342c to rotate around the idler pulley 342b and the linear guide block to translate linearly along the guide rail 343a.

According to some embodiments, the positioning assembly 340 may further include one or more threshold sensors to limit the movement of the scan head assembly 350 past one or more threshold limits. For example, in some embodiments, the positioning assembly 340 may include one sensor to the right of the scan head assembly 340, and another sensor to the left of the scan head assembly 340 to thereby limit movement of the scan head assembly 340 in both directions along the belt drive 342.

The scan head assembly 350 is mounted on the linear guide block 343. Referring to FIG. 49, the scan head assembly 350 includes an excitation source (e.g., an ultraviolet light emitting diode (UV LED) excitation source) 351, an emission lens (or an excitation focus lens) 352, a collection lens 353, an excitation filter 354, and a first mirror 355. The emission lens 352 and the collection lens 353 may be bonded (e.g., permanently bonded) in place using an adhesive (e.g., a UV curable adhesive) or any other suitable bonding means. The excitation source 351 is attached to a bracket 356, which is fastened to a scan head body 357, e.g., via screws. As such, the excitation source 351 may be actively aligned with the scan head assembly 350. According to embodiments, the first mirror 355 may be pressed to a datum using springs (e.g., urethane tubing springs). The scan head assembly 350 may further include a scan head temperature sensor 358 (e.g., a thermistor) at the scan head body 357, which monitors the temperature of the scan head assembly 350.

The excitation source 351 may be configured to emit light in the UV light wavelength range, i.e., in a wavelength range of about 100 to about 400 nm. In some embodiments, for example, the excitation source 351 may be configured to emit light in a range of about 200 to about 300 nm, or about 250 to about 300 nm. For example, in some embodiments, the excitation source 351 may have a peak wavelength of between about 270 nm and about 285 nm. The excitation filter 354 may have a center wavelength of between about 270 nm and about 370 nm, and for example may have a center wavelength of about 330 nm, and may be placed between the excitation source 351 and the imaging window 190 of the bioindicator 100. Light emitted from the excitation source 351 passes through the emission lens 352 and the excitation filter 354 of the scan head assembly 350 and through the imaging window 190 of the BI 100 to the spores 181 on the spore carrier 180 inside the biological indicator 100. Light emitted by the spores 181 is then emitted downwardly, back through the imaging window 190, the BI window 379 in the heater block assembly 370, the collection lens 353, and to the first mirror 355, which reflects the light along the width direction $X_R$ to a second mirror (e.g., a turning mirror) 331, which then reflects the light along the depth direction $Y_R$ to the camera assembly 360, which captures an image of the light.

More specifically, when the BI 100 is inserted into the reader, and the germinant 165 is released inside the BI 100, the photoluminescent component (e.g., Tb ions) may bind to any DPA released from the spores that were killed during the sterilization cycle. Additionally, any spores that were not killed by the sterilization process will begin to germinate on contact with the germinant component (e.g., L-alanine) of the germinant solution, which germination will cause those spores to also release DPA, which will in turn bind to the photoluminescent component and begin to luminescence in response to the light from the excitation source. When the spores (or more accurately, the DPA-photoluminescent complex) begin to luminesce, that luminescence is emitted back through the imaging window 190 of the BI along the optical path described above to the camera assembly 360, which captures images of the luminescence. The BI reader 300 analyzes the images captured by the camera assembly 360 to determine whether any of the spores 181 survived the sterilization cycle, as discussed further below. In particular, in some embodiments, the BI reader 300 detects a static background level of DPA from the luminesce returned by spores that were killed during the sterilization process. If any spores were not killed during the sterilization process, they will germinate upon contact with the germinant solution 165, and will release DPA upon germination, which the BI reader 300 will detect as a DPA signal above the static background level (when present). And the BI reader 300 will associate any DPA signal above the static background level, or any DPA signal occurring after a predetermined period of time after BI activation, with failure of the sterilization process.

The emission lens 352 may be located between the excitation source 351 and the excitation filter 354 to disperse the light emitted from the excitation source 351. According to embodiments, the emission lens 352 may be a double-convex lens having a UV-AR coating. According to embodiments, the emission lens 352 may include a fused silica with a design wavelength of between approximately 250 nm and approximately 425 nm. According to embodiments, the emission lens 352 may have a 12 mm diameter, a 12 mm focal length, and a 9¼ mm back focal length.

Figure 50:
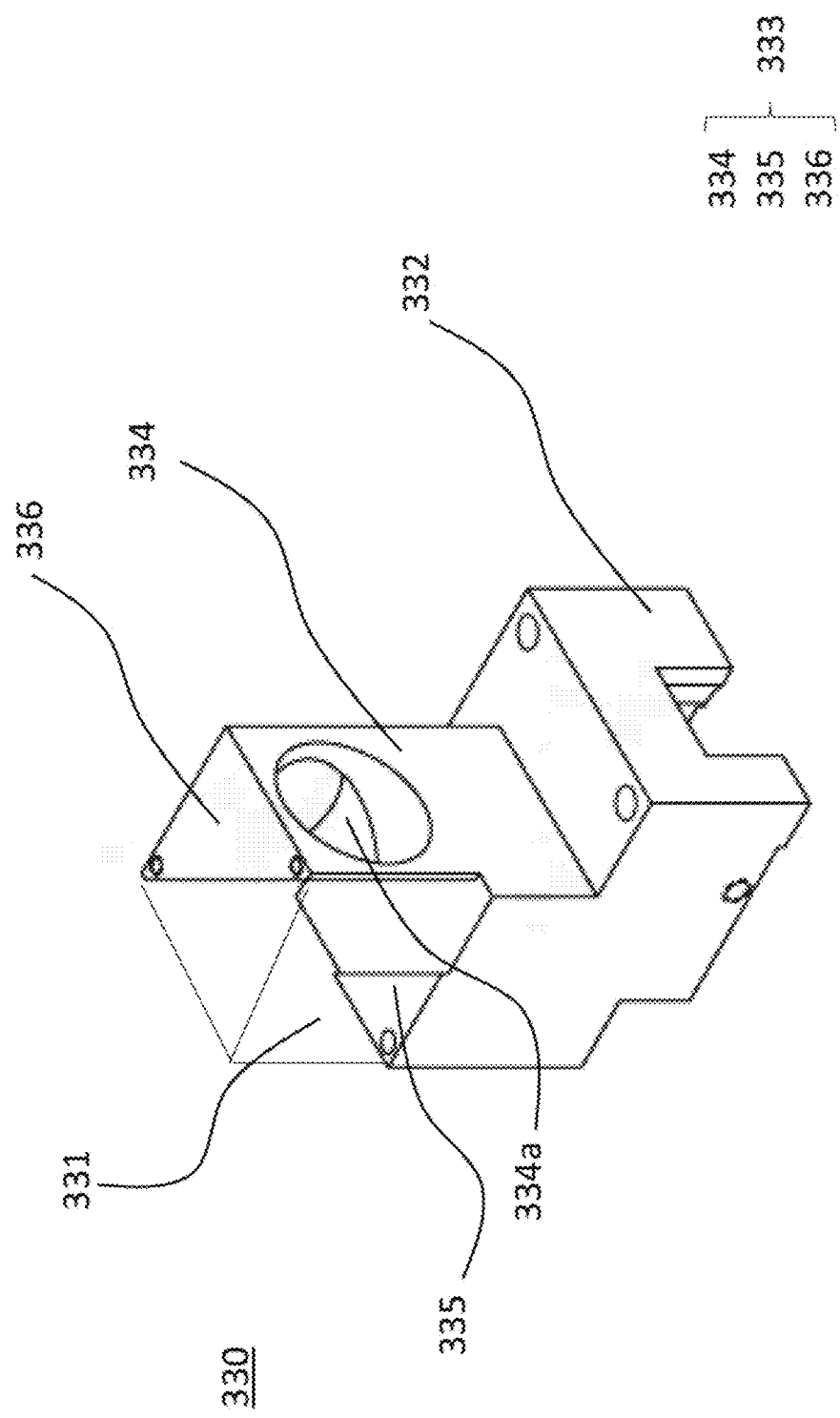
FIG. 50 is a perspective view of the mirror mount of FIG. 47.
Figure 51B:
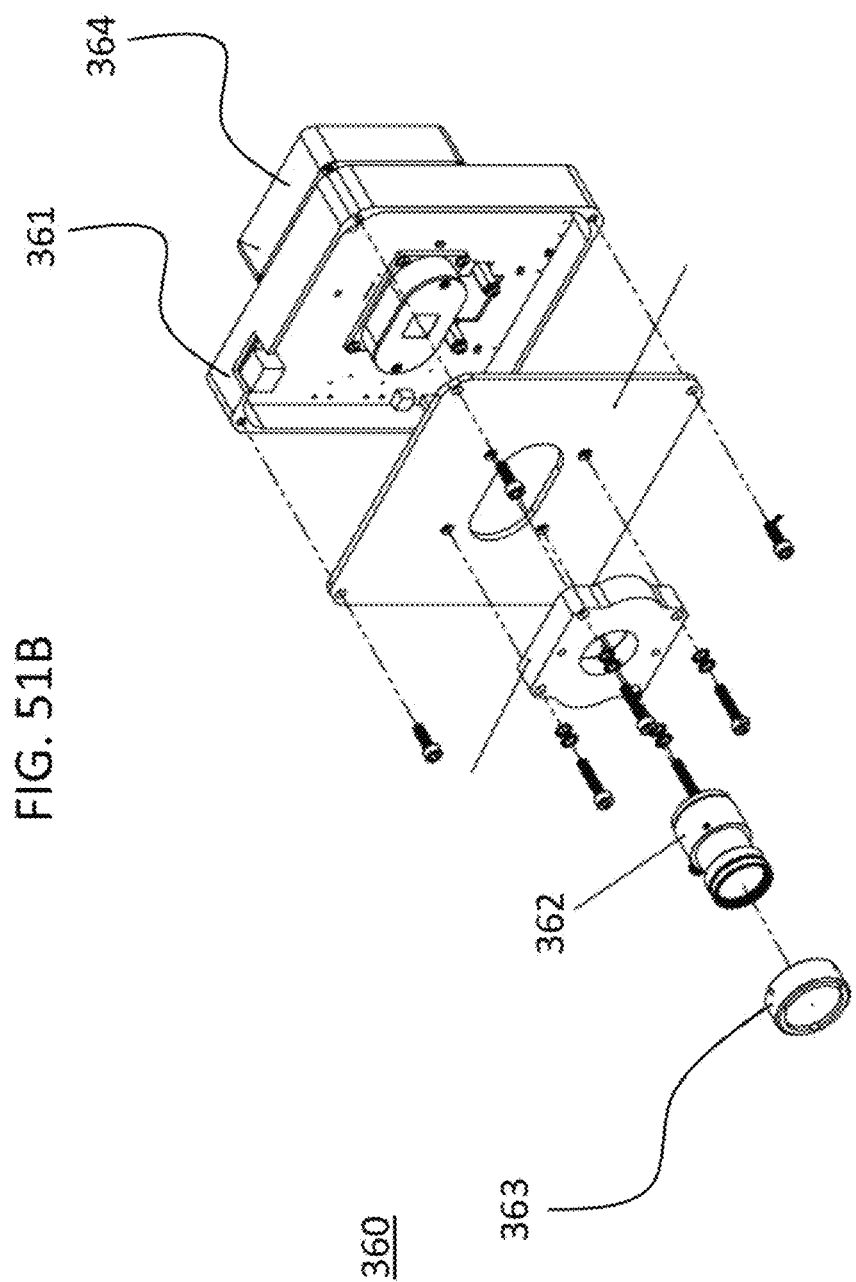
FIG. 51B is an exploded perspective view of the camera assembly of FIG. 51A.

According to one or more embodiments, the scan head assembly 350 is mounted on the linear guide block 343, which moves along the guide rail 343a which is aligned beneath the BI bays 375. The first mirror 355 is located on the bracket 357, and is oriented (or aligned) such that the first mirror 355 reflects light along the width direction $X_R$ to the second mirror 331 on a mirror mount 330 (see, e.g., FIG. 47 and FIG. 50), thereby relaying a collimated emission ray from the scan head assembly 350 to the camera assembly 360. The camera assembly 360 is attached to a bottom plate 302 of the BI reader housing 301, e.g., via mounting brackets. The camera assembly 360 is located in a pocket edge of the bottom plate 302. While the scan head assembly 350, camera assembly 360, and optical path are described above with reference to particular locations and directional light paths, it is understood that these components can be alternately positioned or located so long as the resulting optical path is capable of delivering light from the scan head assembly 350 to the spore carrier 180, and returning the luminescence from the spore carrier to the camera assembly 360.

Referring to FIG. 47, in some embodiments, the linear guide block 343 is separated from the mirror mount 330 by a central panel 304 that extends along the width direction $X_R$. The central panel 304 may define a first opening 304a aligned with the first mirror 355 and the second mirror 331, which allows light to be reflected from the first mirror 355 to the second mirror 331. The central panel 304 may also define a second opening 304b to accommodate the timing belt 342c.

In some embodiments, the mirror mount 330 is stationery and may be located adjacent to the belt drive 342. The mirror mount 330 may be mounted on the deck 345 between the stepper motor 341 and the scan head assembly 350, for example, between the stepper motor 341 and the central panel 304. According to embodiments, the mirror mount 330 may be aligned with the scan head assembly 350 along the width direction $X_R$ and aligned with the camera assembly 360 along the depth direction $Y_R$, and is therefore configured to reflect light from the scan head assembly 350 to the camera assembly 360.

The mirror mount 330 may have any suitable configuration such that the mirror mount 330 may receive the second mirror (turning mirror) 331 and reflect light from the scan head assembly 350 to the camera assembly 360. For example, referring to FIG. 50, the mirror mount 330 may include a base portion 332 and a bracket portion 333. The base portion may have any suitable height such that the second mirror 331 is properly aligned with the scan head assembly 350 along the height direction $Z_R$ to deliver light to the camera assembly 360. The bracket portion 333 is configured to receive and hold the second mirror 331, and may have a pair of connecting side walls 334, a generally triangular shaped upper wall 336, and a base 335 on which the second mirror 331 sits. The side walls 334 each have an opening 334a that allows light to pass therethrough and onto the second mirror 331. The second mirror 331 may have a triangular prism shape (e.g., a right angle mirror) and may include a silver coated N-BK7 substrate, though the present disclosure is not limited thereto, and the second mirror may have any suitable shape and construction.

Referring to FIGS. 51A, 51B, 52A, and 52B, the camera assembly 360 may include a camera 361, an optical lens 362, a filter 363, and a camera fan 364 and Peltier assembly 365 (for keeping the camera at safe operating temperatures).

According to embodiments, the camera assembly 360 may be located in a fixed position relative to the BI housing 301, and at the end of the optical path described above for receiving the luminescence from the spores. This configuration (i.e., a moving scan head assembly and a fixed camera assembly) enables use of only one camera 361 to analyze multiple bays. However, the present disclosure is not limited to this configuration, and the BI reader 300 may instead include a camera 361 for each BI bay 375. In such embodiments, the BI reader 301 may also include a scan head assembly 350 for each BI bay, and both the scan head assemblies 350 and the cameras 361 may be fixed in position beneath their respective BI bay 375. As will be appreciated, such a multiple-camera, multiple-scan head construction would eliminate the need for the positioning assembly 340 and simplify the optical path from the imaging window 190 of the BI to the camera (as the turning optics (i.e., the first and second mirrors and the mirror mount) would no longer be necessary), but would significantly increase the cost and size of the reader.

According to example embodiments, the camera 361 may be a thermoelectrically (TE)-cooled charge-coupled device (CCD) camera. For example, in some embodiments, the camera 361 may be a high-power camera, meaning that it allows for an imaging rate (or frame frequency) of about 5 kHz to about 10 kHz, which allows for effective imaging of the lifetime of the fluorescence signal of the spores 181. The camera 361 may be configured to operate in a time-gated mode for capturing long living luminescence of the spores 181 when excited with UV (e.g., UVC) radiation by flashing UV light and exposing the camera 361 using electronic shutter at regular intervals. The camera 361 may also be configured to operate in a bright image mode for a variable exposure at a frequency of between about 1 ms to 2000 ms. The optical lens 362 is connected to the camera 361. The optical lens 362 may, for example, have a focal length (FL) of 35 mm and a minimum working distance of 165 mm (f/1.65) (i.e., a minimum working distance of 165 mm or greater). The filter 363 is connected to the lens 362. The filter 363 may be a band pass filter, for example a filter between about 534 nm to about 566 nm. In some embodiments, the filter 363 may be a 550 nm band pass filter.

Referring to FIGS. 52A-52B, the Peltier assembly 365 may be mounted to the camera 361, and the fan 364 may be mounted to the Peltier assembly 365 to cool the camera 361. According to embodiments of the present disclosure, a camera guard 366 having a plurality of openings 367 may be attached to the fan 364 to reduce the likelihood of any foreign objects entering the fan 364 and the Peltier assembly 365. The Peltier assembly 365 may be utilized to improve performance of the fan 364, e.g., to improve heat transfer characteristics while the fan 364 cools the camera 361. According to embodiments, the fan 364 may include a 40×40×20 24 VDC VAPO® 7.7 CFM fan (VAPO® is a registered trademark of Sunonwealth Electric Machine Industry, Co.). The guard 366 may be attached to the fan 364, and may be made of a durable material, such as a metal. For example, the guard 366 may include an aluminum alloy. The openings 367 may be formed radially, for example, the guard 366 may include 12 of the openings 367, with symmetrical rounded wedge shapes. However, it is understood that the guard 366 is not limited thereto, and can have any suitable configuration and any suitable number and shape of the openings 367.

Figure 53:
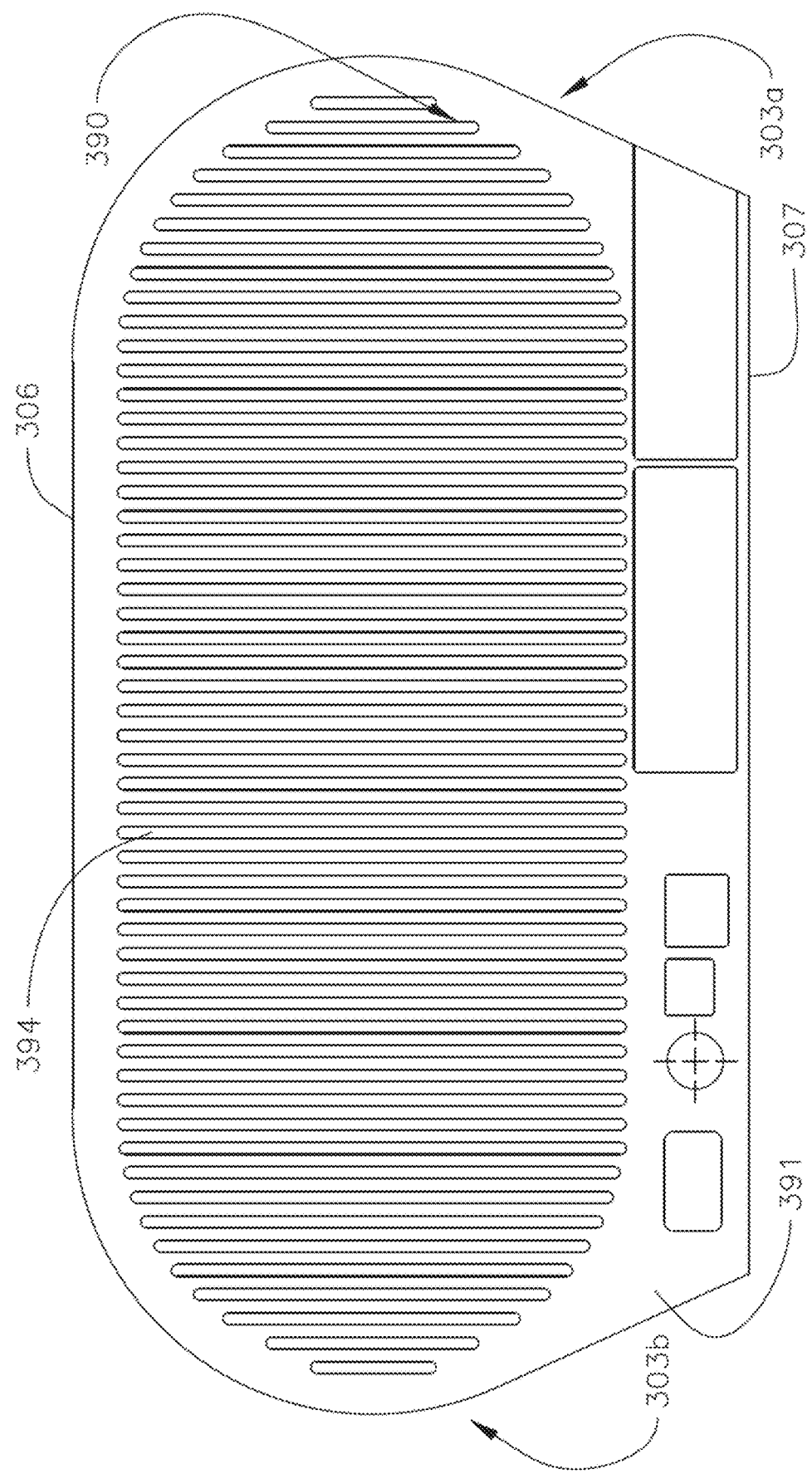
FIG. 53 is a back elevational view of the biological indicator (BI) reader of FIG. 29.
Figure 54:
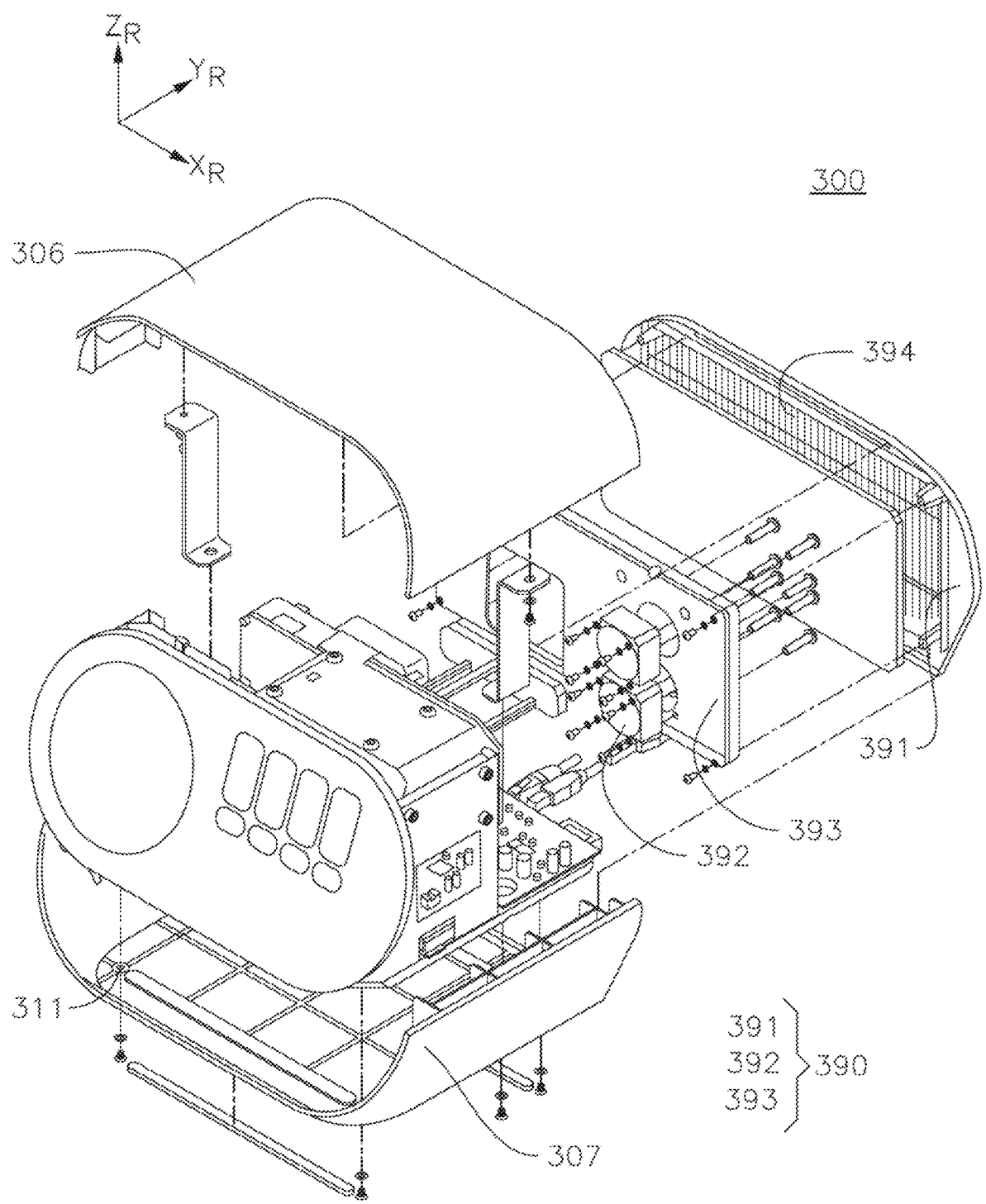
FIG. 54 is an exploded perspective view of the biological indicator (BI) reader of FIG. 29.

Referring to FIGS. 53-54, the BI reader housing 301 further includes an upper housing panel 306 at a top thereof and a lower housing panel 307 below the bottom plate 302 and at a bottom of the BI reader 300. The upper housing panel 306 and the lower housing panel 307 may each have a substantially U-shaped profile such that the upper housing panel 306 and the lower housing panel 307 extend along the height direction $Z_R$ of the BI reader 300 and mate with each other, forming the sides of the BI reader housing 301.

The rear panel assembly 390 includes a rear panel 391, one or more axial fans 392, and an air intake plenum 393. As illustrated in FIG. 53, the rear panel 391 may have a plurality of perforations 394 that permit air flow therethrough. The shape and number of the perforations 394 is not particularly limited, and may be any shape and number so long as the perforations 394 allow a sufficient amount of air flow through the rear panel 391. For example, in some embodiments, as shown in FIG. 53, the perforations 394 may take the shape of vertical slots such that the rear panel 391 resembles a grate. The axial fans 392 and the air intake plenum 393 each allow for the intake of air into the BI reader 300, which may then exit through vents below the front panel 311. For example, ambient air may be drawn from an area behind the BI reader 300 into the BI reader 300 through the rear panel assembly 390. Positive pressure is then built inside the BI reader 300, which expels warm air through the vents at the front panel assembly 310. As an example, one of the axial fans 392 may be located directly adjacent the camera 361, and two other axial fans 392 may be located near the heater block assembly 370 and provide additional air flow. As such, the amount of dust and other particulates in the system may be reduced. The axial fans 392 may be used to maintain a suitable temperature of the BI reader 300 for the components contained therein, for example, to keep the camera 361 at a suitable operating temperature while being used in close proximity to the heater block assembly 370.

Turning back to FIG. 47, according to embodiments, the heater block assembly 370 is located above the linear guide block 434. As discussed above, the central panel 304 defines the second opening 304b that accommodates the timing belt 343. The stepper motor 341 and the drive pulley 342a may be located between a first side 303a of the BI reader housing 301 and the central panel 304, and the idler pulley 342b and the linear guide block 343 (as well as the scan head assembly 350 mounted on the linear guide block 343) may be located between a second side 303b of the BI reader housing 301 and the central panel 304. The heater block assembly 370 may be supported between the second side 303b and the central panel 304 so that it is located on the same side of the BI reader 300 as the linear guide block 343. The camera assembly 360 and the mirror mount 330 are both located between the first side 303a and the central panel 304.

According to embodiments, the BI reader 300 includes four access doors 313 which respectively correspond to four BI bays 375 spaced apart from each other along the width direction $W_R$ of the BI reader 100. As such, the BI reader 300 can perform sterilization efficacy testing on four biological indicators 100 concurrently (or simultaneously) during one detection cycle of the BI reader 300.

Figure 55:
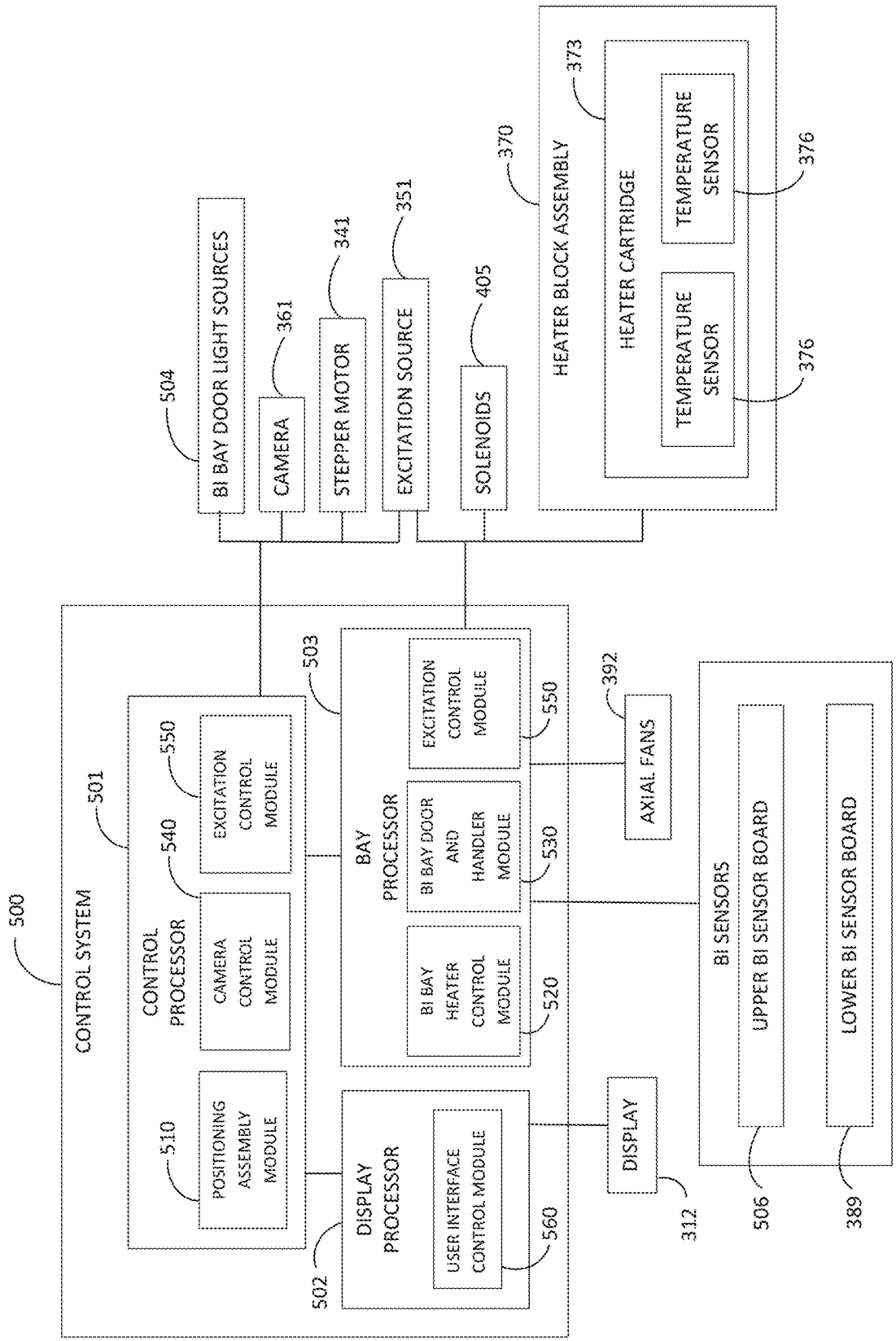
FIG. 55 is a schematic diagram of a control system according to embodiments of the present disclosure.

FIG. 55 depicts a block diagram of a control system according to embodiments of the present disclosure. According to some embodiments, the control system 500 may be configured to operate the positioning assembly 340, the heater block assembly 370, the access doors 313 and solenoids 405, the camera assembly 360, the excitation source 351 and scan head assembly 350, the display 312, etc. of the BI reader 300. In some embodiments, the control system 500 may include a plurality of microcontrollers (or processors) that run one or more modules configured to control different aspects of the BI reader 300. For example, the one or more processors of the control system 500 may run a positioning assembly control module 510, a BI bay heater control module 520, a BI bay door and handler control module 530, a camera control module 540, an excitation control module 550, and a user interface control module 560. For example, in some embodiments, the one or more controllers of the control system 500 may include a control processor 501, a bay processor 503 and a display processor 502, each of which may operate one or more of the positioning assembly control module 510, BI bay heater control module 520, BI bay door and handler control module 530, camera control module 540, excitation control module 550, and user interface control module 560.

Figure 56:
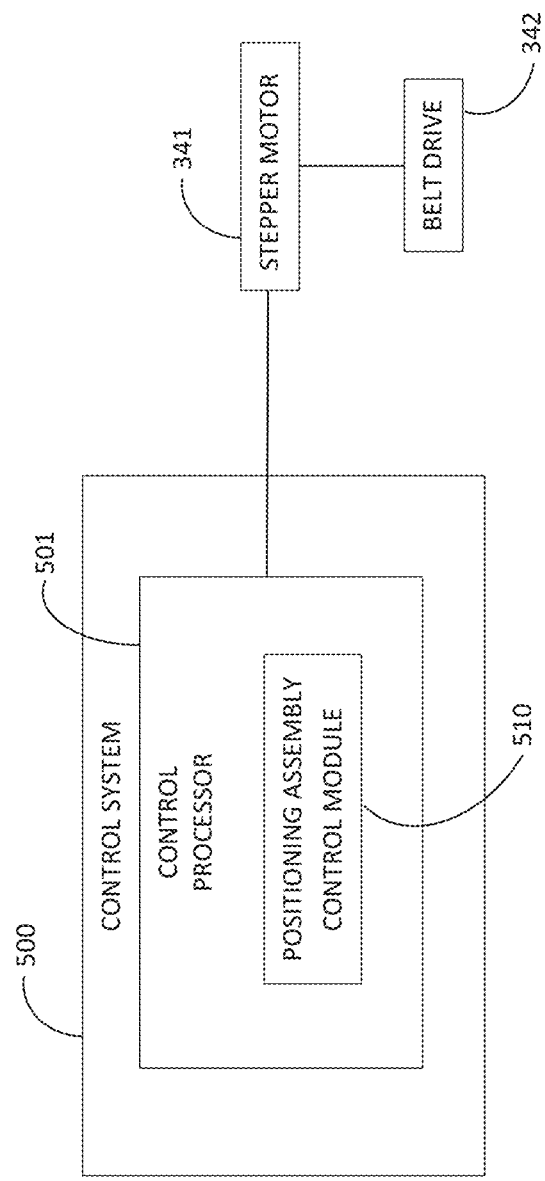
FIG. 56 is a schematic diagram of a positioning assembly control module within the control system according to embodiments of the present disclosure.

In some embodiments, as shown generally in FIGS. 55 and 56, the positioning assembly control module 510 may be configured to control the positioning assembly 340. For example, the positioning assembly control module 510 may run the stepper motor 341 and the belt drive 342. Additionally, in some embodiments, the positioning assembly control module 510 may include lock-out logic to prevent the positioning assembly 340 from advancing the scan head assembly 350 past a preset threshold limit (as discussed further below in connection with the bay processor, and above in connection with the positioning assembly 340). In some embodiments, the positioning assembly control module 510 may be run by the control processor 501, as discussed more below.

Figure 57:
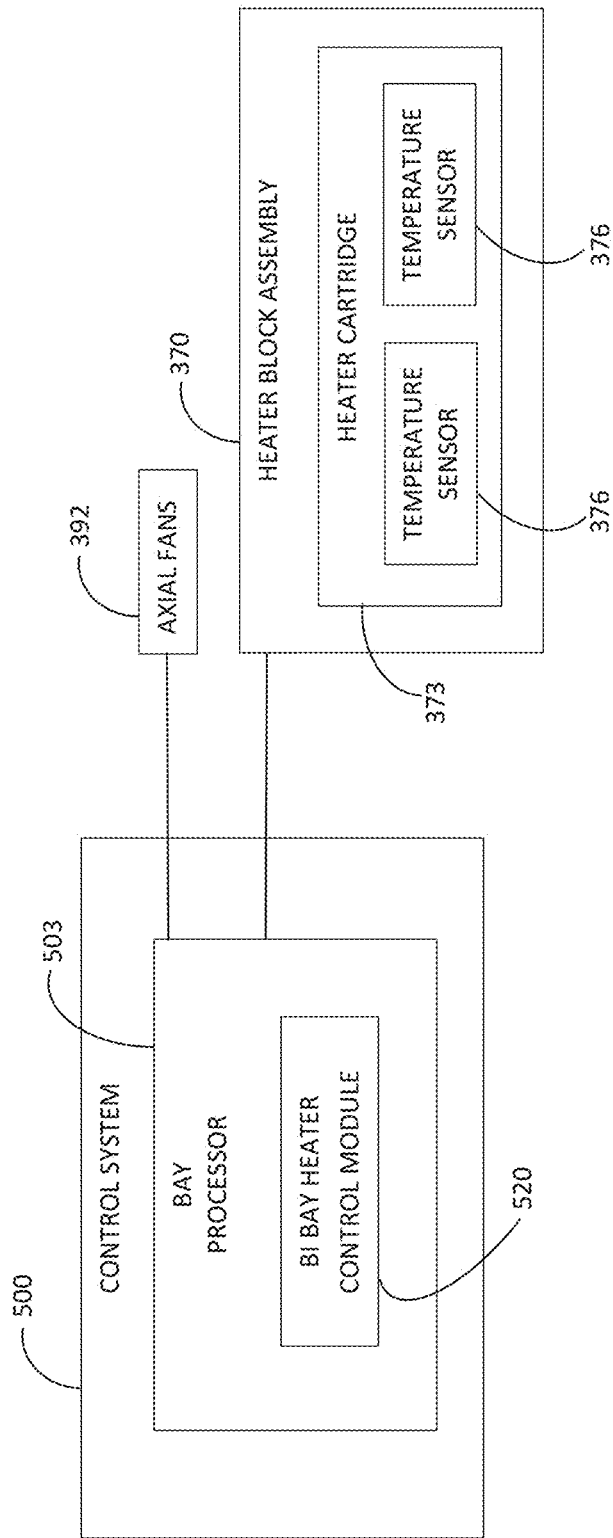
FIG. 57 is a schematic diagram of a biological indicator (BI) bay heater control module within the control system according to embodiments of the present disclosure.

As shown in FIGS. 55 and 57, the BI bay heater control module 520, according to some embodiments, may be configured to control the heater cartridge 373 of the heater block assembly 370 and the axial fans 392, and receive and process signals from the temperature sensors 376 of the heater block assembly 370. The BI bay heater control module 520 may further include logic to inhibit continued operation of the heater cartridge 373 if the temperature sensor(s) 376 register a temperature difference above a preset threshold. The BI bay heater control module 520 may further run a heater current monitor, and include logic to inhibit continued operation of the heater if the heater current monitor registers a current exceeding a preset threshold. In some embodiments, the BI bay heater control module 520 may be run by the bay processor 503, as discussed more below.

Figure 58:
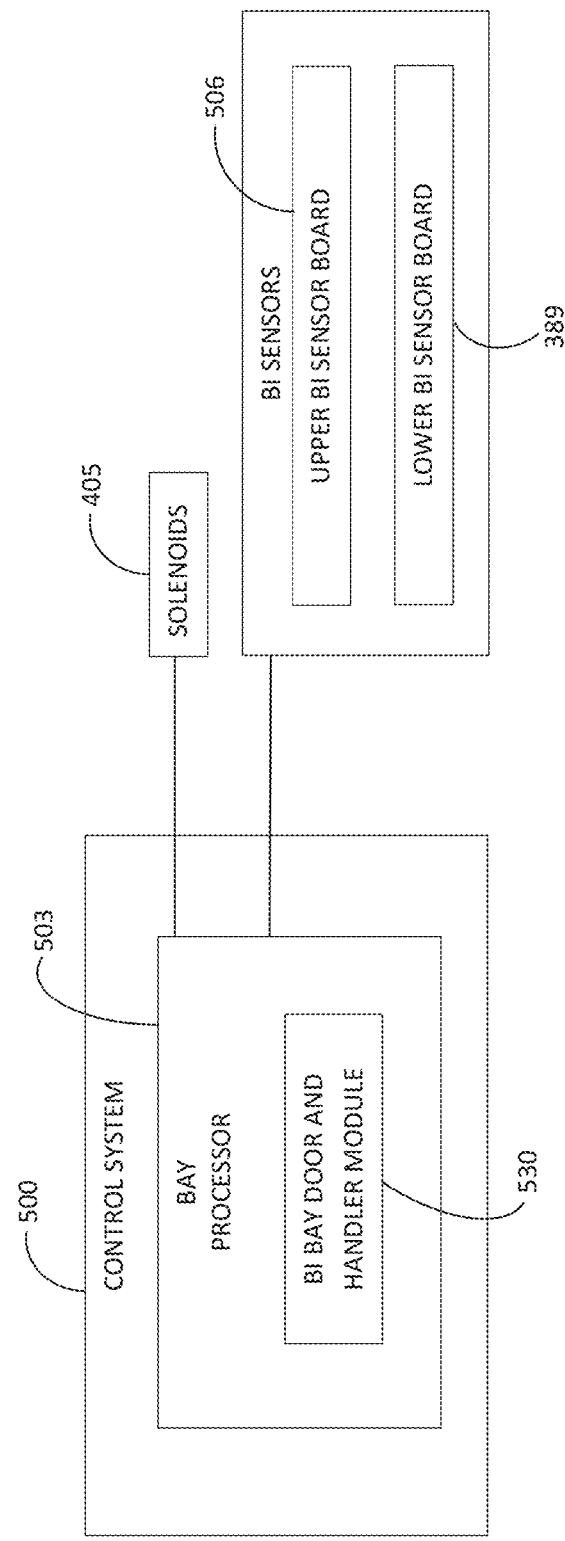
FIG. 58 is a schematic diagram of a biological indicator (BI) bay door and handler control module within the control system according to embodiments of the present disclosure.

In some embodiments, as shown in FIGS. 55 and 58, the BI bay door and handler control module 530 may be configured to control the solenoids 405. This module may further communicate with one or more sensors within each BI bay for detecting various conditions. In some embodiments, the BI bay door and handler control module 530 may communicate with these sensors via one or more BI sensor boards (e.g., an upper BI sensor board 506 and lower BI sensor board 505). For example, in some embodiments, the BI bay door and handler control module 530 may communicate with one or more of a door position sensor, a solenoid forward limit sensor, a solenoid return limit sensor, or a BI presence sensor. Each of these sensors may be an infrared photo-interrupter, as discussed above, and each of the BI bays may include one, any combination of two or more, or all of these sensors. In some embodiments, the BI bay door and handler module 530 may be run by the bay processor 503.

Figure 59:
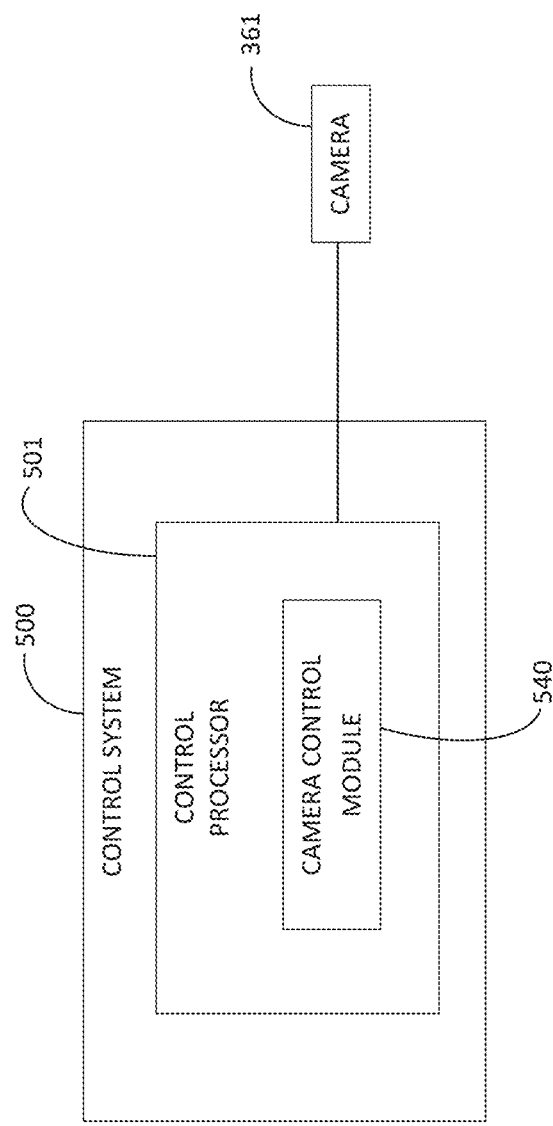
FIG. 59 is a schematic diagram of a camera control module within the control system according to embodiments of the present disclosure.

As shown in FIGS. 55 and 59, the camera control module 540, according to embodiments, may be configured to control the camera 361. For example, the camera control module 540 may be configured to operate the camera, and receive and process the images received by the camera 361.

In some embodiments, the camera control module 540 may be run by the control processor 501.

Figure 60:
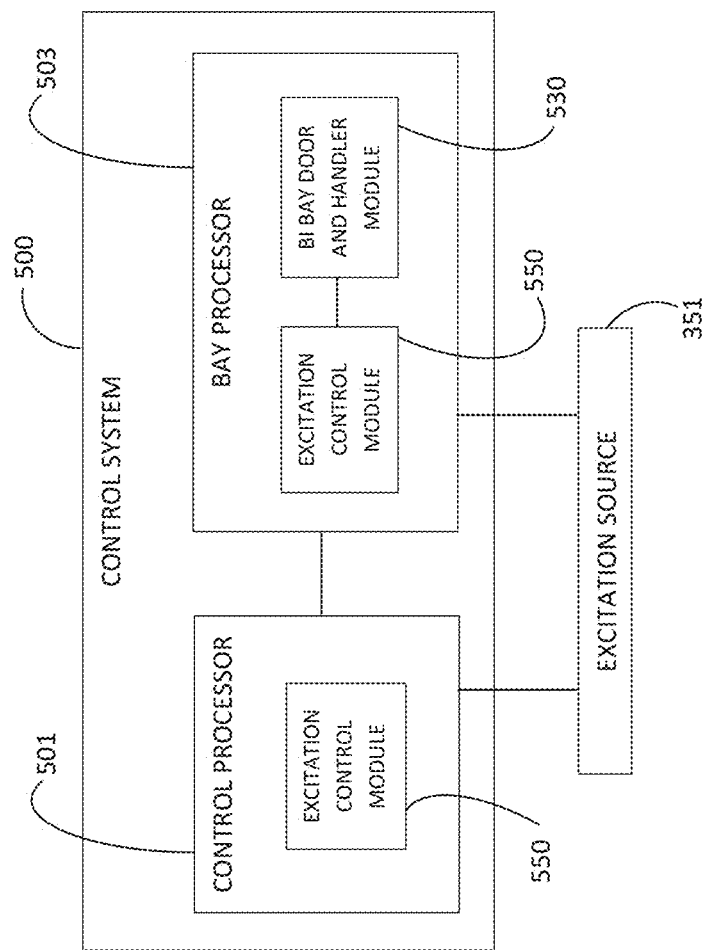
FIG. 60 is a schematic diagram of an excitation control module within the control system according to embodiments of the present disclosure.

According to some embodiments, as shown in FIGS. 55 and 60, the excitation control module 550 may be configured to operate the excitation source 351. In some embodiments, the excitation control module 550 may be configured to receive input from the BI bay door and handler module 530 regarding, for example, signals indicative of which of the BI bays 375 are occupied by a BI 100. The excitation control module 550 may process that input to determine which of the BI bays 375 require excitation source turn-on, and which of the BI bays 375 can be skipped in a particular run (e.g., because a particular BI bay 375 does not have a biological indicator 100 inserted therein). The excitation control module 550 may also operate a built-in mechanism to regulate the current of the excitation source 351 to maintain current regulation through cycles (e.g., PWM cycles) of the excitation source 351. The excitation control module 550 may also be configured to control the timing of excitation source turn-on and its length of exposure, and the timing of camera turn-on and its length of exposure. In some embodiments, aspects of the excitation control module 550 may be run by the control processor 501, and other aspects of the excitation control module 550 may be run by the bay processor 503. However, the present disclosure is not limited thereto, and it is understood that the excitation control module 550 may be run by a single processor (e.g., either the control processor 501 or the bay processor 503).

Figure 61:
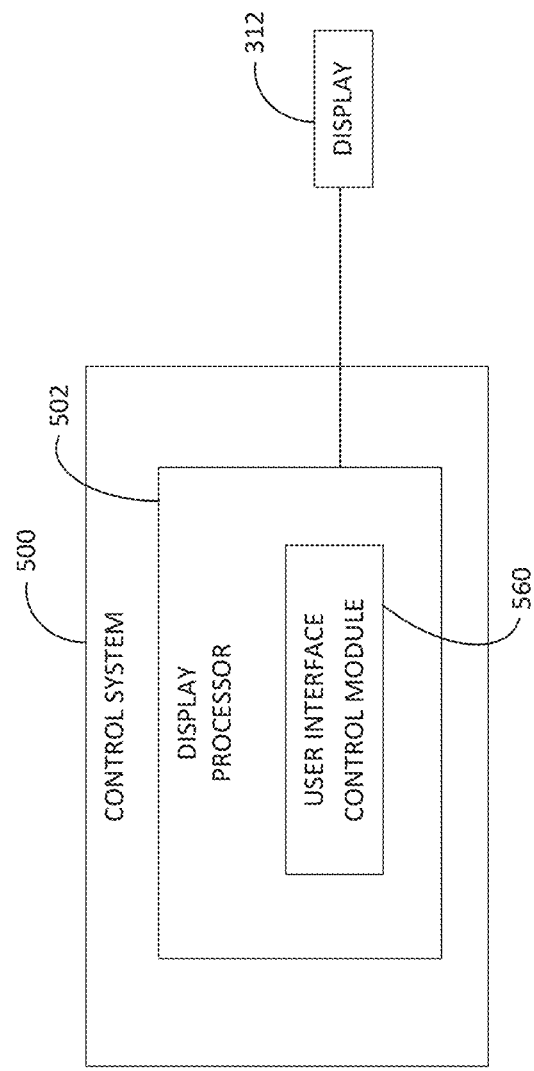
FIG. 61 is a schematic diagram of a user interface control module within the control system according to embodiments of the present disclosure.

As shown in FIGS. 55 and 61, the user interface control module 560, in some embodiments, may be configured to manage interaction of the user with the display 312 (e.g., the touch panel). For example, the user interface control module 560 may be configured to receive and process user input, and manage display of information to the user on the display 312. In some embodiments, the user interface control module 560 may be run by the display processor 502.

As noted above, to accomplish control of each of these modules, the control system may include a plurality of microcontrollers (or processors). For example, in some embodiments, the control system may include at least a control processor 501, a display processor 502, and a bay processor 503.

In some embodiments, for example, the control processor 501 may be configured to run at least portions of the positioning assembly control module 510, the camera control module 540, and the excitation control module 550. Running one or more of these modules, the control processor 501 may be utilized for system supervision, managing the camera 361 and the positioning assembly 340 (or more specifically the stepper motor 341), operating the camera 361 and the excitation source 351, processing and receiving images captured by the camera 361, sequencing spore detection tests, and managing the light sources at the door openings 316 (also referred to as a front panel LED board 504). To manage the light sources at the door openings 316, the control processor 501 may be configured to communicate with a front panel LED (or light source) board which includes the light source circuitry.

Additionally, to control the positioning assembly 340, in some embodiments, the control processor 501 may include lock-out logic to prevent the positioning assembly 340 from advancing the scan head assembly 350 past a preset threshold limit. In such embodiments, the positioning assembly 340 may further include one or more threshold sensors (as discussed generally above) to limit the movement of the scan head assembly 350 past one or more threshold limits. For example, in some embodiments, the positioning assembly 340 may include one sensor to the right of the scan head assembly 340, and another sensor to the left of the scan head assembly 340 to thereby limit movement of the scan head assembly 340 in both directions along the belt drive 342.

In some embodiments, the BI reader 300 may include an external USB diagnostic port (not shown) and/or an Ethernet port (also not shown). In embodiments including the USB diagnostic port, the control processor 501 may support the USB diagnostic port, and host a diagnostic graphical user interface (GUI). And in embodiments including the Ethernet port, the control processor 501 may be configured to facilitate the exchange of BI test data with Instrument Tracking Systems (e.g., within the hospital) to comply with data management requirements.

Additionally, in some embodiments, the display processor 502 may run the user interface control module 560. Running this module, the display processor may be configured to manage the display 312, including the touch panel (when used), and to receive and process user inputs. The display processor 502 may also support an ethernet connection.

The bay processor 503, according to some embodiments, may be configured to run at least portions of the BI bay heater control module 520, and the BI door and handler module 530. Running these modules (or portions thereof), the bay processor 503 may be configured to operate the solenoids 405, monitor and report statuses (or configurations) of the access doors 313, operate the heater cartridge 373, operate the axial fans 392, and manage certain functions of the excitation source 351. As shown in FIGS. 55 and 58, the bay processor 503 may also be configured to communicate with an upper BI sensor board 506 and the lower BI sensor board 389 which include the circuitry for the various BI sensors, including, for example, the slot sensors 329, the BI presence sensors 382, and the shuttle sensors 425. As shown in FIGS. 55 and 57, the bay processor 503 may also be configured to communicate with the temperature sensors 376 of the heater block assembly 370, and process signals from those sensors to control operation of the heater cartridge 373 and axial fans 392 in order to maintain the temperature of the heater block assembly 370 within the temperature range discussed above.

It will be appreciated that the heater block assembly 370 and the optical assembly (i.e., the positioning assembly 340 and the camera assembly 360) are calibrated with each other to provide parallelism between each of the BI bays 375 and the scan head assembly 350, such that a distance between the scan head assembly and each of the BI bays 375 is constant and such that the scan head assembly captures images at a focal plane for each of the BI bays 375. It will further be appreciated that other configurations are possible. For example, the camera assembly 360 could be located in a different portion of the BI reader housing 301 and the mirror mount 330 moved or omitted, provided that the camera assembly 360 is located such that it can receive light transmitted by the BI 100 with minimal (or reduced) interference. As another example, separate camera assemblies 360 and/or separate excitation sources 351 could be utilized for each BI bay 375, as described above. However, the present disclosure also provides for a BI reader 300 in a compact housing 301, which allows for the use of fewer components and analysis of multiple BI bays 375 without the use of separate excitation and reading equipment for each BI bay 375, thereby reducing the size and cost of the reader, as also discussed above.

According to embodiments of the present disclosure, a method of detecting the sterilization efficacy of a sterilization run includes utilizing the BI reader 300 and at least the BI 100 (and in some embodiments, the PCD 200) discussed above. According to embodiments, for example, the BI reader 300 may be utilized to test and analyze the biological indicator 100 in order to determine whether a sterility procedure to which the biological indicator 100 was exposed was successful.

First, the user may activate the BI reader 300, for example, by pressing an on/off button or interacting with the display 312 in the front panel 311 of the BI reader 300 (e.g., to wake the BI reader 300). Upon receiving such user input, the control processor activates the heater cartridge 373 to begin warming the heater block assembly 370, e.g., the first heating plate 371 and the second heating plate 372. When the first heating plate 371 and the second heating plate 372 are brought to a sufficient temperature, e.g., 60 degrees Celsius, the temperature sensor(s) 376 on the heater block assembly 370 send a signal to the control processor, and the control processor provides an indication to the user that BI reader 300 is ready for use. The indication may be via information displayed on the display 312, and/or may be via a change in the light sources associated with the access door releases 314. For example, the change in the light sources may be a change from off to on (or vice versa), a change in color (such as from red to green), or a change from on (or off) to flashing.

To perform the sterilization efficacy test, the user may depress (or otherwise actuate) the access door release 314, thereby releasing the access door 313 and exposing the door opening 313 and the chamber 326. The user may then insert the biological indicator 100 into the door opening 313, through the chamber 326 and the chamber opening 327, thereby inserting the first end 100a of the biological indicator 100 into the BI bay 375. As the first end 100a of the biological indicator 100 is inserted into the BI bay 375, the chamber 326 guides the biological indicator 100 to the chamber opening 327 and the BI bay 375, as discussed above. As the first end 100a of the biological indicator 100 continues to be moved inside the BI bay 375, the insertion groove 138 contacts the BI latch 384, which then pivots about the BI latch pin 386 and into the BI latch opening 383 to allow for proper insertion of the biological indicator 100. As the biological indicator 100 is being inserted into the BI bay 375, the BI latch 384 (e.g., the rib 387) moves toward the biological indicator 100 by means of the insertion notch 138b, and the rib 387 moves into the insertion notch 138b to hold the biological indicator 100 in place.

One biological indicator 100 may be inserted into each BI bay 375. As such, according to embodiments, for a BI reader 300 having four BI bays 375, four biological indicators 100 can be tested concurrently or simultaneously. However, it is not necessary for all of the BI bays 375 of the BI reader 300 to be occupied in order to run a detection cycle. Rather, any number of the BI bays 375 may remain empty such that a detection cycle can be run on only a single BI 100 (with all remaining bays empty), or any other number of BIs (up to the total number of bays on the reader). In such a case, the control system of the BI reader 300 receives a signal from the BI presence flag or sensor associated with each BI bay 375, and directs the scan head assembly 350 to only scan (or test) those BI bays 375 that are occupied by a BI 100. As a result, during the detection cycle, the scan head assembly 350 will move from bay to bay, but will only emit light from the excitation source into the BI bays 375 that are occupied. While the scan head assembly 350 may stop below the empty bays, the excitation source will not be activated at the empty bays 375. Alternatively, the control system may direct the scan head assembly 350 skip the empty bays altogether, so that the scan head assembly 350 does not stop at the empty bays, and moves only between the bays that are occupied.

After the biological indicator 100 is inserted into the BI bay 375, the user may close the access door 313, e.g., by actuating the access door release 314 again, or by manually lowering the access door. After all access doors 313 are closed, the BI reader 300 may perform a variety of software checks to ensure the BI reader 300 is ready to perform the test. For example, utilizing the scan head assembly 350 and/or the camera assembly 360, the control system may initiate a dust check to check for dust particles in the optical path by checking for high frequency noise in the field of view of the scan head assembly (e.g., the field of view defined by the BI window 379 of the bay 375), indicating the presence of foreign matter in the optical path (e.g., between the BI window 379 of the BI bay 375 and the imaging window 190 of the BI 100). The BI reader 300 may also conduct a condensation check to check for condensation formed on the BI window 379 during heating of the heater block assembly 370. The BI reader 300 may also perform an alignment check of the biological indicator 100 to ensure that the BI window 379 is properly aligned in the BI bay 375, for example, by detecting the Odin's cross shape of the bottom opening 132 and confirming that the biological indicator 100 has been inserted within acceptable tolerances. The BI reader 300 may also perform a positioning check to ensure proper calibration of the scan head assembly 350 and the positioning assembly 340 and a correct distance between the scan head assembly 350 and the heater block assembly 370 (and therefore the BI window 379). The self-calibration target 369 may be utilized to check for proper calibration of the scan head assembly 350 and the positioning assembly 340 by emitting light toward the self-calibration target 369 and measuring a pattern reflected from the calibration target 369 to ensure proper distancing between the scan head assembly and the heater block assembly 370. If any of these systems checks fail, the control processor will deliver a fault or error message, which may include fault or error information displayed on the display 312, and/or may be via a change in the light sources associated with the access door releases 314. In addition, the BI reader 300 may include a z-focus adjustment via the optical assembly to estimate any deviation from the ideal focal plane (e.g., range finding) of the spore carrier 180 during a test cycle. The z-focus adjustment may be accomplished by utilizing an electronically controlled micrometer with the scan head assembly 350 such that a focal distance of the collection lens 353 may be adjusted within a range of +/−250 μm.

If the systems checks all pass, the control system (via, e.g., the control processor) activates the solenoid 405 to push the center rod 406 of the solenoid 405 toward the shuttle 420 along the depth direction $Y_R$ of the BI reader 300, thereby overcoming the tension of the shuttle spring 410 and driving the shuttle 420 toward the front panel 311. The activation of the solenoid 405 effectuates locking of the access doors 313 in the closed position. As the shuttle 420 moves forward, the cam bearing 421 of the shuttle 420 interacts with the cam surface 402 of the germinant release lever 401, actuating the cam surface 402 in a clockwise direction. The push rod 403 then extends downwardly toward the BI bay 375 and into the opening 121 in the BI housing 110. Additionally, the door interlock spring 422 of the shuttle 420 engages with the retaining clip 319 to lock and prevent rotation of the access door 313 while the shuttle 420 is activated.

The push rod 403 extends downwardly through the opening 121 of the BI housing 110, applying pressure on the germinant releaser 170, which in turn, applies pressure on the germinant releaser support 140, which together with the germinant releaser 170 applies pressure against the germinant container 160, thereby rupturing the germinant container 160 and releasing the germinant 165 contained therein into the interior of the BI 100. The germinant 165 saturates the germinant pad 185 which wicks the germinant through the germinant pad 185 onto the spore carrier 180 which contains the spores 181 on an underside thereof. The germinant 165 then wicks through the spore carrier 180 to reach the spores on the underside thereof.

As discussed above, when the spores 181 on the spore carrier 180 are killed during the sterilization run, those spores release DPA. When those spores (or more accurately, the DPA released from those spores) come in contact with the germinant solution 165, the photoluminescent component of the germinant solution (e.g., Tb ions) may bind to the DPA to form a photoluminescent complex (e.g., a Tb-DPA complex) that will luminesce upon activation by UV light. After the germinant 165 is released inside the biological indicator 100, the control system may activate the optical assembly, which generates, captures, and analyzes images of the activity inside each biological indicator 100. More specifically, the control system activates the positioning assembly to move the linear guide block 343 along the guide rail 343*a* to align the scan head assembly 350 beneath the first occupied BI bay 375. The scan head assembly 350 then emits light from the excitation source 351 toward the BI window 379, which light passes through the emission lens 352, the excitation filter 354, the BI window 379, and the imaging window 190 to the spores 181 inside the biological indicator 100. This activates the photoluminescent complex, which begins to luminescence and emit back toward the imaging window, along the optical path described above (i.e., through the imaging window 190, the BI window 379 in the heater block assembly 370, the collection lens 353, to the first mirror 355, which reflects the light along the width direction $X_R$ to the second mirror 331, which then reflects the light along the depth direction $Y_R$ to the camera assembly 360) to the camera 361. In some embodiments, the camera 361 captures the luminescence generated by the dead spores as a bright, static background image. However, it is understood that in some embodiments, the camera may not capture a background image.

As also discussed above, when any spores 181 on the spore carrier 180 survive the sterilization cycle, these viable (or live) spores will begin to germinate upon contact with the germinant (e.g., L-alanine) in the germinant solution 165. Upon germination, these live spores will release DPA, which may then bind to the photoluminescent component of the germinant solution 165. The resulting DPA-photoluminescent complex will then luminesce upon activation with UV light, as described above in connection with the dead spores. However, because the live spores release their DPA after germination, there is a time-lapse and an amplitude increase between any DPA signal received by the camera from the dead spores, and the DPA signal received by the camera from the live spores. Accordingly, when the camera detects a DPA signal that is above the static background signal from the dead spores, the control system returns an indication that the sterilization cycle failed. This indication can be via information displayed on the display 312, and/or via a change in the light sources associated with the access door releases 314 and/or via an audio alarm.

Prior to running the detection protocols, the control system may also run a check using the optical assembly to initially detect whether the germinant 165 was successfully released, thereby saturating the spore carrier 180. The optical assembly and control system conduct this check by detecting and calculating the average intensity of light emitted over time. For example, if the control system and optical assembly detect an intensity change at or above a specified threshold intensity ratio (e.g., approximately 110%) over time, the BI reader 300 registers the germinant 165 as having been successfully released, and proceeds with the detection cycle. However, if the control system and optical assembly detect an intensity that is lower than the specified threshold intensity, the BI reader 300 registers the germinant as not having been adequately released, and returns a fault or error. As discussed above, the fault or error may be indicated via information displayed on the display 312, and/or may be via a change in the light sources associated with the access door releases 314.

Additionally, according to some embodiments, the threshold intensity used in this system test is based on the expected level of luminescence from the spores 181 after the sterilization cycle. For example, given the number and type of spores 181 on the spore carrier 185, the threshold intensity level for this test may be based on a percentage of the expected level of luminescence assuming all spores 181 were killed during the sterilization cycle (and thus released their DPA prior to germinant release). As the dead spores 181 would be expected to luminesce and return an intensity signal relatively quickly upon contact with the germinant 165, a lower than expected luminescence intensity may indicate a failure of the germinant 165 to fully release and properly saturate the spore carrier 185. The threshold intensity (or threshold percentage of the expected luminescence intensity) is not particularly limited so long as it is sufficiently high to accurately determine whether the germinant 165 was properly released. In some embodiments, the threshold intensity may be set to 2000, i.e., out of the range of 0-65535 levels (for a 16-bit image). However, it is understood that in some embodiments, the BI reader 300 does not detect or capture images of a background (or expected luminescence). In such embodiments, the threshold intensity in this test would be set to 0, or this test would be omitted.

Assuming the germinant release system test described above passes, the control system directs the BI reader 300 to continue with the detection cycle. During the detection cycle, the optical assembly may emit light from the excitation source into the BI 100 in each occupied bay, and capture multiple images of the luminescence emitted back through the imaging window 190 and the BI window 379, as discussed above, and In some embodiments, to determine whether there are live spores, the control system may generate a signal-to-noise ratio, comparing any received luminescence signal to the static background image (when present). In particular, if any spores 181 remained viable after the sterilization procedure, the luminescence emitted back initially may be below an anticipated threshold. The live spores 181, then, would release their DPA after germination (i.e., sometime after initial contact with the germinant solution 165), at which time, the newly released DPA would bind with the photoluminescent component of the germinant solution and luminescence (upon activation with the light from the excitation source). However, as this luminescence signal occurs after the live spores have had the time to germinate, this live spore signal does not appear until after the static background image (when present) has been established. As such, any signal from a live spore will appear above the static background signal (when present) or as a time-lapsed signal, and be identified by the control system as indicative of a live spore, and therefore sterilization failure.

To ensure that the indication of sterilization success or failure is accurate, the entire spore carrier is assessed over time to determine whether any live spores remain. More specifically, while the scan head assembly 350 is positioned under an occupied BI bay 375, the excitation source emits light on the spore carrier, and the camera captures multiple images of the entire spore carrier. These images captured by the camera assembly 360 are then transmitted to the control processor which may analyze each of the images, e.g., to compare signal to noise (or background) for the returned images. In some embodiments, for example, the processor analyzes each of the captured images pixel-by-pixel. This analysis of the captured images pixel-by-pixel enables quantification of the number of live spores, thus providing a more accurate assessment of sterilization efficacy. In particular, when a spore releases DPA (either from being killed during the sterilization cycle or from germination), the DPA typically releases close to the spore. However, the DPA released by dead spores 181 have had sufficient time to diffuse over the spore carrier 180 by the time the BI 100 is being processed. In contrast, DPA is released by live spores 181 in real time (e.g., in 15 second intervals) and the DPA does not have sufficient time to diffuse away from its pixel location. Thus, the DPA signal from a live spore 181 appears as a local intensity perturbation. As such, the imaging and analysis protocols described herein enable imaging of individual spores on the spore carrier by looking at each pixel on the spore carrier 180. With a known number of pixels and known number of spores 181 on the spore carrier 180, the number of live spores 181 can be quantified by the control processor. To that end, the number of pixels is not particularly limited, but in some embodiments, each image may contain 160×160 pixels.

As noted above, when one or more spores remain viable after the sterilization cycle, they will generate a luminescence signal later in time than BI activation, or later in time than the signal generated by dead spores (which contribute to the background signal, when present). Accordingly, in some embodiments, the optical assembly may be configured to capture images at each BI bay 375 at regular time intervals. The length of each interval is not particularly limited, but should be long enough to capture multiple images of the spore carrier during each stop at the respective BI bay 375. For example, in some embodiments, each interval may be about 3 seconds long, such that when the scan head assembly 350 stops at an occupied bay 375, it remains there for 3 seconds, emitting light onto the spore carrier, and capturing an image of the luminescence returned by the spore carrier, such image being an accumulation of photons captured over thousands of exposures. More specifically, in some embodiments, the linear guide block 343 (driven by the stepper motor and belt drive) rides on the guide rail 343a until it reaches the first occupied bay 375. When it reaches the first occupied bay 375, the linear guide block 343 is stopped there for the time interval (e.g., for 3 seconds). After this time interval passes, the linear guide block 343 is moved again along the guide rail 343a until it reaches the next occupied bay 375, where it is stopped again for the time interval. This continues until all occupied bays 375 are visited by the scan head assembly. And when the scan head assembly 350 reaches the last occupied BI bay 375, it returns to the first occupied bay 375 for a second time interval (which is usually equal in length to the first time interval, but may vary if desired), and then cycles through the remaining occupied bays again. The scan block assembly 350 may be operated in this cycling mode for any number of cycles such that each occupied bay 375 undergoes multiple illumination and image capture cycles during each detection cycle of the BI reader 300. This time-gated imaging of the spore carrier enables the BI reader 300 and the control processor to compare the time-gated images to each other, and detect any luminescence signals appearing at different times, or appearing above the initially established background image (when present). As discussed above, when coupled with the pixel-by-pixel analysis of these images, this allows the BI reader 300 to detect individual spores on the spore carrier, and to quantify the number of spores that remained alive after the sterilization procedure. It is understood that the occupied bays 375 of the reader 300 may be analyzed in this manner in any order, including, e.g., beginning the scan head assembly cycles from a left-most bay, a right-most bay, or a bay somewhere in the middle.

According to embodiments, the BI reader 300 can complete a full detection cycle (i.e., including multiple cycles of the scan head assembly 350) in about 15 minutes or less. As discussed above, the positioning assembly 340 may move the scan head assembly 350 beneath various of the BI bays 375 for relatively brief intervals, and may cycle through each of the BI bays 375 multiple times during one detection cycle. As such, multiple images at each BI bay 375 are captured, which provides a history of images over time. The BI reader 300 may be configured to analyze patterns at each biological indicator 100 over time, reducing the likelihood of noise providing a false negative, thereby improving reliability of the BI reader 300. According to embodiments, when a live spore 181 is detected in one of the BI bays 375, the detection cycle may be stopped, or the BI bay 375 may be omitted during continued testing of other BI bays 375 for any live spores 181.

After the detection cycle of the BI reader 300 is complete, the BI reader 300 may output a reading or indication to the user, indicating whether each of the tested biological indicators 100 had any live spores. The reading or indication output by the reader may be either via information displayed on the display 312 and/or via a change in the light sources associated with the door releases 314. For example, if the reading or indication is that a BI 100 did test positive for live spores during the detection cycle (and therefore that the sterilization cycle associated with that BI failed), the BI reader 300 may identify the bay number on the display next to an indication such as "fail," or any other indication that tells the user that the sterilization cycle associated with that BI was not successful. Additionally or alternatively, the light source corresponding to the BI bay may change, e.g., from off to on (or vice versa), from one color to another (e.g., from green to red, or vice versa), from on to flashing, etc. Also additionally or alternatively, the BI reader 300 may include an audio alarm that may sound in the event of detection of a live spore (or in the case of a system fault, as discussed above). Similarly, if no live spores were detected during the detection cycle (thereby indicating that the sterilization cycle was successful), the reader 300 may identify the bay number on the display next to an indication such as "pass," or any other indication that tells the user that the sterilization cycle associated with that BI was successful. Additionally or alternatively, the light source corresponding to the BI bay may change, e.g., from off to on (or vice versa), from one color to another (e.g., from red to green, or vice versa), from on to flashing, etc. Also additionally or alternatively, the audio alarm may sound, e.g., with a distinct sound indicating success (whereas a different sound may be used to indicate failure of the sterilization cycle, and another different sound may be used to indicate a system fault).

When the detection cycle is complete, the solenoid 405 is retracted, releasing the shuttle 420, which is retracted toward the rear panel 391, thus moving the door interlock spring 421 away from the retaining clip 319, and unlocking the access door 313 at the hook portion 313c. As the shuttle 420 is retracted, the germinant release lever 401 is released and the push rod 403 is retracted from the opening 121 in the biological indicator 100. The user may then depress (or otherwise actuate) the access door release 314, which releases the access door 313, allowing for removal of the biological indicator 100. The secondary spore carrier may then be removed from the biological indicator 100 and used to run a reference culture test to verify the results returned by the BI reader 300 (if necessary).

While certain exemplary embodiments of the present disclosure have been illustrated and described, those of ordinary skill in the art will recognize that various changes and modifications can be made to the described embodiments without departing from the spirit and scope of the present invention, and equivalents thereof, as defined in the claims that follow this description. For example, although certain components may have been described in the singular, i.e., "a" germinant compound, and the like, one or more of these components in any combination can be used according to the present disclosure.

Also, although certain embodiments have been described as "comprising" or "including" the specified components, embodiments "consisting essentially of" or "consisting of" the listed components are also within the scope of this disclosure. For example, while embodiments of the present disclosure are described as comprising a BI housing, a germinant container, a germinant releaser, a germinant releaser support, a first spore carrier, and an imaging window, embodiments consisting essentially of or consisting of these components are also within the scope of this disclosure. Accordingly, a biological indicator may consist essentially of a BI housing, a germinant container, a germinant releaser, a germinant releaser support, a first spore carrier, and an imaging window. In this context, "consisting essentially of" means that any additional components or process actions will not materially affect the product or the results of the detection cycle (e.g., of the system or BI reader).

As used herein, unless otherwise expressly specified, all numbers such as those expressing values, ranges, amounts or percentages may be read as if prefaced by the word "about," even if the term does not expressly appear. Further, the word "about" is used as a term of approximation, and not as a term of degree, and reflects the penumbra of variation associated with measurement, significant figures, and interchangeability, all as understood by a person having ordinary skill in the art to which this disclosure pertains. Any numerical range recited herein is intended to include all sub-ranges subsumed therein. Plural encompasses singular and vice versa. For example, while the present disclosure may describe "a" germinant compound, a mixture of such compounds can also be used. When ranges are given, any endpoints of those ranges and/or numbers within those ranges can be combined within the scope of the present disclosure. The terms "including" and like terms mean "including but not limited to," unless specified to the contrary.

Any numerical value inherently contains certain errors necessarily resulting from the standard variation found in their respective testing measurements. The word "comprising" and variations thereof as used in this description and in the claims do not limit the disclosure to exclude any variants or additions.

What is claimed is:

1. A biological indicator (BI) comprising:
   a BI housing;
   a germinant container inside the BI housing and housing a germinant composition;
   a germinant releaser configured to release the germinant composition from the germinant container;
   a germinant releaser support supporting the germinant releaser and configured to bring the germinant releaser into contact with the germinant container upon application of a force to the germinant releaser support or the germinant container, the germinant releaser support comprising:
      a seat defining a germinant releaser opening which receives the germinant releaser; and
      a plurality of support legs which support the seat and are configured such that the seat is located above the germinant container, the plurality of support legs having flexibility to allow for movement of the seat when downward pressure is applied to the seat;
   a first spore carrier inside the BI housing, the first spore carrier having a plurality of spores deposited at a first surface thereof; and
   an imaging window at a first surface of the BI housing.

2. The biological indicator of claim 1,
   wherein the BI housing defines an opening at a second surface thereof, the second surface opposite to the first surface, the opening configured to receive a germinant release means of a BI reader during BI activation for releasing the germinant from the germinant container,
   wherein the opening is located above the germinant releaser along a thickness direction of the biological indicator, and
   wherein the opening, the germinant container, the germinant releaser, the spore carrier, and the imaging window are all stacked along the height direction.

3. The biological indicator of claim 1, wherein the germinant container comprises a glass ampoule or an outer container having a hollow interior sealed by a barrier.

4. The biological indicator of claim 1:
   wherein the first spore carrier is generally planar and has a first side and a second side, said first surface of the first spore carrier being on the first side such that the first spore carrier carries said plurality of spores on the first side thereof,
   the first side of the first spore carrier with the plurality of spores thereon being positioned parallel to the imaging window for viewing through the imaging window, and
   the germinant composition being configured to contact the first spore carrier and the first plurality of spores thereon after BI activation.

5. The biological indicator of claim 1, wherein:
   the first spore carrier is positioned between a germinant pad and the imaging window, and
   the first spore carrier, the germinant pad, and the imaging window are all positioned in a stacked arrangement as substantially parallel planes.

6. The biological indicator of claim 1, further comprising a germinant pad positioned adjacent to the first spore carrier,
   wherein the germinant releaser is movable towards the first spore carrier and the germinant pad during BI activation to release the germinant composition from the germinant container, and the germinant releaser being configured to press the germinant pad against the first spore carrier towards the imaging window at least during BI activation to hold the germinant pad and first spore carrier in place.

7. The biological indicator of claim 1, wherein at least the first surface of the first spore carrier comprises a planar surface holding the plurality of spores which first surface is gray or black in color.

8. A process challenge device for use in determining the efficacy of a sterilization cycle, the process challenge device comprising:
   a tray defining a first cavity and a tab;
   a closure portion configured to be attached to the tray to seal the first cavity;
   a sterilant sterilization integrator; and
   a sterilant access port,
   the first cavity containing the biological indicator of claim 1 and the sterilant sterilization integrator, the tab being configured to separate the biological indicator and the sterilant sterilization integrator.

9. A biological indicator (BI) comprising:
   a BI housing;
   a germinant container inside the BI housing and housing a germinant composition;
   a germinant releaser configured to release the germinant composition from the germinant container;
   a germinant releaser support supporting the germinant releaser and configured to bring the germinant releaser into contact with the germinant container upon application of a force to the germinant releaser support or the germinant container;
   a first spore carrier inside the BI housing, the first spore carrier having a plurality of spores deposited at a first surface thereof; and
   an imaging window at a first surface of the BI housing,
   the BI housing defining an opening located above or adjacent the germinant releaser, the opening being configured to receive a germinant release means of a BI reader during BI activation for releasing the germinant from the germinant container,
   the BI housing further comprising a sterilant entry port at a location different from the opening, and
   prior to BI activation, the opening is sealed by a sealant material to exclude sterilant, and the sterilant entry port is open to receive sterilant.

10. The biological indicator of claim 9, further comprising a germinant pad, the first spore carrier being positioned between the germinant pad and the imaging window, and
   the first spore carrier, the germinant pad, and the imaging window are all positioned in a stacked arrangement as substantially parallel planes.

11. The biological indicator of claim 10, wherein the germinant releaser is movable towards the first spore carrier and the germinant pad during BI activation to release the germinant composition from the germinant container, and the germinant releaser being configured to press the germinant pad against the first spore carrier towards the imaging window at least during BI activation to hold the germinant pad and first spore carrier in place.

12. The biological indicator of claim 9, wherein at least the first surface of the first spore carrier is gray or black in color.

13. A biological indicator (BI) comprising:
   a BI housing;
   a germinant container inside the BI housing and housing a germinant composition;
   a germinant releaser configured to release the germinant composition from the germinant container;
   a germinant releaser support supporting the germinant releaser and configured to bring the germinant releaser into contact with the germinant container upon application of a force to the germinant releaser support or the germinant container;
   a first spore carrier inside the BI housing, the first spore carrier having a plurality of spores deposited at a first surface thereof; and
   an imaging window at a first surface of the BI housing,
   the BI housing comprising a grip portion and a protrusion portion, the grip portion and protrusion portion being lateral to each other along a length dimension of the biological indicator, the protrusion portion being configured to house at least a portion of the germinant container, the germinant releaser, the germinant releaser support and the first spore carrier.

14. The biological indicator of claim 13, further comprising a germinant pad, the first spore carrier being positioned between the germinant pad and the imaging window,
   the first spore carrier, the germinant pad, and the imaging window are all positioned in a stacked arrangement as substantially parallel planes, and
   in the activated position, the germinant releaser or germinant releaser support presses the first spore carrier and the germinant pad towards the imaging window.

15. The biological indicator of claim 13,
   wherein the imaging window is on a bottom surface of the BI housing, and the first surface of the first spore carrier and the plurality of spores thereon are oriented downward towards the imaging window; and
   wherein the BI housing has side walls which are opaque.

16. The biological indicator of claim 15, further comprising an insertion groove on an exterior surface of at least one side wall of the BI housing for engagement with a BI reader.

17. The biological indicator of claim 13, further comprising an opening in the protrusion portion of the BI housing opposite the imaging window, and a sealant material sealing the opening prior to BI activation, and which sealant is configured to be broken during BI activation.

18. The biological indicator of claim 13, wherein the protrusion portion of the BI housing comprises an opening in the BI housing located above the germinant releaser along a thickness direction of the protrusion portion, and the opening, the germinant container, the germinant releaser, the first spore carrier, and the imaging window are all stacked along the height direction in the protrusion portion.

19. A biological indicator (BI) comprising:
   a BI housing having a first surface and second surface opposite the first surface, the BI housing defining an opening at the second surface, the opening being located in an area adjacent a first end of the BI housing, and the biological indicator further comprising a sterilant opening at a second end of the BI housing, the second end opposite to the first end;
   a germinant container inside the BI housing and housing a germinant composition;
   a germinant releaser configured to release the germinant composition from the germinant container;
   a germinant releaser support supporting the germinant releaser and configured to bring the germinant releaser into contact with the germinant container upon application of a force to the germinant releaser support or the germinant container;
   a first spore carrier inside the BI housing, the first spore carrier having a plurality of spores deposited at a first surface thereof; and
   an imaging window at a first surface of the BI housing.

20. The biological indicator of claim 19, wherein:
the opening is located above the germinant releaser along a thickness direction of the biological indicator, and
the opening, the germinant container, the germinant releaser, the spore carrier, and the imaging window are all stacked along the height direction.

21. The biological indicator of claim 19, wherein the opening is aligned with the germinant container and the first spore carrier,
the opening being sealed against sterilant entry via the opening prior to BI activation, and the opening being configured to receive a germinant release means of a BI reader during BI activation for releasing the germinant from the germinant container.

* * * * *